United States Patent [19]
Sekine et al.

[11] Patent Number: 6,149,837
[45] Date of Patent: Nov. 21, 2000

[54] PHENYLACETYLENE COMPOUND AND LIQUID CRYSTAL COMPOSITION COMPRISING THE SAME

[75] Inventors: Chizu Sekine; Koichi Fujisawa, both of Tsukuba; Naoto Konya, Takatsuki; Masayoshi Minai, Moriyama, all of Japan

[73] Assignees: Sumitomo Chemical Company, Limited, Osaka; Agency of Industrial Science and Technology; New Energy and Industrial Technology Development Organization, both of Tokyo, all of Japan

[21] Appl. No.: 09/257,065

[22] Filed: Feb. 25, 1999

[30] Foreign Application Priority Data

Feb. 25, 1998 [JP] Japan .................. 10-043289
Oct. 29, 1998 [JP] Japan .................. 10-309091
Nov. 26, 1998 [JP] Japan .................. 10-335336

[51] Int. Cl.$^7$ .............. C09K 19/06; C09K 19/52; C09K 19/34; C07C 255/00
[52] U.S. Cl. .............. 252/299.6; 252/299.01; 252/299.63; 252/299.61; 558/425
[58] Field of Search .............. 252/299.6, 299.01, 252/299.63, 299.61; 558/425

[56] References Cited

U.S. PATENT DOCUMENTS

| | | | |
|---|---|---|---|
| 5,250,216 | 10/1993 | Goto et al. .............. | 252/299.6 |
| 5,792,387 | 8/1998 | Hachiya et al. .............. | 252/299.6 |
| 5,820,785 | 10/1998 | Schlosser et al. .............. | 252/299.63 |
| 5,866,036 | 2/1999 | Wand et al. .............. | 252/299.6 |

FOREIGN PATENT DOCUMENTS

| | | |
|---|---|---|
| 2-83340 | 3/1990 | Japan . |
| 9-216841 | 8/1997 | Japan . |

OTHER PUBLICATIONS

Shin –Tson Wu, Appl. Phys. Lett., 1999, vol. 74 (3), pp. 344–346.
Shin–Tson Wu, Jpn. J. Appl. Phys., Part 2, 1999, vol. 38 (3b), pp. L286–L288.
B. Konig et al., Chem. Ber., 1993, vol. 126, pp. 1643–1650.
F. Vogtle et al., Chem Ber., 1992, vol. 125, pp. 2129–2135 (with English language Abstract attached).
Ulrich Ziener et al., J. Org. Chem., 1997, vol. 62, pp. 6137–6143.
LeRoy Jones, II, et al., J. Org. Chem., 1997, vol. 62 (5), pp. 1388–1410.
Coleen Pugh et al., Marcromolecules, 1997, vol. 30, pp. 4520–4532.
M. S. Yusubov et al., Zh. Org. Khim., 1996, vol. 32 (8), pp. 1276–1277 (with English language Abstract attached).
Jacques Malthete et al., Molecular Crystals and Liquid Crystals, 1973, vol. 23, pp. 233–260.

*Primary Examiner*—C. H. Kelly
*Attorney, Agent, or Firm*—Birch, Stewart, Kolasch & Birch, LLP

[57] ABSTRACT

Provide is a novel phenylacetylene compound (1) which has a large anisotropy of refractive index, tends to be mixed with other liquid crystals, and is more advantageous in stability to light, a liquid crystal composition and a liquid crystal element usable for an optical shutter, a display element,

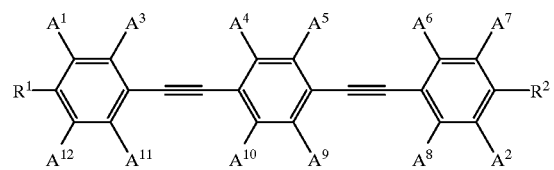

(1)

$A^1$ to $A^{12}$ each independently represent a hydrogen atom, a fluorine atom, or an alkyl group having 1 to 10 carbon atoms, and at least one is an alkyl group.

14 Claims, No Drawings

PHENYLACETYLENE COMPOUND AND LIQUID CRYSTAL COMPOSITION COMPRISING THE SAME

BACKGROUND OF THE INVENTION

1. Field of the Invention

The present invention relates to a novel phenylacetylene compound having an alkyl group in its core, which is useful as a component of a liquid crystal display element or a component of a liquid crystal composition, a liquid crystal composition including the same, and a liquid crystal element using the same. More particularly, it relates to a liquid crystal compound having a large anisotropy of refractive index (Δn), a liquid crystal composition, and liquid crystal elements using the same, such as an optical shutter and display elements represented by a STN (supertwisted nematic) liquid crystal element, and a PDLC (polymer dispersed liquid crystal) type liquid crystal element.

2. Description of the Related Art

With the progress of information-oriented society in recent years, various kinds of display elements have more and more increased in importance as one of the man-machine interfaces. In such circumstances, a flat-panel display, especially a liquid crystal display (LCD), has rapidly achieved widespread use because it has characteristics such as thinness, light weight, driving at a low voltage, and low consumption of electric power. Among the liquid crystal elements represented by a liquid crystal display, a matrix type liquid crystal display, which stores a large amount of information, has two driving systems referred to as an active matrix system and a passive matrix system, respectively.

In the active matrix system, a thin film transistor such as a polysilicon or amorphous silicon or a diode is provided on each pixel as a non-linear element. However, the active matrix system has some problems in increasing the picture area, lowering the price and increasing the density, because of complicated production processes and low yield. Taking price, productivity, and the like into consideration, the passive matrix system is more predominant.

As the passive matrix system liquid crystal elements which are practically used at present, TN (twisted nematic) and STN liquid crystal elements are mainly used. The TN type has found widespread application as display elements such as watches and portable calculators. With this system, rise of electrooptical properties is slow, and a contrast is considerably decreased with an increase in duty ratio, and hence it is difficult in principle to set up a display having a large picture area. The STN type is a system developed for compensating for the drawbacks of the TN liquid crystal element. It has sharply rising electrooptical properties, which enables the implementation of a large picture area. At present, it is used as a display for notebook personal computer, and the like.

However, while the STN liquid crystal element has more excellent characteristics as compared with the TN liquid crystal element, it still has some problems to be solved for a further increase in picture area, decrease in price, and increase in density.

For example, in comparison with the TFT liquid crystal element which is one of the typical examples of the active matrix system, the STN liquid crystal element is still insufficient in terms of a viewing angle characteristic and response speed. Especially, achievement of rapid response is essential for a further increase in picture area and density, displaying motion pictures, or the like.

To achieve the rapid response of the STN liquid crystal element, a decrease in cell thickness is one of effective methods. The STN type utilizes a birefringence effect for a displaying method. To use this system, it is necessary to suppress the change in tonality and optical characteristics of a panel, that is, to set a retardation at a constant optimum value. The retardation R is represented by R=(Δn×d), and hence the anisotropy of refractive index (Δn) is required to be increased for reducing the cell thickness d.

As a liquid crystal having a relatively large anisotropy of refractive index, a tolan compound is known [Mol. Cryst. Liq. Cryst., vol., 23, p. 233 (1973)]. However, the anisotropy of refractive index is approximately 0.2, which is not a passable value. There has also been developed a compound (2) represented by the following formula (JP-A-2-83340);

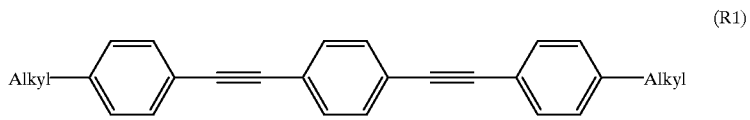

(R1)

wherein Alkyl represents an alkyl group.

The compound (R1) has an anisotropy value of refractive index of 0.3 or more. However, it has a bad compatibility with other liquid crystals, and hence it is impractical. Then, there has been developed a compound (R2) represented by the following formula for a purpose of improving the compatibility with other liquid crystals (JP-A-9-216841);

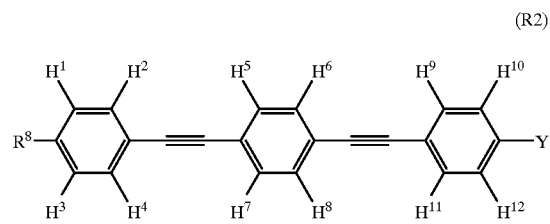

(R2)

wherein $R^8$ represents an alkyl group, Y represents $R^8$, a fluorine atom, a chlorine atom, a bromine atom, an iodine atom or a cyano group, $H^1$ to $H^{12}$ represent a hydrogen atom, a fluorine atom or a chlorine atom (provided that at least one of the $H^1$ to $H^{12}$ is a fluorine atom or a chlorine atom).

The compound (R2) is more improved in terms of compatibility with other liquid crystals than in the case of the compound (R1). However, the hydrogen atom has been substituted by a halogen atom such as a fluorine atom, and hence the anisotropy of refractive index is reduced. Thus, the anisotropy of refractive index is sacrificed in return for the improvement in compatibility.

SUMMARY OF THE INVENTION

An object of the present invention is to provide a novel phenylacetylene compound which has a large anisotropy of refractive index, tends to be mixed with other liquid crystals, and is more advantageous in stability to light, a liquid crystal composition using the same, and a liquid crystal element usable for an optical shutter, a display element, and the like, using the same.

DETAILED DESCRIPTION OF THE INVENTION

According to the present invention, phenylacetylene compound represented by the following general formula (1) is provided.

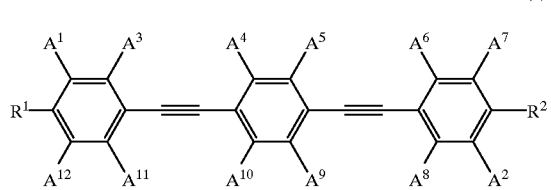

(1)

In the formula, $A^1$ to $A^{12}$ each independently represent a hydrogen atom, a fluorine atom, or an alkyl group having 1 to 10 carbon atoms, and at least one is an alkyl group (provided that, in $A^1$ to $A^{12}$, the cases are excluded where both of $A^1$ and $A^2$ are methyl groups at the same time, while the others are hydrogen atoms, and where both of $A^7$ and $A^{12}$ are methyl groups at the same time, while the others are hydrogen atoms); $R^1$ and $R^2$ each independently represent a hydrogen atom, a fluorine atom, a cyano group, a 4-$R^3$-(cycloalykyl) group, a 4-$R^3$-(cycloalkenyl) group, or a $R^4$—$(O)_q$ group (where $R^3$ represents a hydrogen atom, a linear or branched alkyl group having 1 to 12 carbon atoms which may be substituted by fluorine, a linear or branched alkenyl group having 2 to 12 carbon atoms which may be substituted by fluorine, or a linear or branched alkynyl group having 2 to 12 carbon atoms which may be substituted by a fluorine atom, and $R^4$ represents a linear or branched alkyl group having 1 to 12 carbon atoms which may be substituted by a fluorine atom, a linear or branched alkenyl group having 2 to 12 carbon atoms which may be substituted by a fluorine atom, or a linear or branched alkynyl group having 2 to 12 carbon atoms which may be substituted by a fluorine atom; and q represents 0 or 1).

According to the present invention, in the above general formula (1), provided is the above phenylacetylene compound characterized by that at least one group selected from the group consisting of $A^4$, $A^5$, $A^9$ and $A^{10}$ is an alkyl group.

Moreover, according to the present invention, a liquid crystal composition is provided comprising at least one phenylacetylene compound represented by the following formula (2), and at least one compound represented by the following formula (3), and/or a compound represented by the following formula (4),

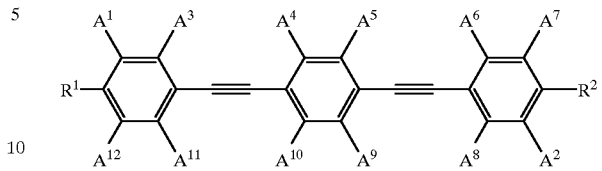

(2)

wherein $A^1$ to $A^{12}$ each independently represent a hydrogen atom, a fluorine atom, or an alkyl group having 1 to 10 carbon atoms, and at least one is an alkyl group; $R^1$ and $R^2$ each independently represent a hydrogen atom, a fluorine atom, a cyano group, a 4-$R^3$-(cycloalykyl) group, a 4-$R^3$-(cycloalkenyl) group, or a $R^4$—$(O)_q$ group (where $R^3$ represents a hydrogen atom, a linear or branched alkyl group having 1 to 12 carbon atoms which may be substituted by fluorine, a linear or branched alkenyl group having 2 to 12 carbon atoms which may be substituted by fluorine, or a linear or branched alkynyl group having 2 to 12 carbon atoms which may be substituted by a fluorine atom, and $R^4$ represents a linear or branched alkyl group having 1 to 12 carbon atoms which may be substituted by a fluorine atom, a linear or branched alkenyl group having 2 to 12 carbon atoms which may be substituted by a fluorine atom, or a linear or branched alkynyl group having 2 to 12 carbon atoms which may be substituted by a fluorine atom; and q represents 0 or 1),

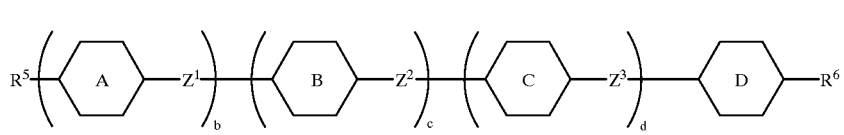

(3)

in the formula (3), rings A, B, C and D each independently represent 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, 6,3-cyclohexenylene, 2,5-pyrimidinediyl, 5,2-pyrimidinediyl, 2,5-pyridinediyl, 5,2-pyridinediyl, 2,5-dioxanediyl, or 5,2-dioxanediyl (provided that each hydrogen atom on the rings A, B, C, and D may be substituted by a fluorine atom); $R^5$ and $R^6$ represent a hydrogen atom, a fluorine atom, a fluoromethyl group, a difluoromethyl group, a trifluoromethyl group, a fluoromethoxy group, a difluoromethoxy group, a trifluoromethoxy group, a cyano group, a linear or branched alkyl group having 1 to 12 carbon atoms, a linear or branched alkenyl group having 2 to 12 carbon atoms, a linear or branched alkoxy group having 1 to 12 carbon atoms, a linear or branched alkenyloxy group having 2 to 12 carbon atoms, a linear or branched alkynyloxy group having 3 to 12 carbon atoms, a linear or branched alkoxyalkyl group having 2 to 16 carbon atoms, or a linear or branched alkoxyalkenyl group having 3 to 16 carbon atoms, and methylene groups of alkyl, alkenyl or alkynyl group thereof may be replaced with oxygen, sulfur or silicon atom; $Z^1$, $Z^2$ and $Z^3$ each independently represent —COO—, —OCO—, —OCH$_2$—, —CH$_2$O—, an alkylene group having 1 to 5 carbon atoms, an alkenylene group having 2 to 5 carbon atoms, an alkynylene group having 2 to 5 carbon atoms, or a single bond; b, c and d each independently represent 0 or 1, and satisfy b+c+d≧1; in the bond of $R^5$ with ring A, ring B, or ring C, each ring does not bond directly to an alkenyl group, and in the bond of $R^6$ with ring D, the ring does not bond directly to an alkenyl group;

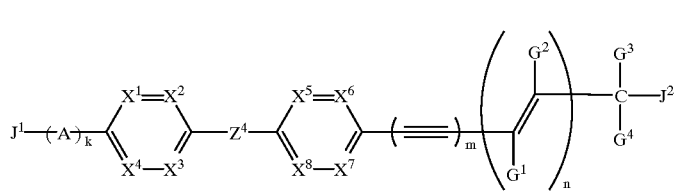

(4)

in the formula (4), $J^1$ represents a hydrogen atom, a fluorine atom, a cyano group, or a $J^3(O)m^1$ (where $J^3$ represents an alkyl group having 1 to 12 carbon atoms, an alkenyl group having 2 to 12 carbon atoms, or an alkynyl group having 2 to 12 carbon atoms, which may be substituted by fluorine, and $m^1$ represents 0 or 1); $J^2$ represents a hydrogen atom or an alkyl group having 1 to 12 carbon atoms, an alkenyl group having 2 to 12 carbon atoms, or an alkoxyalkyl group having 2 to 16 carbon atoms; A represents

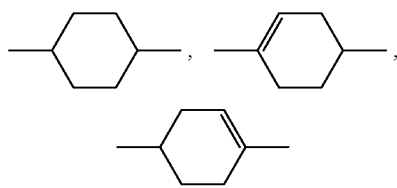

k, m and n represent 0 or 1, but m≠n; $X^1$ to $X^8$ each independently represent CH or CF; $G^1$ to $G^4$ each independently represent a hydrogen atom or a fluorine atom; and $Z^4$ represents —C≡C— or —C≡C—C≡C— (provided that when n=0, $Z^4$ is —C≡C—).

According to the present invention, a liquid crystal composition is provided further comprising at least kind of a compound represented by the formula (5) and/or a compound represented by the formula (6).

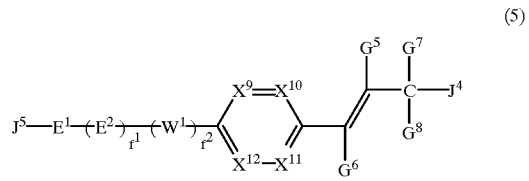

(5)

wherein in the formula (5), $X^9$ to $X^{12}$ each independently represent CH or CF; $J^4$ represents a hydrogen atom, a fluorine atom, a cyano group, an alkyl group having 1 to 12 carbon atoms, an alkenyl group having 2 to 12 carbon atoms, an alkoxy group having 1 to 12 carbon atoms, an alkenyloxy group having 2 to 12 carbon atoms, an alkynyloxy group having 3 to 12 carbon atoms, or an alkoxyalkyl group having 2 to 12 carbon atoms, which may be substituted by fluorine; $J^5$ represents a hydrogen atom, a fluorine atom, a cyano group, or a $J^6$—(O)m$^2$ (where m$^2$ is 0 or 1, and $J^6$ represents an alkyl group having 1 to 12 carbon atoms, an alkenyl group having 2 to 16 carbon atoms, and an alkynyl group having 3 to 16 carbon atoms, which may be substituted by fluorine); $E^1$ and $E^2$ each independently represents

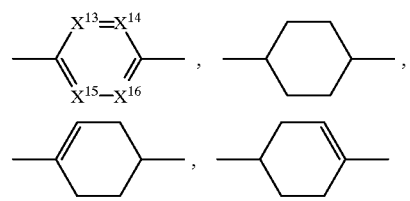

(where $X^{13}$ to $X^{16}$ each independently represent CH or CF); $W^1$ represents —C$_2$H$_4$—, —CH$_2$O—, or —OCH$_2$—; $f^1$ and $f^2$ each independently represent 0 or 1, but will not be 1 at the same time; also when $f^1$ is 1, at least one of $E^1$ or $E^2$ is

and $G^5$ to $G^8$ each independently represent a hydrogen atom or a fluorine atom),

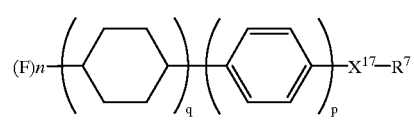

(6)

in the formula (6), $R^7$ represents an alkyl group having 1 to 10 carbon atoms, and a hydrogen atom on the benzene ring in the formula (6) may be substituted by a fluorine atom; n, p and q each independently represent 1 or 2; and $X^{17}$ represents trans—CH=CH— or an ethynyl group (provided that when n is 1, $X^{17}$ may also be —CH$_2$—CH$_2$—).

Furthermore, according to the present invention, a liquid crystal device having the above liquid crystal composition between a pair of electrode substrates is provided.

The present invention is explained in detail below.

Phenylacetylene compound of the present invention is a compound represented by the above general formula (1). In the formula (1), $A^1$ to $A^{12}$ each independently represent a hydrogen atom, a fluorine atom, or an alkyl group having 1 to 10 carbon atoms, and at least one is an alkyl group (provided that, in $A^1$ to $A^{12}$, the cases are excluded where both of A¹ and A² are methyl groups at the same time, while the others are hydrogen atoms, and where both of A⁷ and A¹² are methyl groups at the same time, while the others are hydrogen atoms). At least one of A¹ to A¹² is an alkyl group, and preferably, at least one selected from the group consisting A⁴, A⁵, A⁹ and A¹⁰ is an alkyl group.

In the formula (1) and (2), R¹ and R² each independently represent a hydrogen atom, a fluorine atom, a cyano group, a 4-R³-(cycloalykyl) group, a 4-R³-(cycloalkenyl) group, or a R⁴—(O)$_q$ group (where R³ represents a hydrogen atom, a linear or branched alkyl group having 1 to 12 carbon atoms which may be substituted by fluorine, a linear or branched alkenyl group having 2 to 12 carbon atoms which may be substituted by fluorine, or a linear or branched alkynyl group having 2 to 12 carbon atoms which may be substituted by a fluorine atom, and R⁴ represents a linear or branched alkyl group having 1 to 12 carbon atoms which may be substituted by a fluorine atom, a linear or branched alkenyl group having 2 to 12 carbon atoms which may be substituted by a fluorine atom, or a linear or branched alkynyl group having 2 to 12 carbon atoms which may be substituted by a fluorine atom; and q represents 0 or 1).

Concrete examples of R1 and R2 include: a hydrogen atom; a fluorine atom; alkyl groups, such as methyl group, ethyl group, propyl group, butyl group, pentyl group, hexyl group, heptyl group, octyl group, nonyl group, decyl group, undecyl group, and dodecyl group, and fluorinated alkyl groups thereof (for example, trifluoromethyl group); alkenyl groups, such as ethenyl group, propenyl group, butenyl group, pentenyl group, hexenyl group, heptenyl group, octenyl group, nonenyl group, decenyl group, undecenyl group, and dodecenyl group, and fluorinated alkenyl groups thereof; alkynyl groups, such as propynyl group, butynyl group, pentynyl group, hexynyl group, heptynyl group, octynyl group, nonynyl group, decynyl group, and dodecynyl group, and fluorinated alkynyl groups thereof; alkoxy groups, such as methoxy group, ethoxy group, propoxy group, butoxy group, pentyloxy group, hexyloxy group, octyloxy group, nonyl oxy group, decyloxy group, undecyloxy group, and dodecyl oxy group, fluorinated alkoxy groups thereof (for example, methoxy group substituted by 1–3 fluorine atoms, ethoxy group substituted by 1–5 fluorine atom); alkenyloxy groups, such as vinyl oxy group, propenyloxy group, butenyloxy group, pentenyloxy group, hexenyloxy group, heptenyloxy group, octenyloxy group, nonenyloxy group, and decenyloxy group, and fluorinated alkenyloxy groups thereof; alkynyloxy groups, such as propionyloxy group, butynyloxy group, pentynyloxy group, hexynyloxy group, heptynyloxy group, octynyloxy group, nonynyloxy group, decynyloxy group, undecynylloxy group, and dodecynyloxy group, fluorinated alkynyloxy groups thereof; alkoxyalkyl groups, such as methoxymethyl group, ethoxymethyl group, propoxymethyl group, butoxymethyl group, pentyloxy methyl group, hexyloxymethyl group, heptyloxymethyl group, octyloxymethyl group, nonyloxymethyl group, decyloxymethyl group, methoxyethyl group, ethoxyethyl group, propoxyethyl group, butoxyethyl group, pentyloxyethyl group, hexyloxyethyl group, heptyloxyethyl group, octyloxyethyl group, nonyloxyethyl group, decyloxyethyl group, methoxypropyl group, ethoxypropyl group, propoxypropyl group, butoxypropyl group, pentyloxypropyl group, hexyloxypropyl group, heptyloxypropyl group, octyloxypropyl group, nonyloxypropyl group, methoxybutyl group, ethoxybutyl group, propoxybutyl group, butoxybutyl group, pentyloxybutyl group, hexyloxybutyl group, heptyloxybutyl group, octyloxybutyl group, methoxypentyl group, ethoxypentyl group, propoxypentyl group, butoxypentyl group, pentyloxypentyl group, hexyloxypentyl group, and heptyloxypentyl group, and fluorinated alkoxyalkyl groups thereof; branched alkyl groups, such as 2-methylpropyl group, 2-methylbutyl group, 3-methylbutyl group, and 3-methylpentyl group, and fluorinated branched alkyl groups thereof; branched alkyloxy groups, such as 2-methylpropyloxy group, 2-methylbutyloxy group, 3-methylbutyloxy group, and 3-methylpentyloxy group, and fluorinated branched alkyloxy groups thereof; 4-alkyl-cycloalkyl groups, such as 4-methylcyclohexyl group, 4-ethylcyclohexyl group, 4-propylcyclohexyl group, 4-butylcyclohexyl group, 4-pentylcyclohexyl group, 4-hexylcyclohexyl group, 4-heptylcyclohexyl group, 4-octylcyclohexyl group, 4-nonylcyclohexyl group, and 4-decylcyclohexyl group, and 4-fluoroalkyl-cycloalkyl groups thereof; 4-alkyl-cycloalkenyl groups, such as 4-propylcyclohexenyl group and 4-pentylcyclohexenyl group, and 4-fluoroalkyl-cycloalkenyl groups thereof; a cyano group, etc.

As a concrete examples of phenyl acetylene compound represented by the general formula (1) or (2), compounds having the following formula are exemplified. R1 and R2 are preferably the groups as above-mentioned without being limited to those.

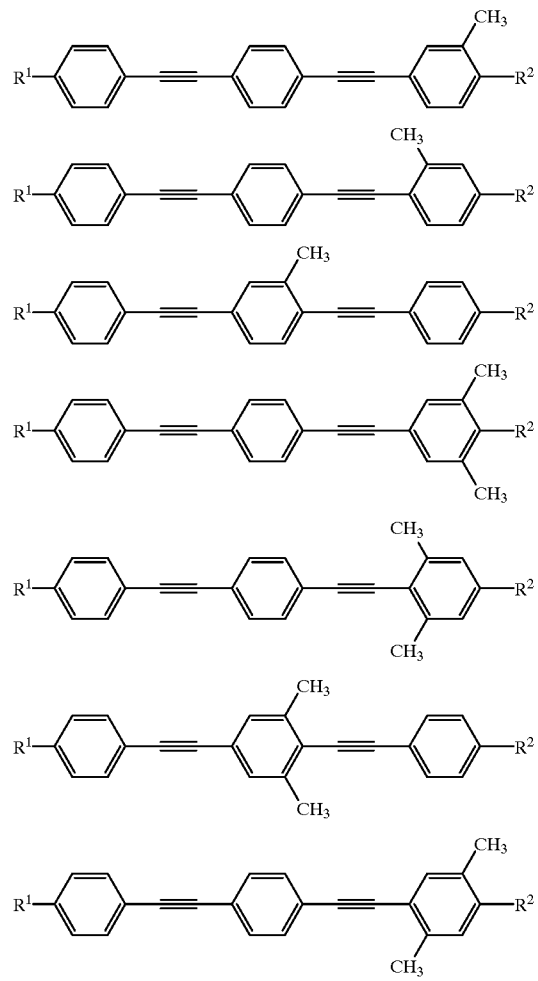

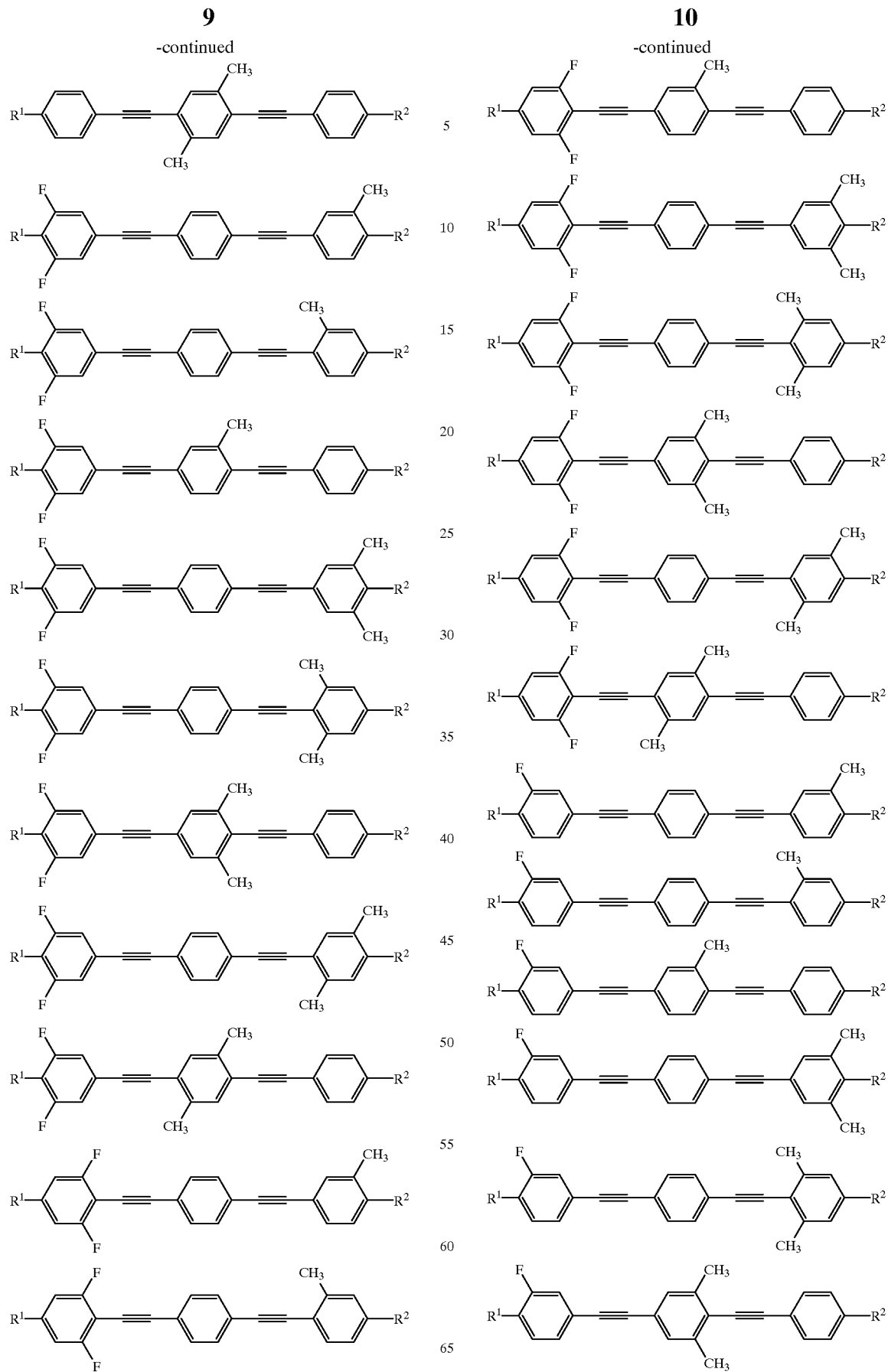

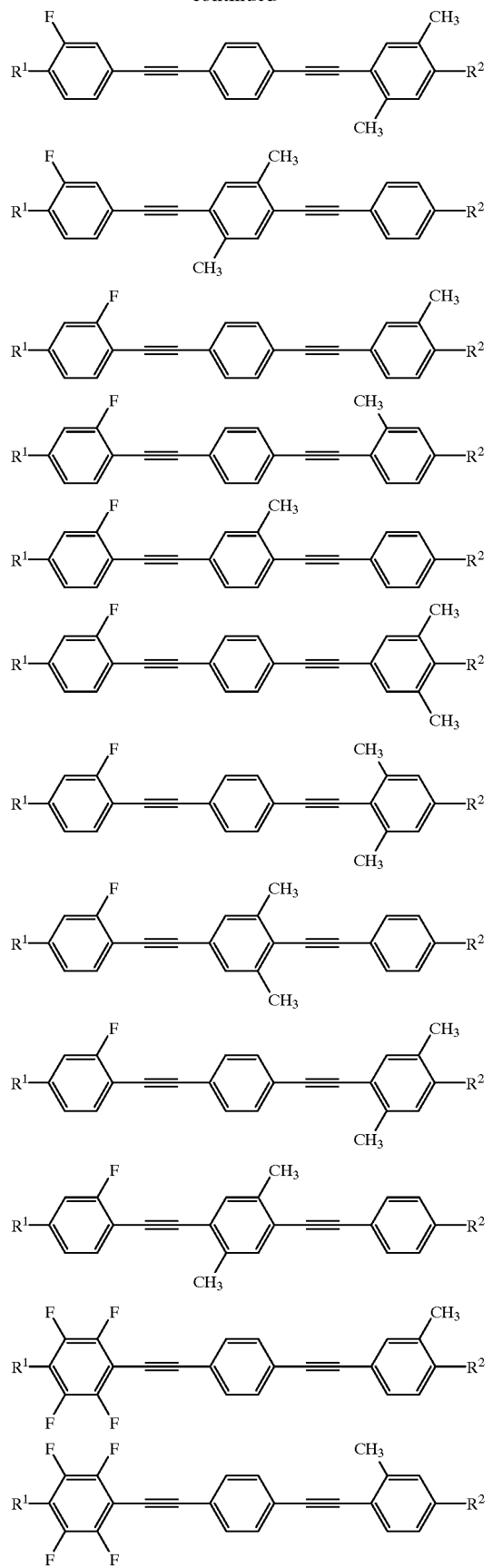
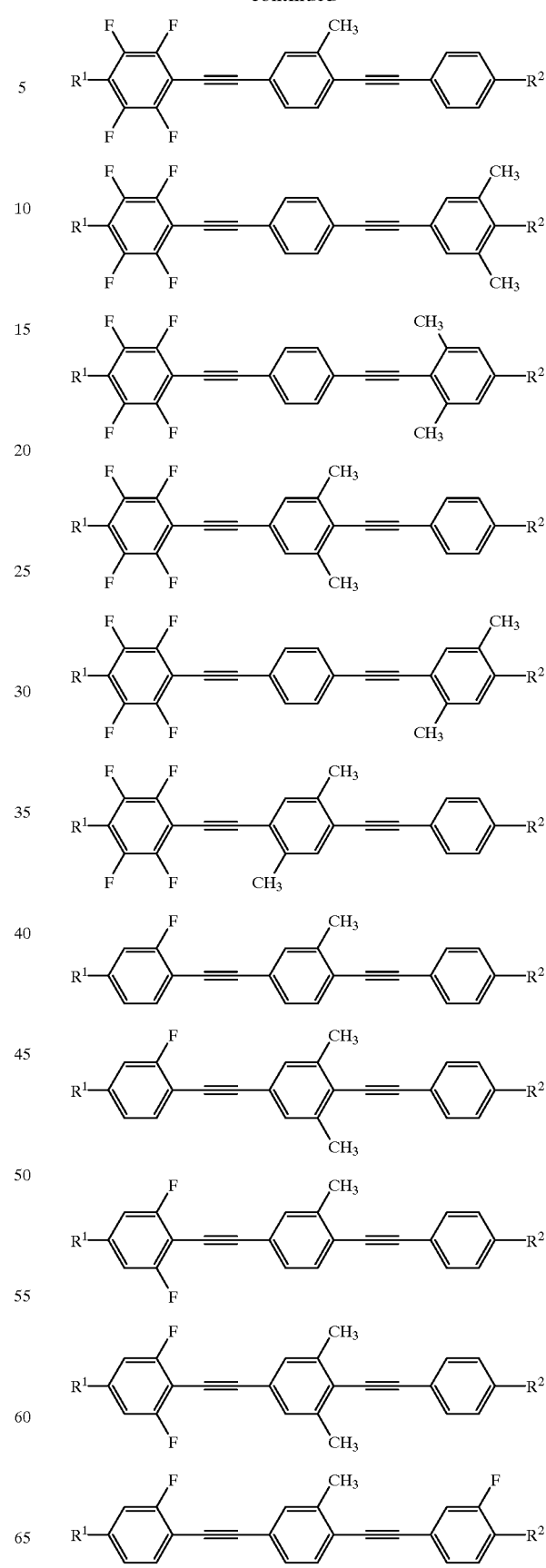

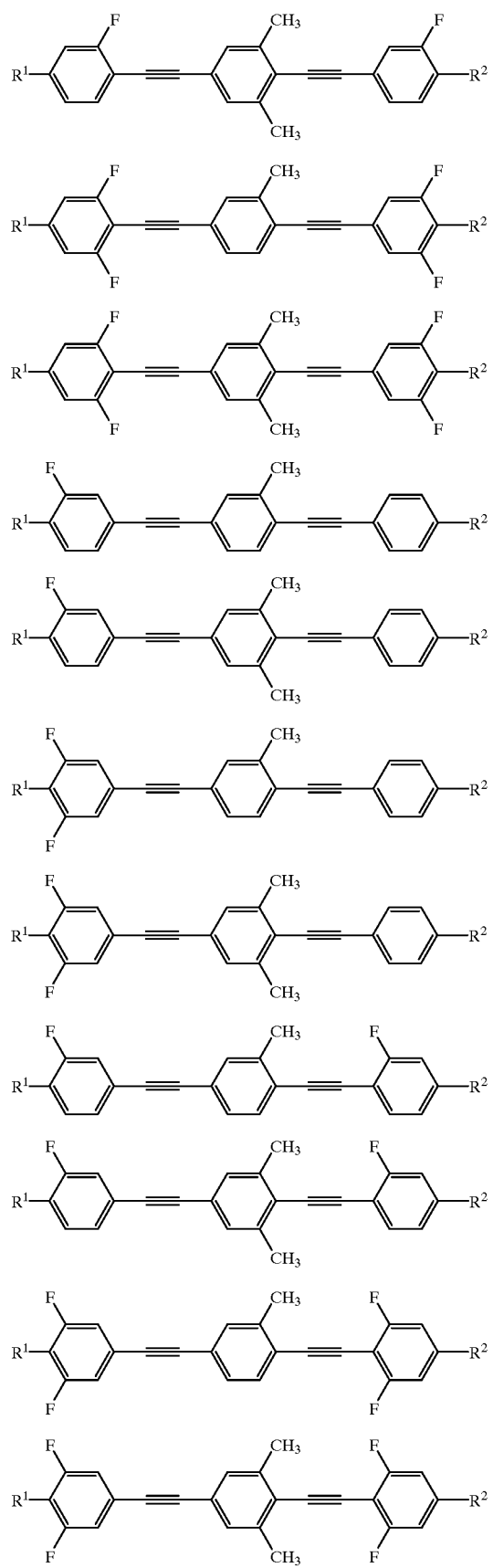
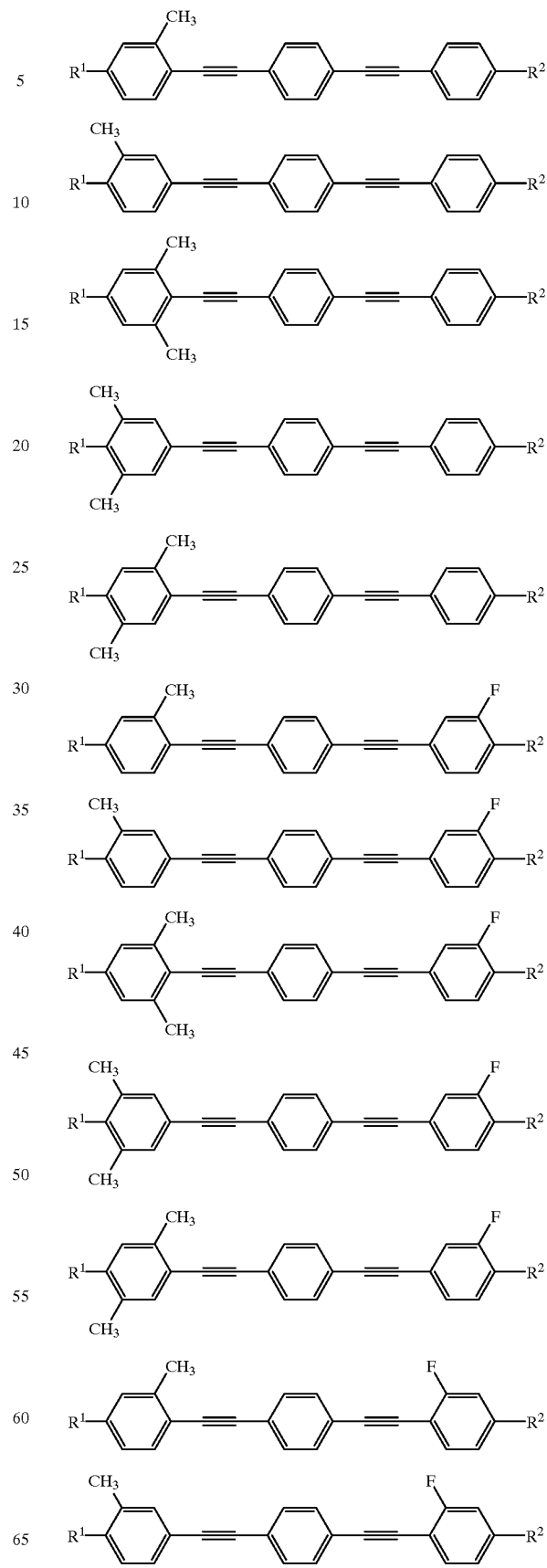

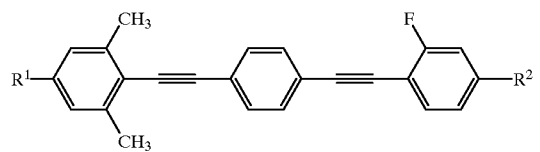
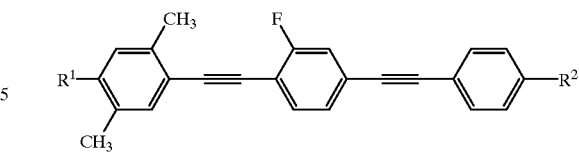
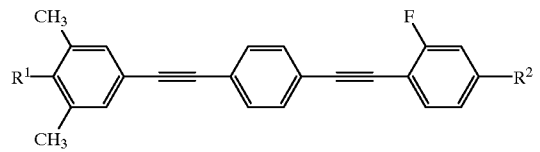
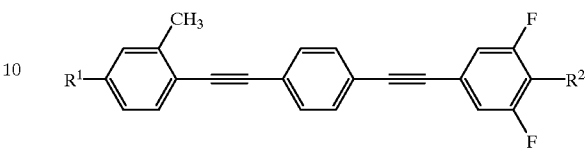
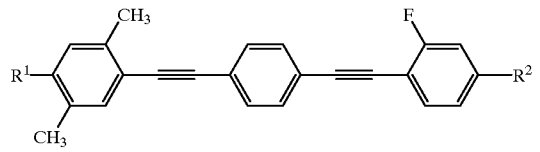
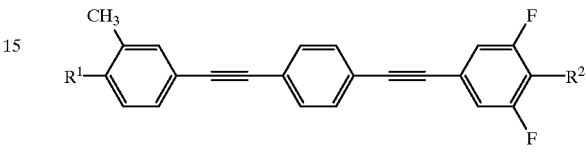
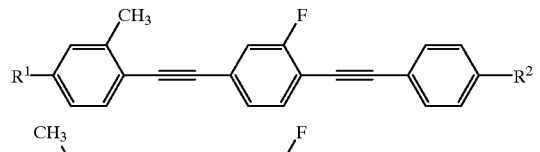
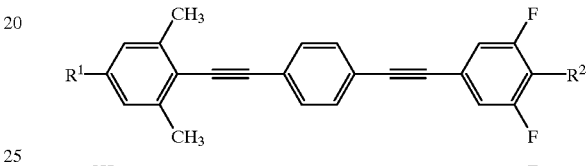
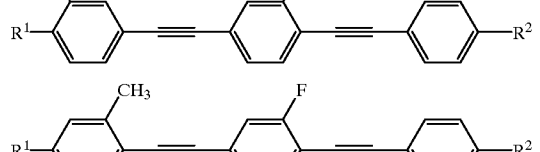
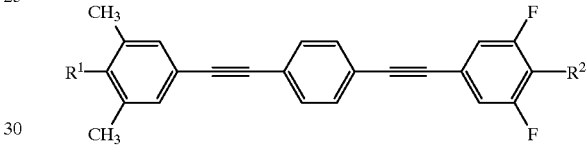
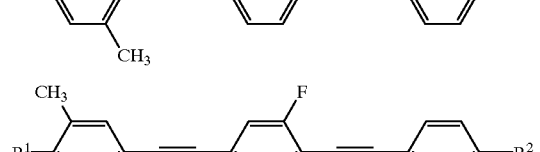
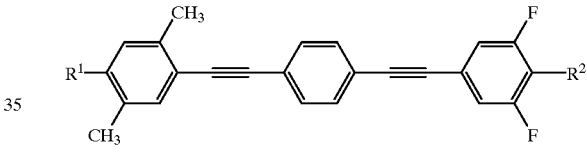
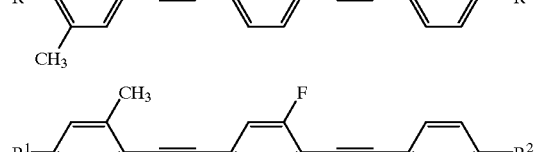
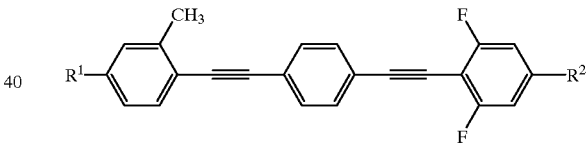
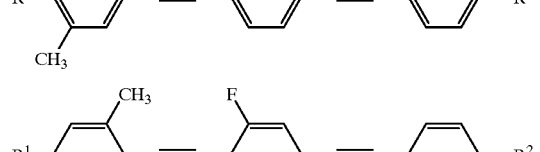
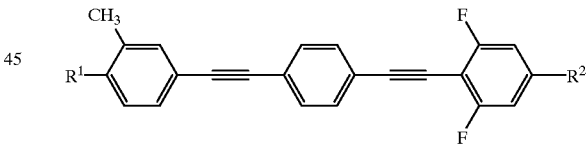
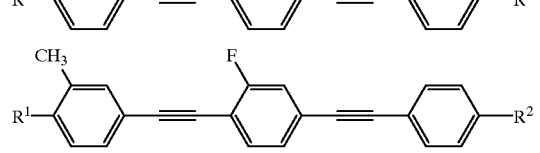
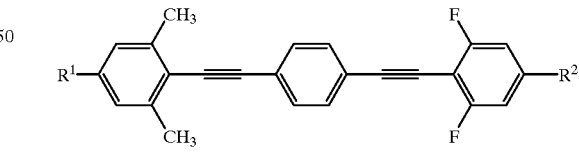
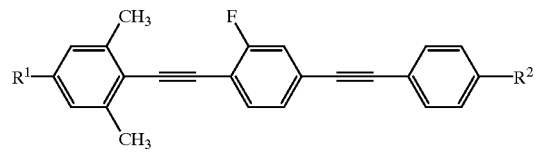
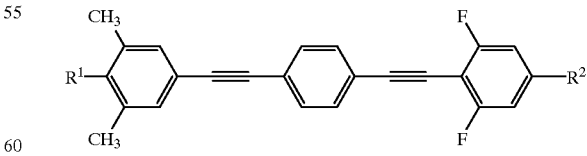
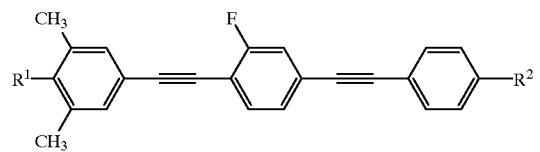
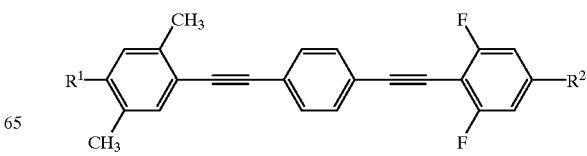

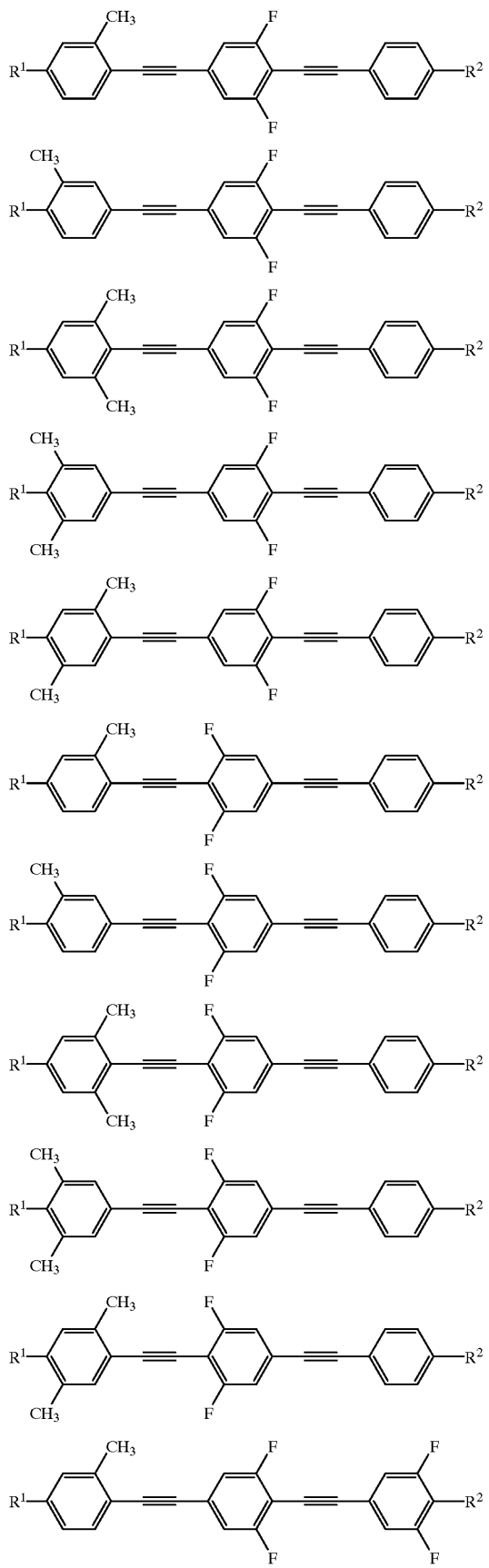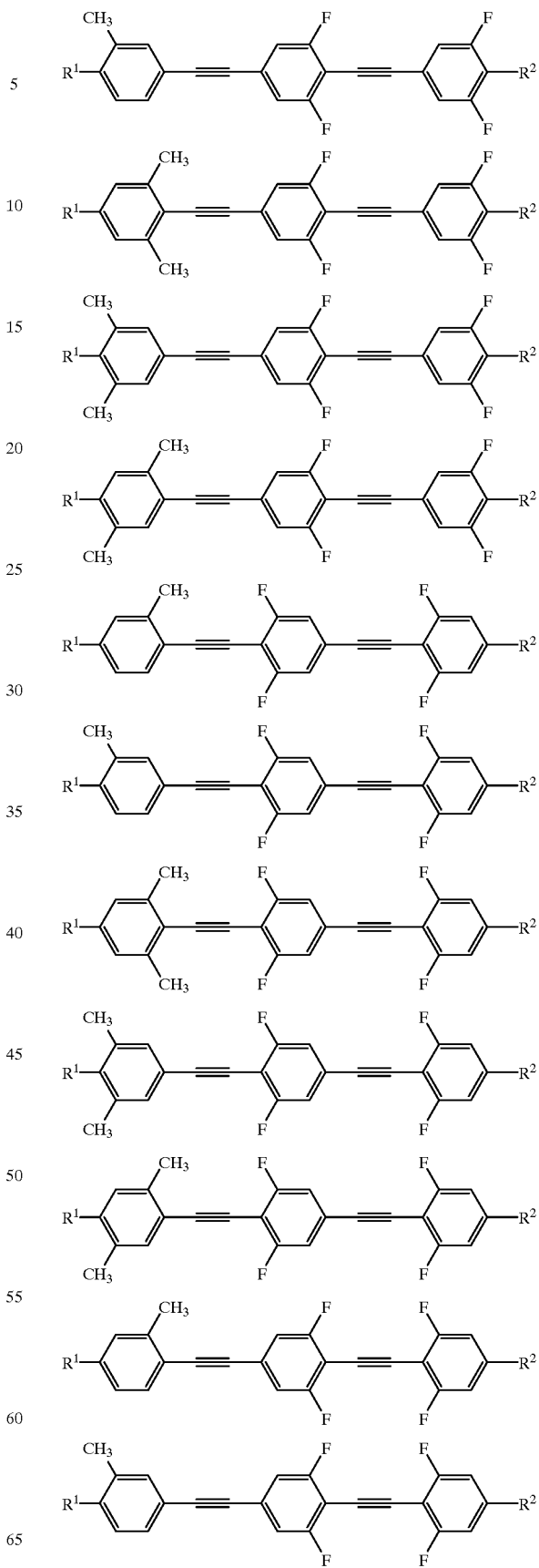

-continued

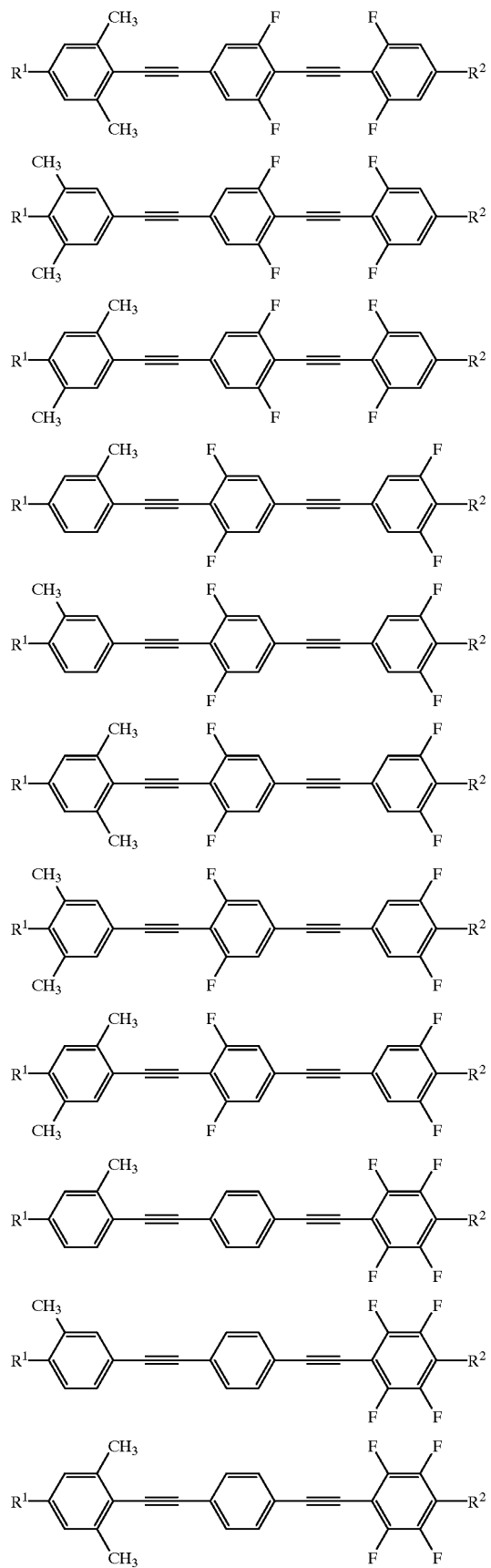

-continued

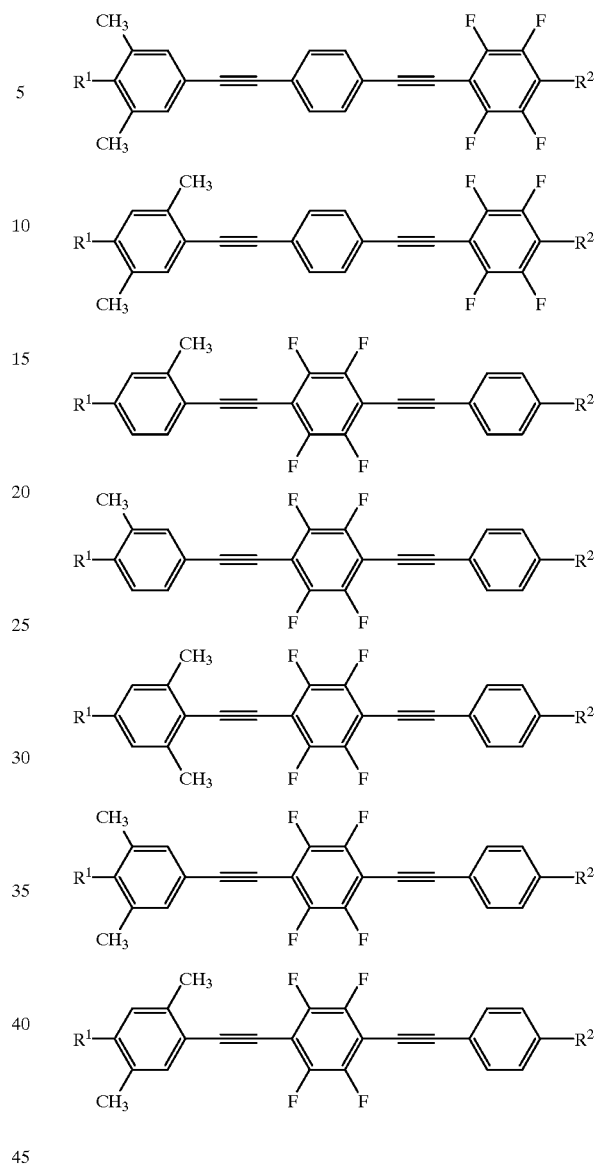

The phenyl acetylene compound of the present invention can be prepared by using conventional organic synthetic methods. For example, it can be obtained by combining the reactions described in, such as "Organic synthesis developed by transition metals" (Jiro Tsuji, published by Kagaku Dojin Co.). Concretely, the compound can be prepared by reacting the compound represented by the general formula (IM-1) and the compound represented by general formula (IM-2) in the presence of copper iodide, palladium catalyst and bases such as triethyl amine.

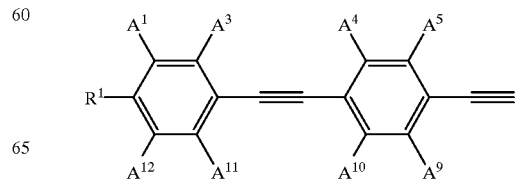

(IM-1)

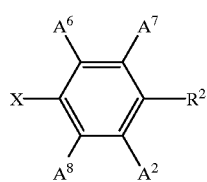
(IM-2)

In the formula (IM-1) and (IM-2), $A^1$–$A^{12}$, and $R^1$ and $R^2$ represent the same meaning as in the general formula (1). X represents I, Br or $OSO_2CF_3$.

The compound represented by the general formula (IM-1) can be prepared, for example, after carrying out coupling the compound represented by the general formula (M-1) with the compound represented by the general formula (M-2), butyne-2-ol is reacted in the presence of copper iodide, palladium catalyst, and bases such as triethyl amine, and further reacted under existence of bases such as potassium hydroxide.

(M-1)

(M-2)

In the formula (M-1) and (M-2), $A^1$, $A^3$–$A^5$, $A^9$–$A^{12}$, and $R^1$ represent the same meaning as the compound in general formula (1).

In the reaction for obtaining a phenyl acetylene compound (1) from the compoundss represented by the general formula (IM-2) and (IM-1), the amount of compound (IM-2) is usually 0.3 to 10 equivalents to that of compound (IM-1), and suitably, 0.5–2 equivalents.

As a palladium catalyst used for the above reaction, palladium chloride, palladium acetate, palladium/carbon, triphenylphosphine palladium complex (for example, tetrakistriphenylphosphine palladium, dichloroditriphenylphosphine palladium), etc. are used. The amount of palladium catalyst is in the range of 0.001 to 0.1 equivalent to the compound (IM-2).

The amount of copper iodide (I) added as an additive is 0–0.1 equivalents to the compound (IM-2).

Examples of the basic substance used for this reaction include: carbonate, carboxylate, alkoxide and hydroxide of alkali metal; organic bases such as triethyl amine, diisopropylethyl amine, tri-n-butyl amine, tetramethylethylenediamine, dimethylaniline, N-methylmorpholine, and N-methyl piperidine, and tertiary amines such as triethylamine is preferable.

The amount of basic substance is 1 to 20 equivalents to compound (IM-2).

Acetonitrile, tetrahydrofuran, dimethylformamide, hexamethylphosphoramide, N-methylpyrrolidone, benzene, toluene, etc. can also be used as a reaction solvent, if necessary.

Concrete examples of general formula (IM-1) are shown below.

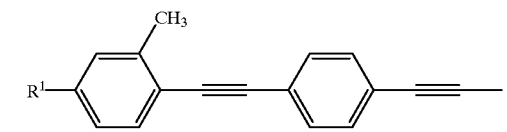
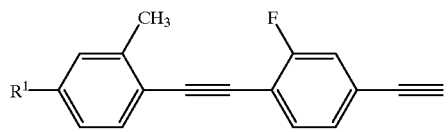
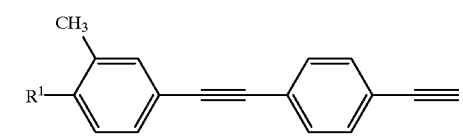
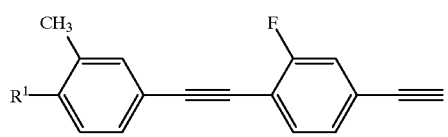
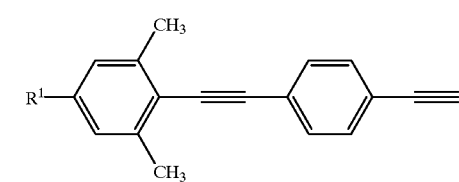
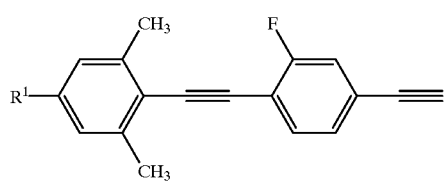

-continued
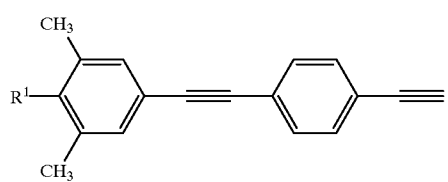 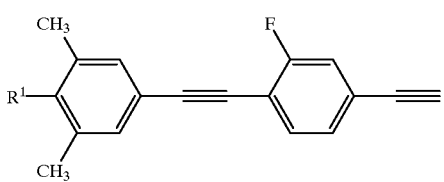
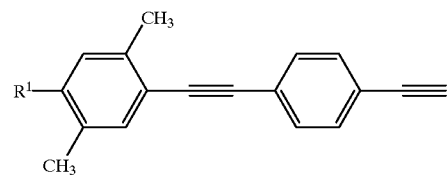 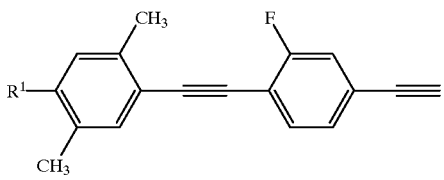
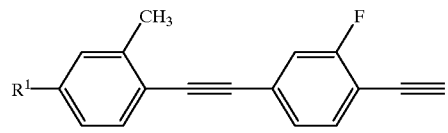 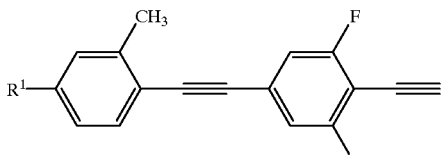
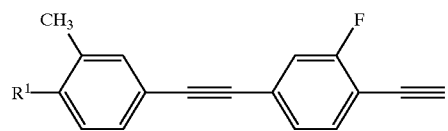 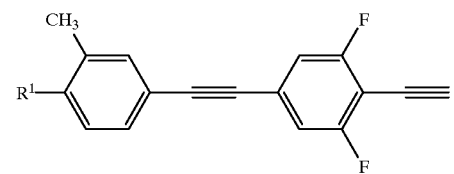
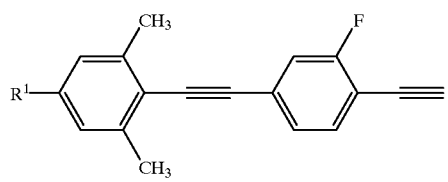 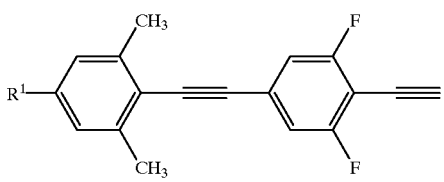
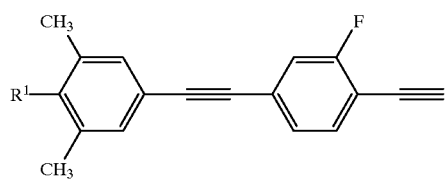 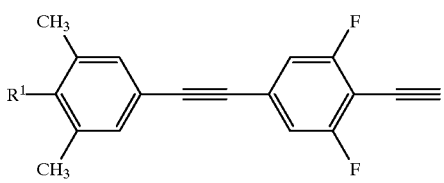
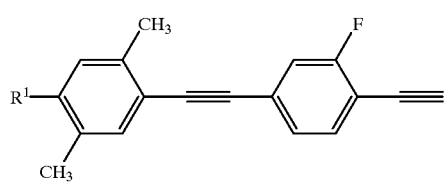 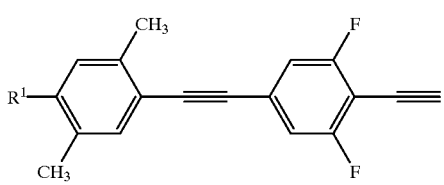
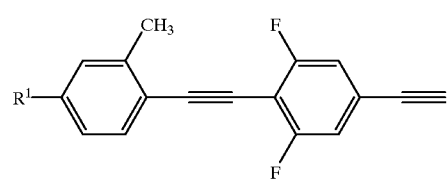 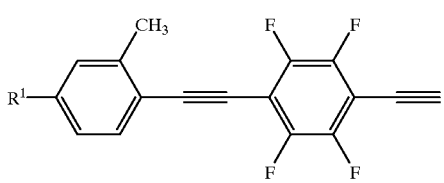
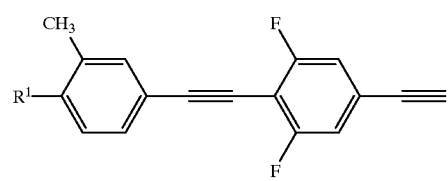 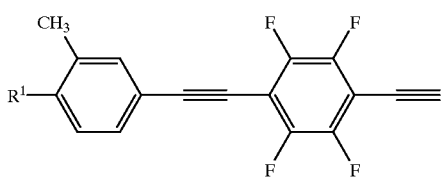

-continued
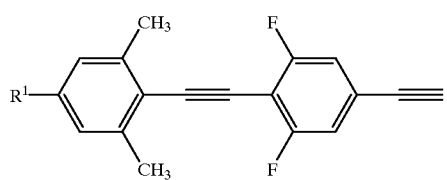
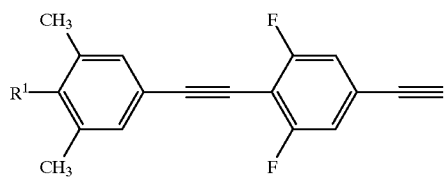
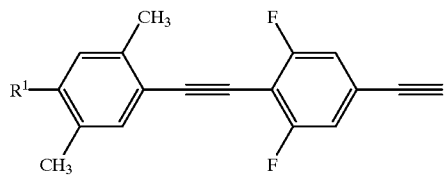
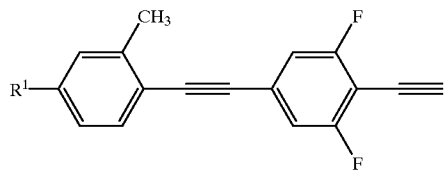
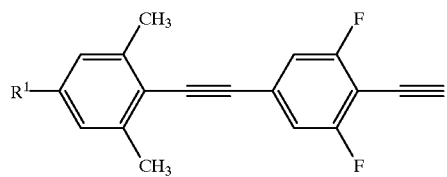
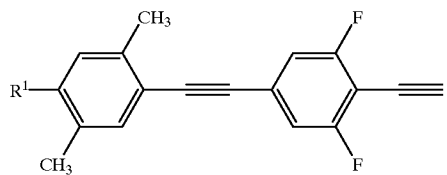
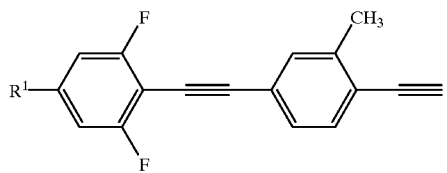
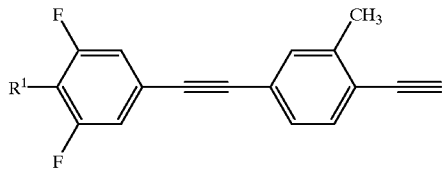
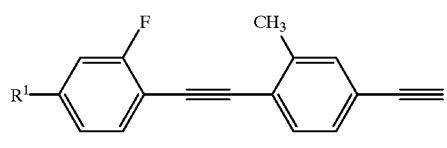
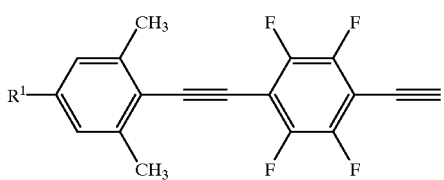
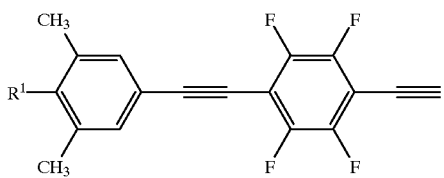
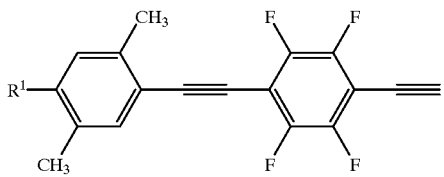
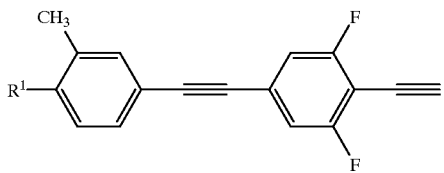
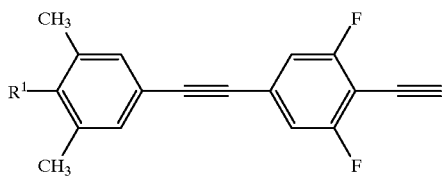
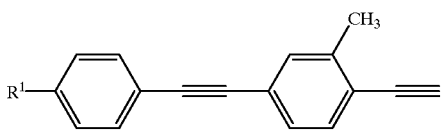
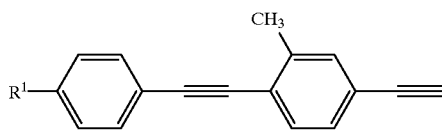
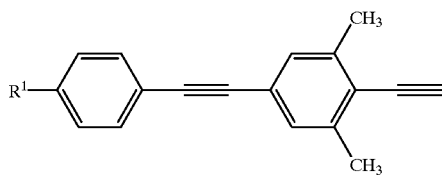
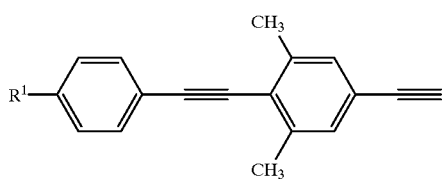

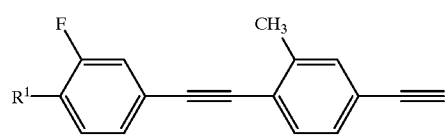
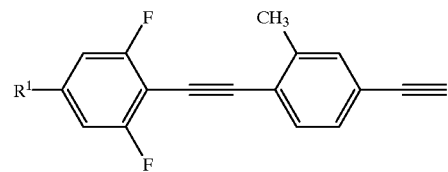
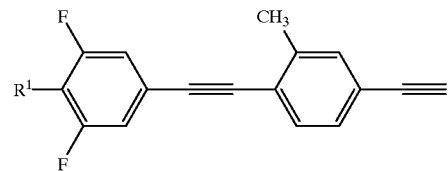
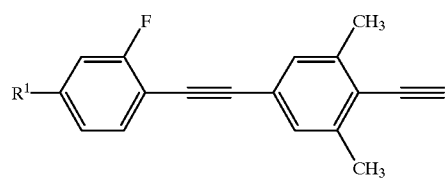
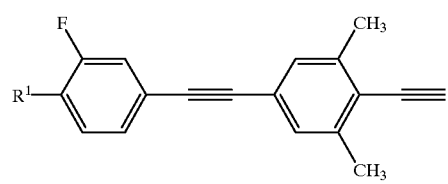
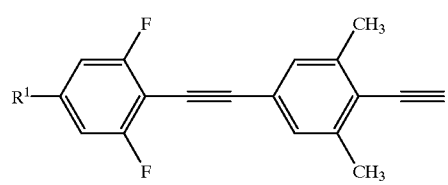
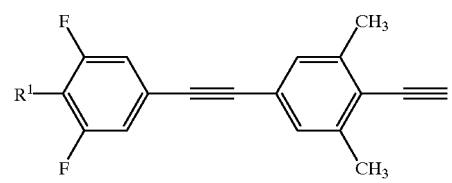
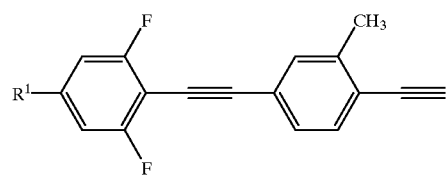
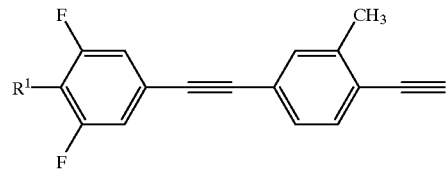
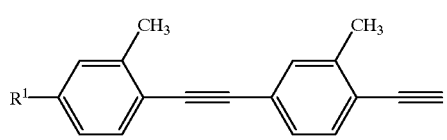
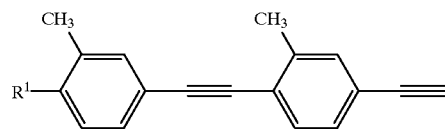
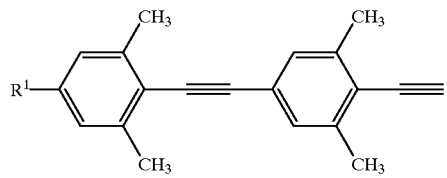
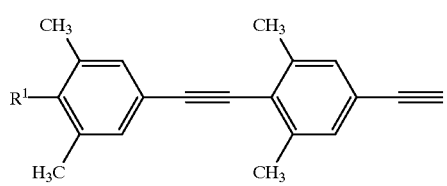
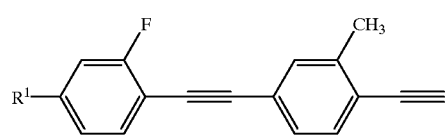
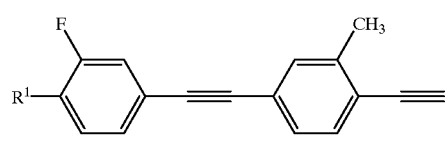
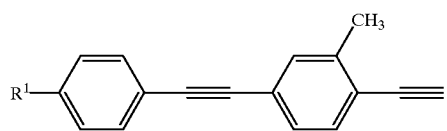
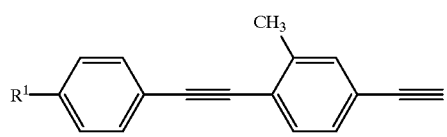
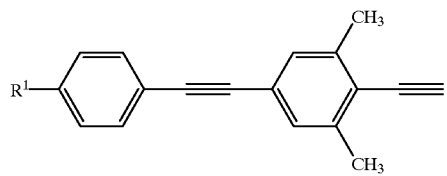

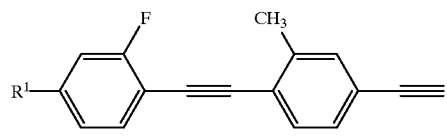
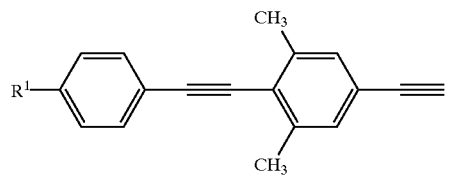
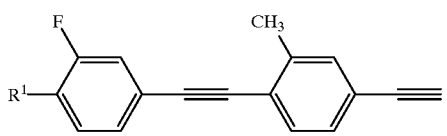
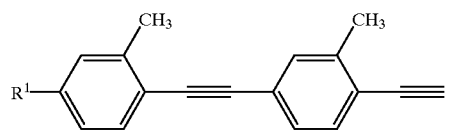
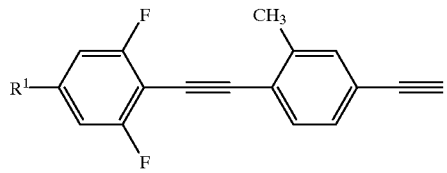
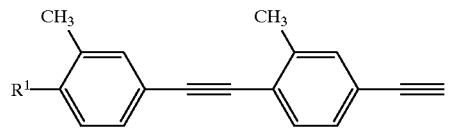
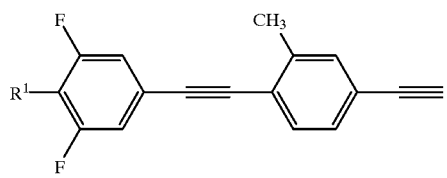
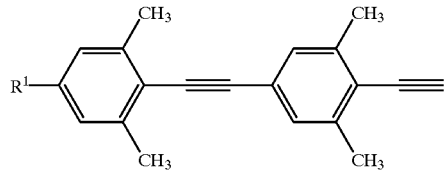
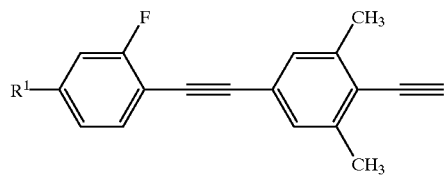
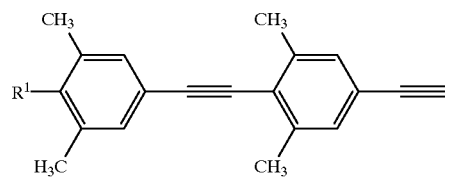
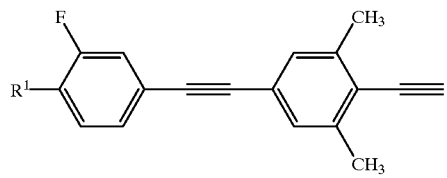
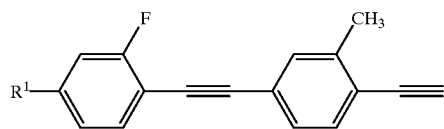
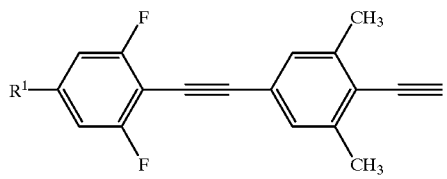
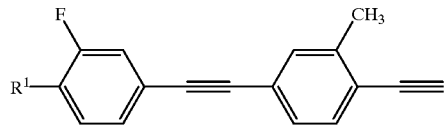
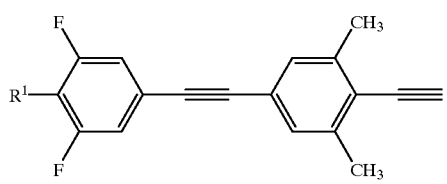
Concrete examples of $R^1$ represent the same as the concrete examples of general formula (1).
The compound represented by the general formula (1) can be prepared by reacting the compound represented by general formula (IM-3) and the compound represented by the general formula (IM-4) in the presence of copper iodide, palladium catalyst, and a base such as triethylamine.

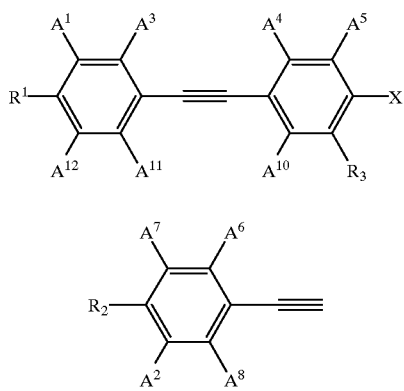

(IM-3)

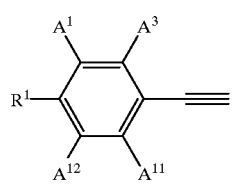

(IM-4)

In the Formulas (IM-3) and (IM-4), $A^1$–$A^{12}$, $R^1$ and $R^2$ represent the same meaning as in the general formula (1). X represents I, Br, or $OSO_2CF_3$. The compound represented by the general formula (IM-3) can be prepared by coupling the compound represented by the general formula (M-3) and the compound represented by general formula (M-4), for example.

(M-3)

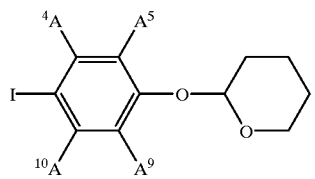

(M-4)

In the reaction for obtaining a phenylacetylene compound (1) from the compound represented by the general formula (IM-3) and the compound represented by general formula (IM-4), the amount of compound (IM-3) is usually 0.3 to 10 equivalent amount to the compound (IM-4), and preferably, 0.5–2 equivalent.

As a palladium catalyst used for the above reaction, the same catalyst used for the reaction of (IM-1) and (IM-2) can be used. The amount of the palladium catalyst used is in the range of 0.001 to 0.1 equivalent amount to the raw material compound (IM-4).

The amount of copper iodide (I) used as an additive is 0–0.1 equivalent to the raw material compound (IM-2).

Examples of a basic substance used for this reaction include: carbonate, carboxylate, alkoxide and hydroxide of alkali metal; organic bases, such as triethylamine, diisopropylethylamine, tri-nbutylamine, tetramethyl ethylenediamine, dimethyl aniline, N-methylmorpholine, and N-methyl piperidine. Among them, tertiary amines, such as triethyl amine are preferable.

The amount of basic substance is 1 to 20 equivalent to the compound (IM-4). Acetonitrile, tetrahydrofuran, dimethylformamide, hexamehylphosphoramide, N-methylpyrrolidone, benzene, toluene, etc. can also be used as a reaction solvent, if necessary.

Concrete examples of general formula (IM-3) are shown below.

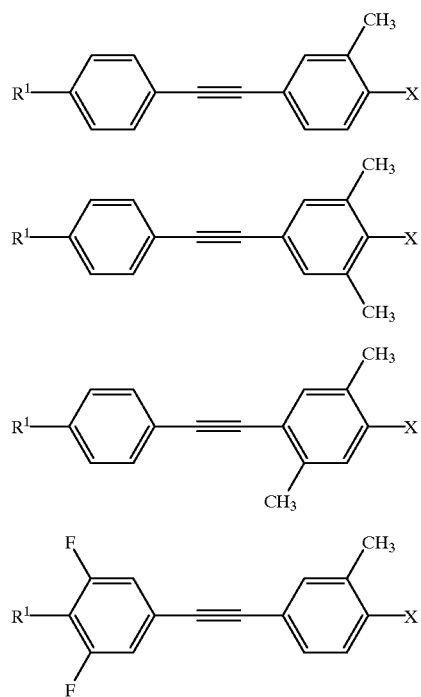

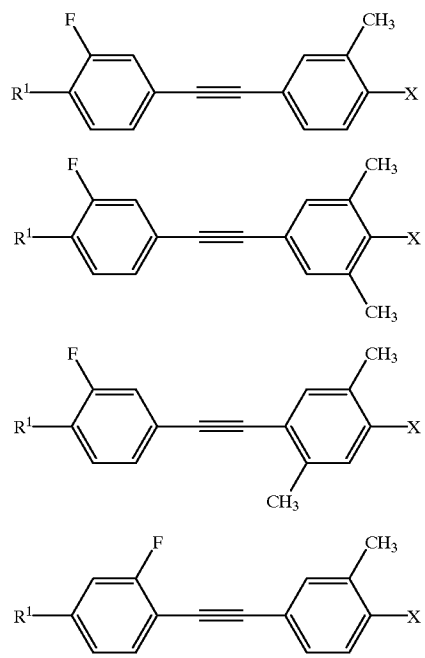

-continued
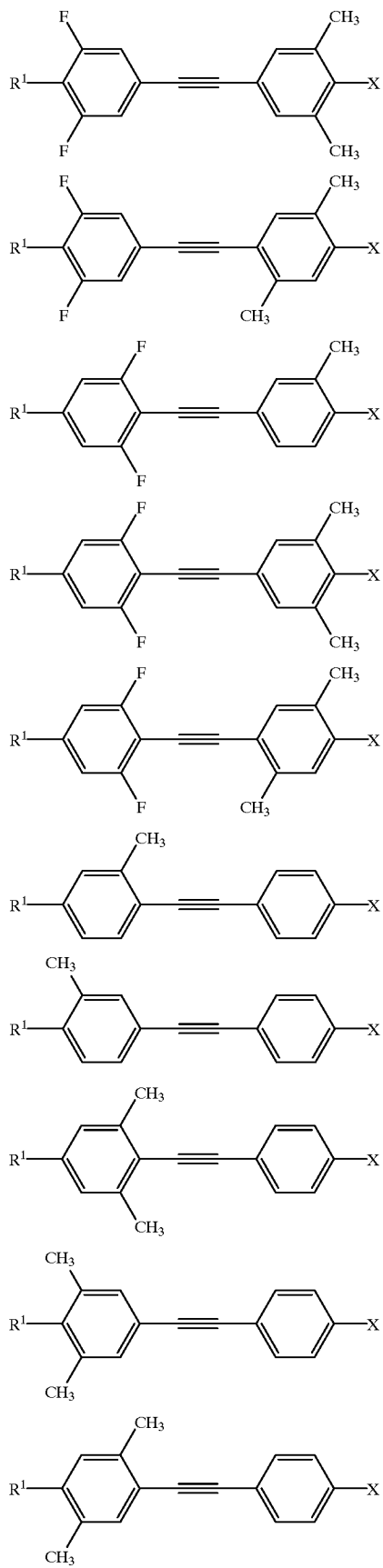
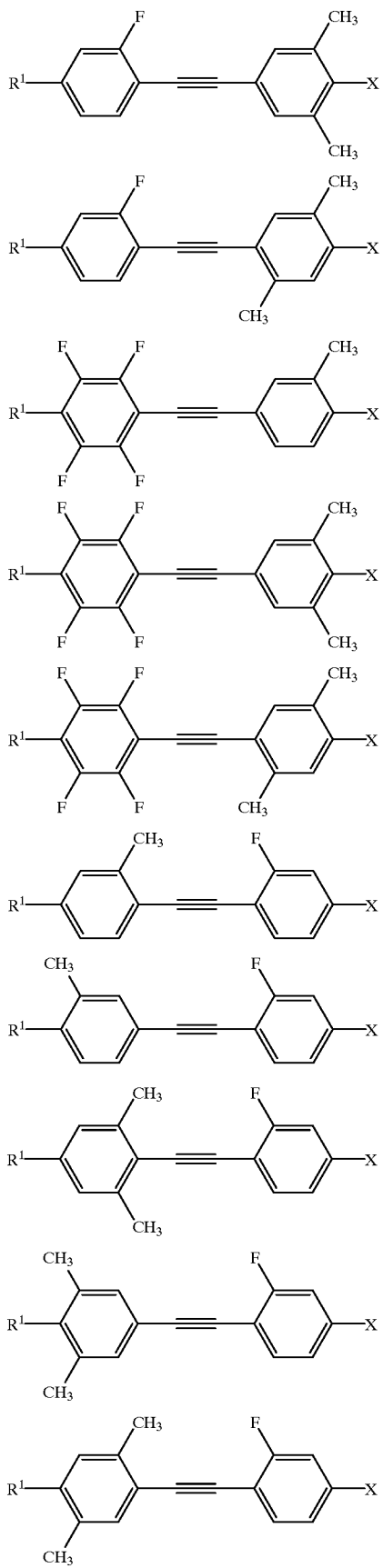

-continued
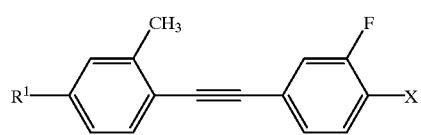
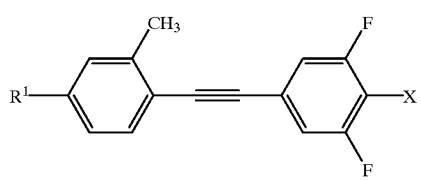
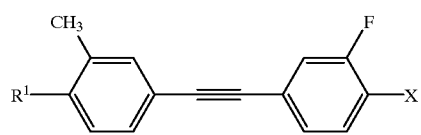
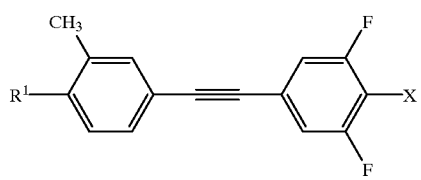
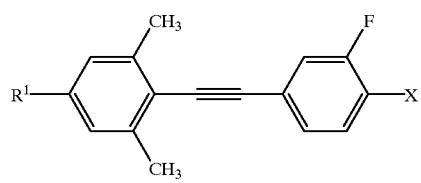
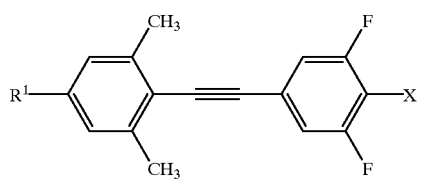
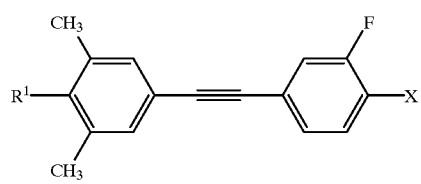
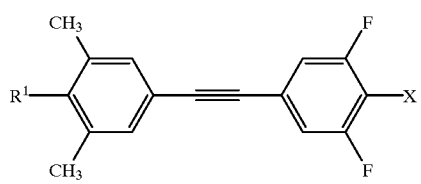
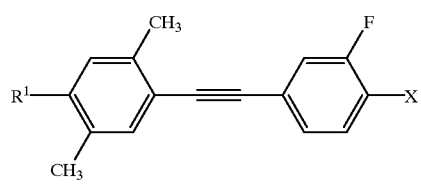
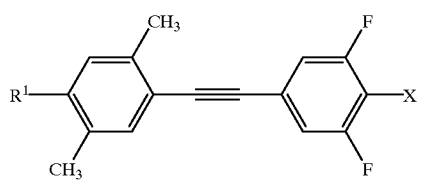
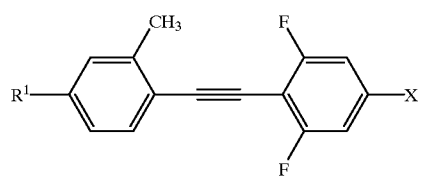
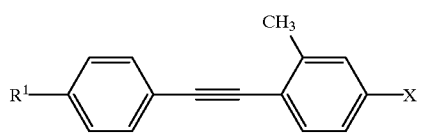
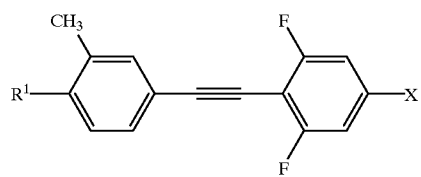
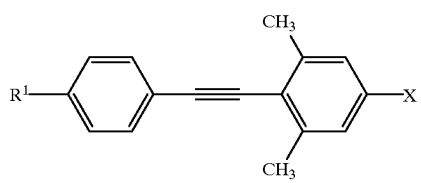
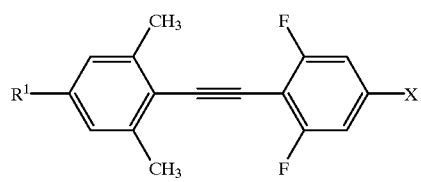
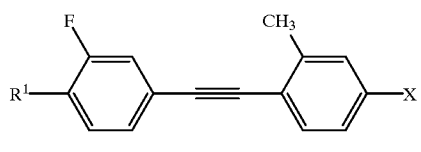
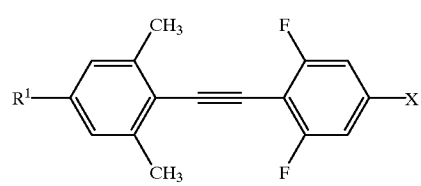
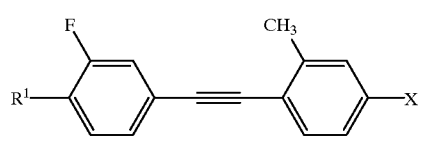

-continued
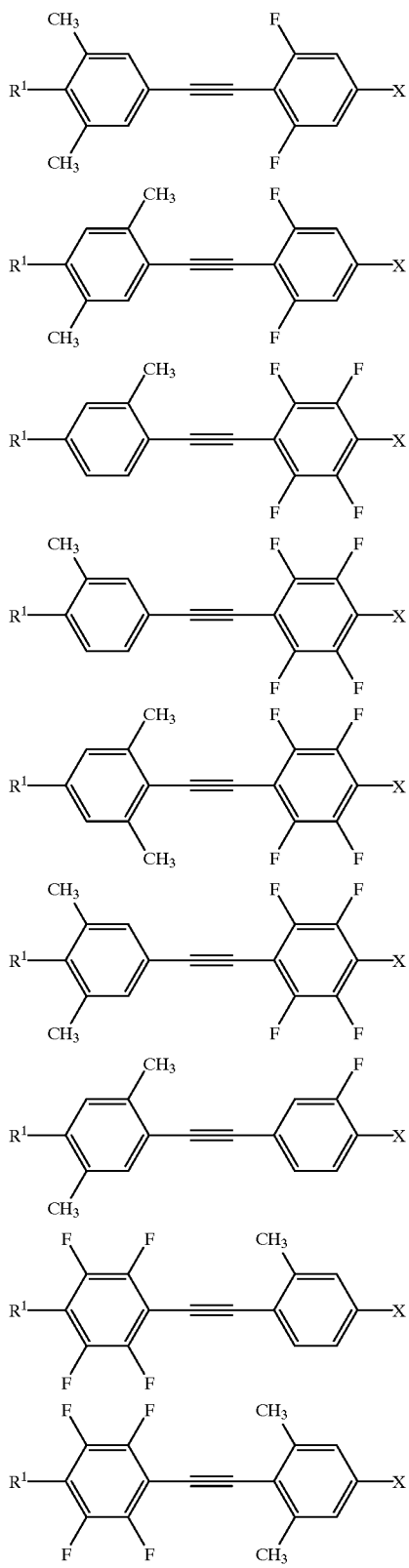
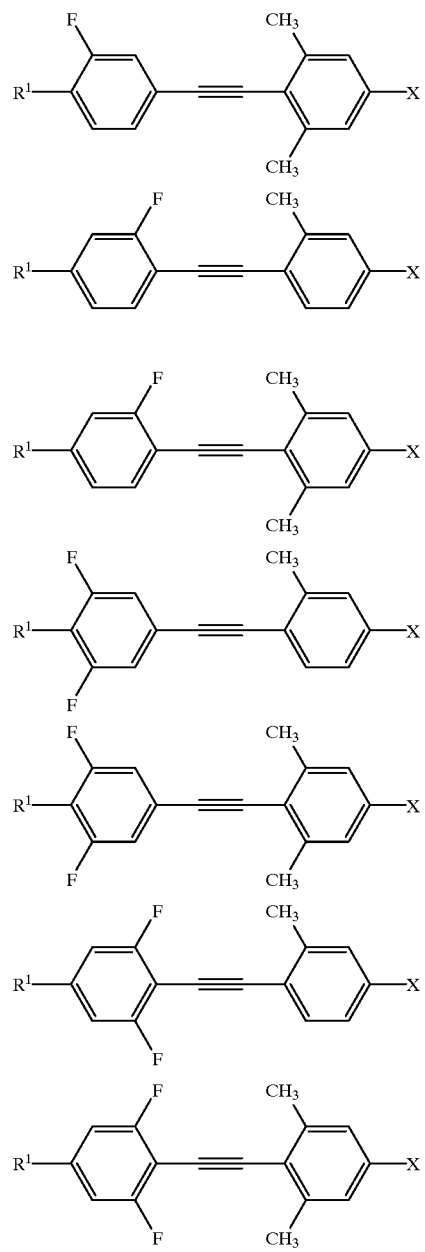
Examples of $R^1$ represent the same as the examples in the general formula (1). X represents I, Br and $OSO_2CF_3$.
In the compound shown by the above formula (3) used for liquid crystal composition of the present invention, ring A, ring B, ring C and ring D represent, each independently, 1,4-phenylene, 1,4-cyclohexylene, 1,4-cyclohexelene, 4,1-cyclohexelene, 2,5-cyclohexelene, 5,2-cyclohexelene, 3,6-cyclohexelene, 6,3-cyclohexelene, 2,5-pyrimidinediyl, 5,2-pyrimidinediyl, 2,5-pyridinediyl, 5,2-pyridinediyl, 2,5-dioxanediyl or 5,2-dioxanediyl. Hydrogen atoms on ring A, ring B, ring C, and ring D may be substituted by fluorine atom.

In the formula (3), $R^5$ and $R^6$ represent a hydrogen atom, a fluorine atom, fluoromethyl group, difluoromethyl group, trifluoromethyl group, fluoromethoxy group, difluoromethoxy group, trifluoromethoxy group, cyano group; alkyl group having 1–12 carbon atoms, alkenyl group having 2–12 carbon atoms, alkoxy group having 1–12 carbon atoms, alkenyloxy group having 2–12 carbon atoms, alkynyloxy group having 3–12 carbon atoms, alkoxyalkyl group having 2–16 carbon atoms, or alkoxyalkenyl group having 3–16 carbon atoms.

Concrete examples of $R^5$ and $R^6$ include: hydrogen atom; fluorine atom; fluoromethyl group; difluoromethyl group; trifluoromethyl group; fluoromethoxy group; difluoromethoxy group; trifluoromethoxy group; cyano group; alkyl groups, such as methyl group ethyl group, propyl group, butyl group, pentyl group, hexyl group, heptyl group, octyl group, nonyl group, decyl group, undecyl group, and dodecyl group; alkenyl groups, such as ethenyl group, propenyl group, butenyl group, pentenyl group, hexenyl group, heptenyl group, octenyl group, nonenyl group, decenyl group, undecenyl group, and dodecenyl group; alkoxy groups, such as methoxy group, ethoxy group, propoxy group, butoxy group, pentyloxy group, hexyloxy group, heptyloxy group, octyloxy group, nonyloxy group decyloxy group, undecyloxy group, and dodecyloxy group; alkenyloxy group, such as vinyl oxy group, propenyloxy group, butenyloxy group, pentenyloxy group, hexenyloxy group, heptenyloxy group, octenyloxy group, nonenyloxy group, and decenyloxy group; alkynyloxy groups, such as propynyloxy groups, butynyloxy group, pentynyloxy group, hexynyloxy group, heptynyloxy group, octynyloxy group nonynyloxy group, decynyloxy group, undecynylloxy group, and dodecynyloxy group; alkoxyalkyl groups, such as methoxymethyl group, ethoxymethyl group, propoxymethyl group, butoxymethyl group, pentyloxymethyl group, hexyloxymethyl group, heptyloxymethyl group, octyloxymethyl group, nonyloxy methyl group, decyloxymethyl group, methoxyethyl group, ethoxyethyl group, propoxyethyl group, butoxyethyl group, pentyloxyethyl group, hexyloxyethyl group, heptyloxy ethyl group, octyloxyethyl group, nonyloxyethyl group, decyloxyethyl group, methoxypropyl group, ethoxypropyl group, propoxypropyl group, butoxypropyl group, pentyloxypropyl group, hexyloxypropyl group, heptyloxypropyl group, octyloxypropyl group, nonyloxypropyl group, decyloxypropyl group, methoxybutyl group, ethoxybutyl group, propoxybutyl group, butoxybutyl group, pentyloxybutyl group, hexyloxybutyl group, heptyloxybutyl group, octyloxybutyl group, nonyloxybutyl group, decyloxybutyl group, methoxypentyl group, ethoxypentyl group, propoxypentyl group, butoxypentyl group, pentyloxypentyl group, hexyloxypentyl group, heptyloxypentyl group, octyloxypentyl group, nonyloxypentyl group, decyloxypentyl group.

In the formula (3), $Z^1$, $Z^2$ and $Z^3$ represent each independently —COO—, —OCO—, —OCH$_2$—, —CH$_2$O—, alkylene group having 1–5 carbon atoms, alkenylene group having 2–5 carbon atoms, alkynylene group having 2–5 carbon atoms, or single bond. In the formula (3), b, c and d are 0 or 1 each independently, and b+c+d>=1; in the bond of $R^5$ with ring A, ring B, or ring C, each ring does not bond directly to an alkenyl group, and in the bond of $R^6$ with ring D, the ring does not bond directly to an alkenyl group.

As a compound represented by the formula (3), compounds represented by the following formula (7)–(11) can be exemplified.

The meaning of $R^5$, $R^6$, ring A, ring B, $Z^1$, and b in the formula (7)–(11) is the same as in the formula (3). In the formula, j is 0, 1 or 2; h is 0 or 1, and i is 0, 1 or 2. $B^1$ to $B^{12}$ represent each independently, a hydrogen atom, a fluorine atom and a chlorine atom.

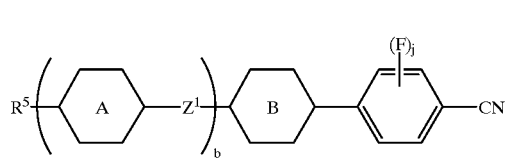

(7)

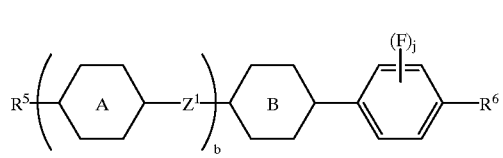

(8)

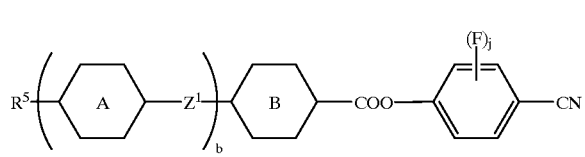

(9)

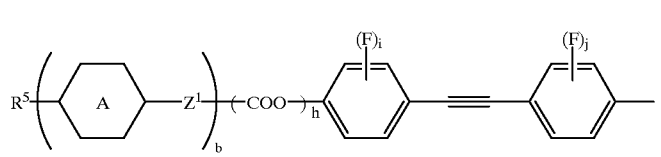

(10)

(11)

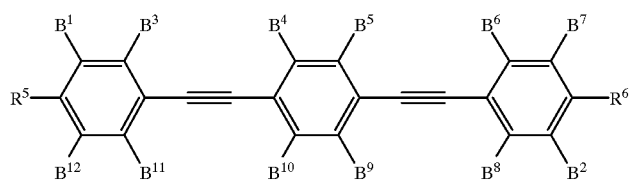

Concrete examples of a compound represented by the formula (3) include, for example, compounds having following formulas, and also include the compounds represented by the above-mentioned formula (7)–(10). In the formula, W represents hydrogen atom or fluorine atom. x represents an integer of 0–3. The ring H represents 1,4-cyclohexylene. The ring G represents 1,4-phenylene, 1,4-cyclohexylene, 1,4-cyclohexelene, 4,1-cyclohexelene, 2,5-cyclohexelene, 5,2-cyclohexelene, 3,6-cyclohexelene, 6,3-cyclohexelene, 2,5-pyrimidinediyl, 5,2-pyrimidinediyl, 2,5-pyridinediyl, 5,2-pyridinediyl, 2,5-dioxane diyl, or 5,2-dioxane diyl, which may be substituted by fluorine. More suitably, the ring G represents 1,4-cyclohexylene, 1,4-cyclohexelene, 4,1-cyclohexelene, 2,5-cyclohexelene, 5,2-cyclohexelene, 3,6-cyclohexelene or 6,3-cyclohexelene.

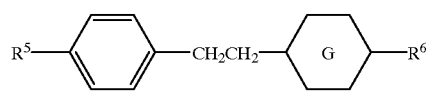
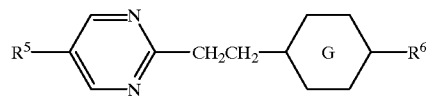
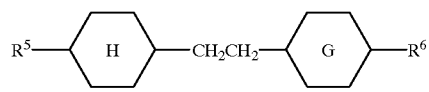
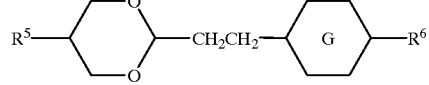
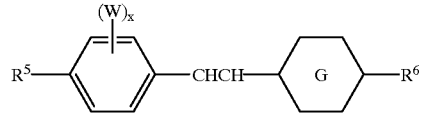
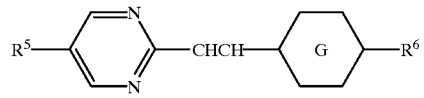
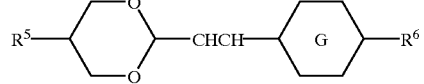
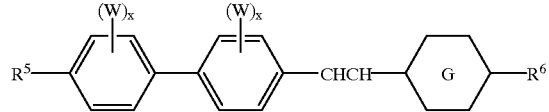
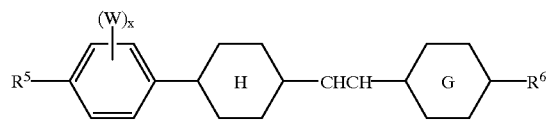

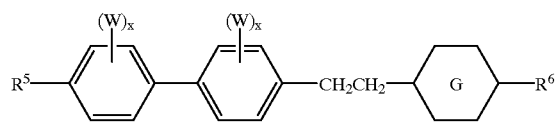
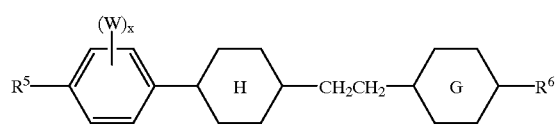
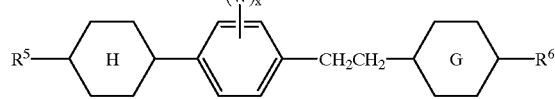
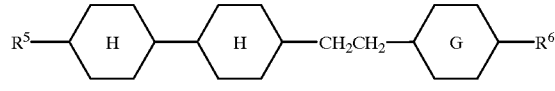
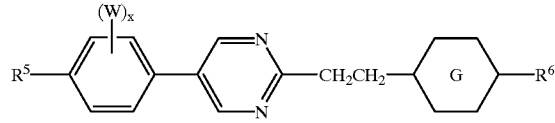
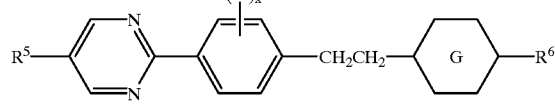
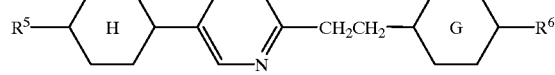
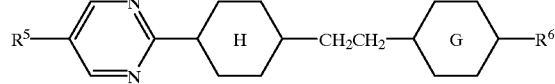
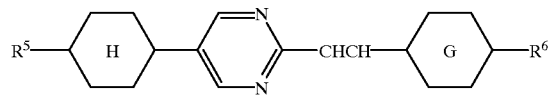
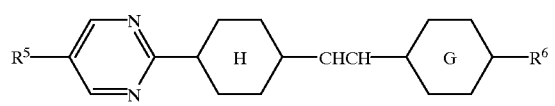

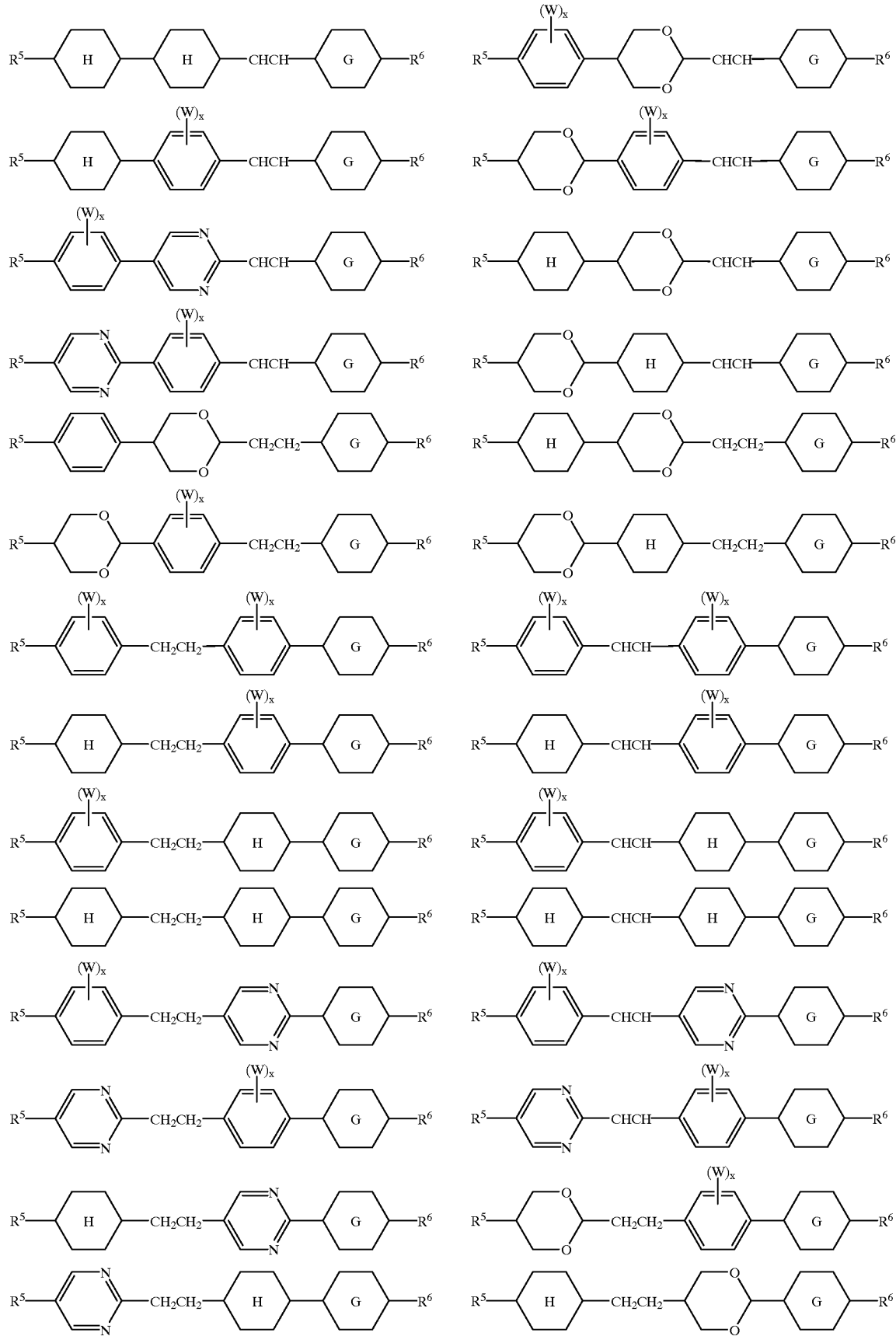

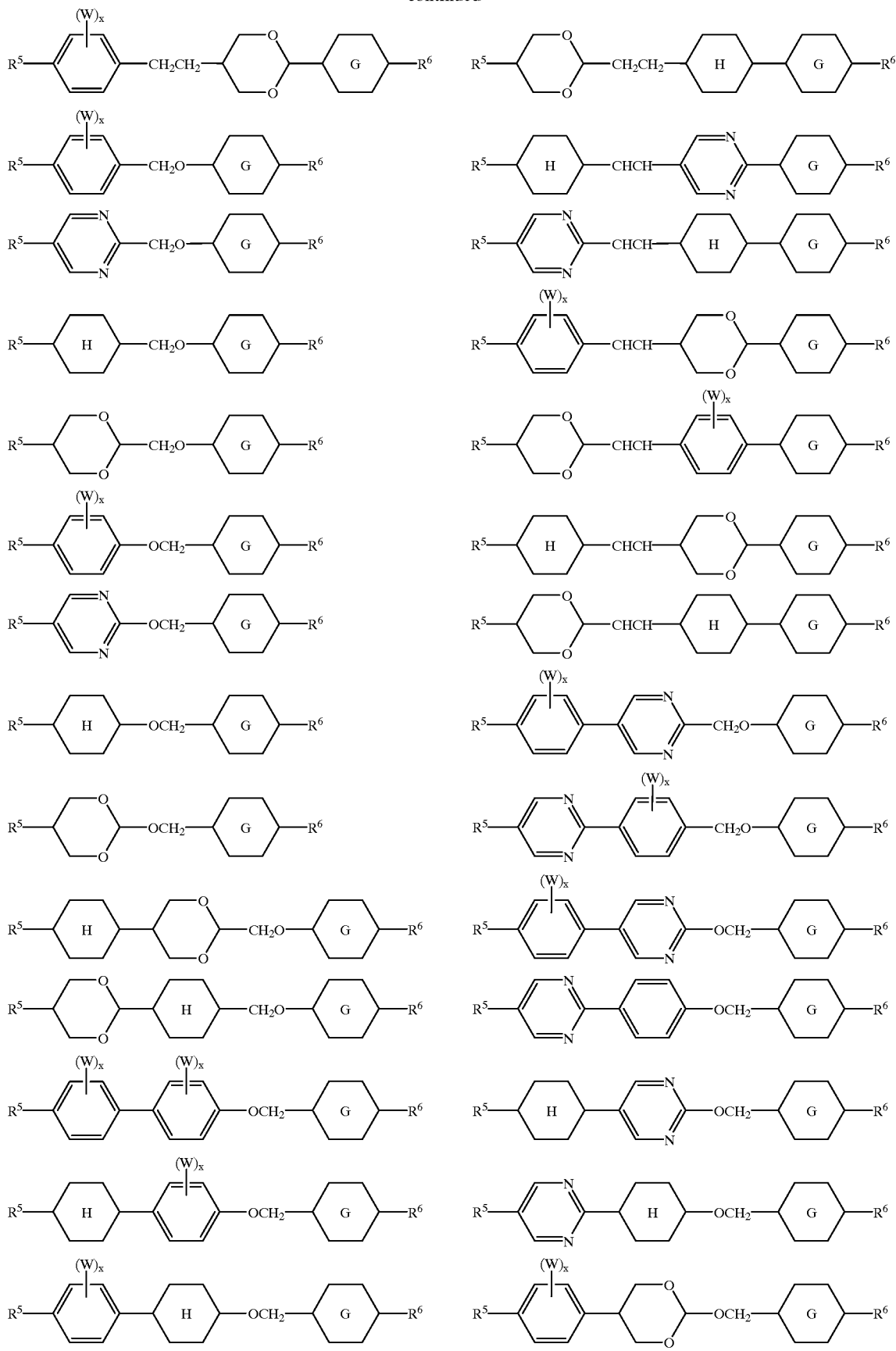

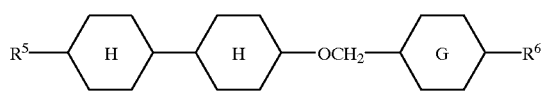
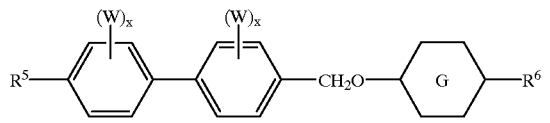
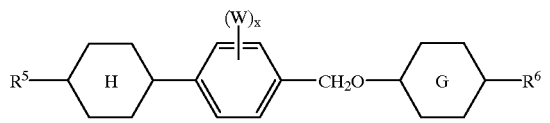
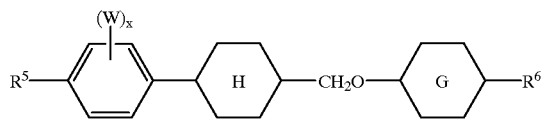
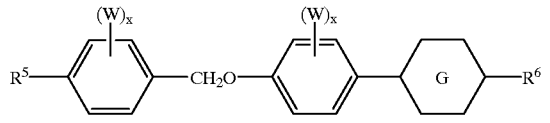
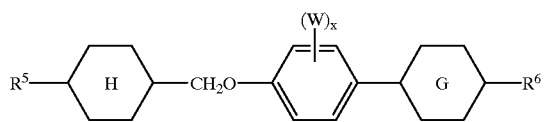
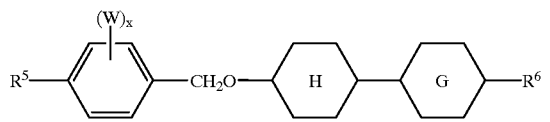
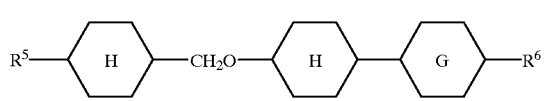
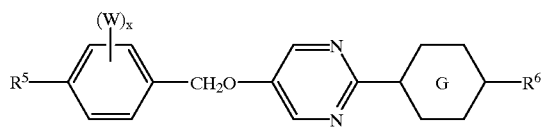
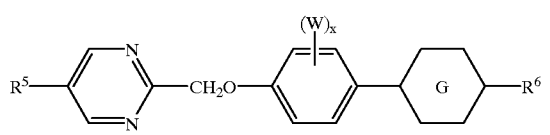
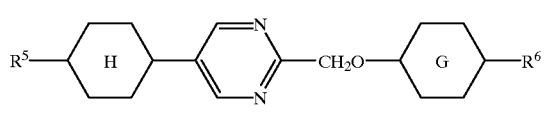
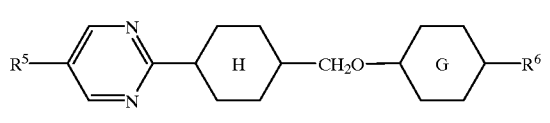
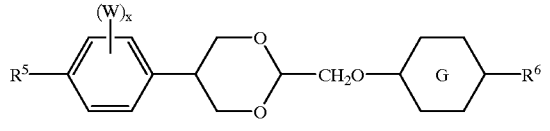
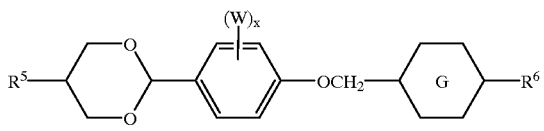
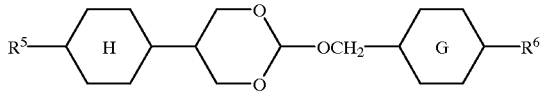
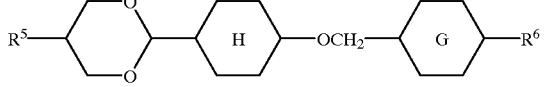
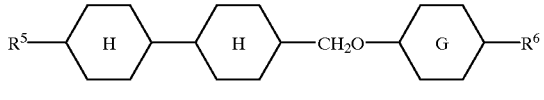
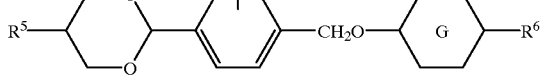
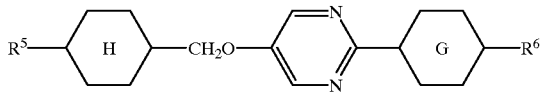
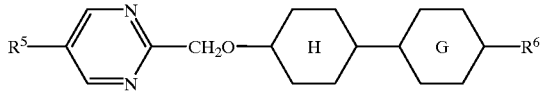
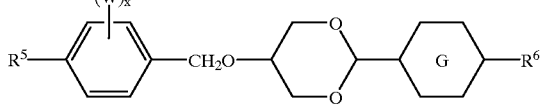
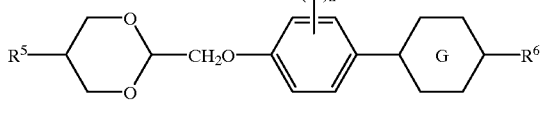
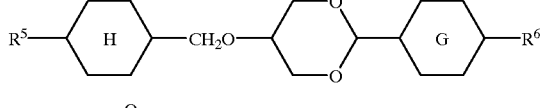
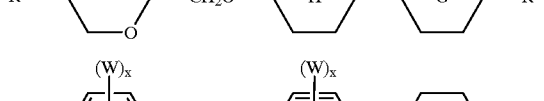
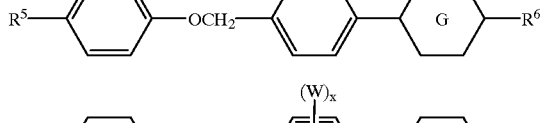
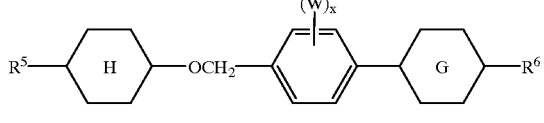

-continued
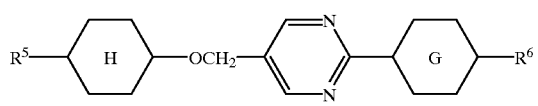
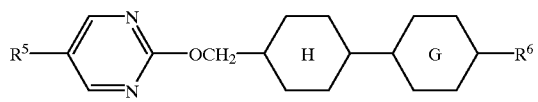
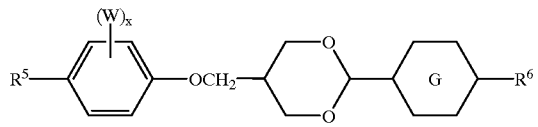
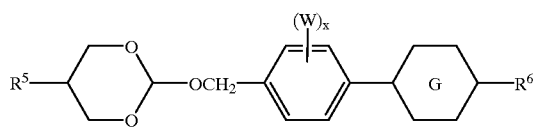
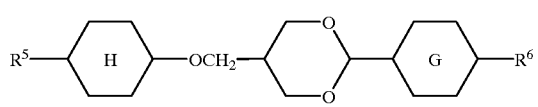
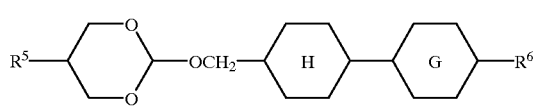
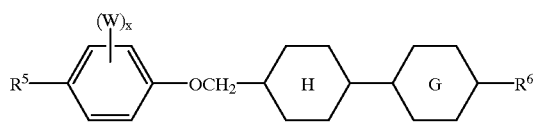
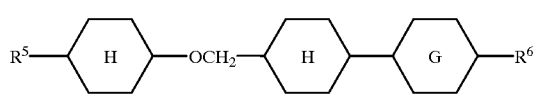
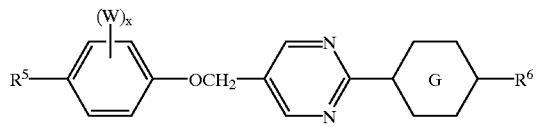
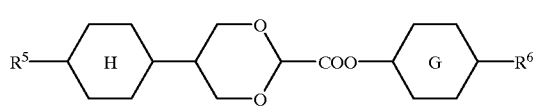
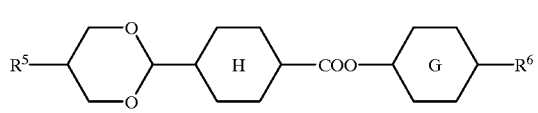
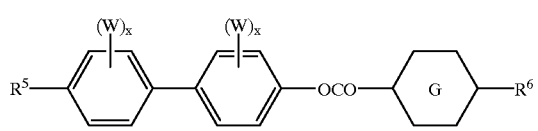
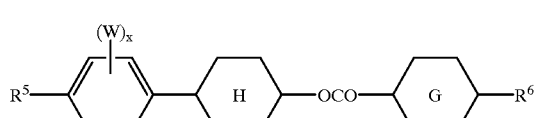
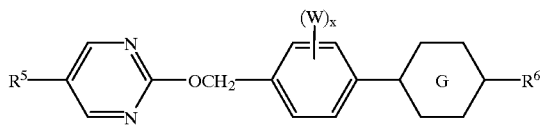
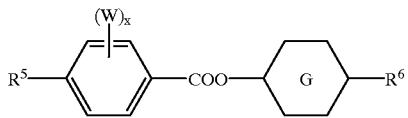
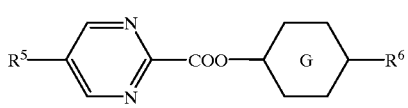
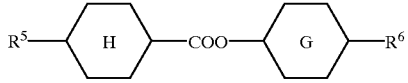
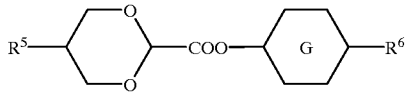
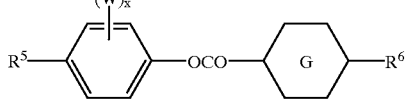
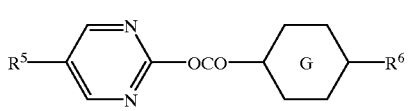
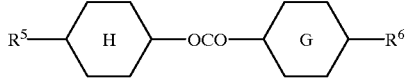
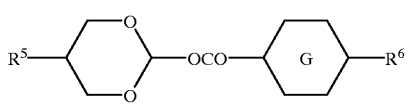
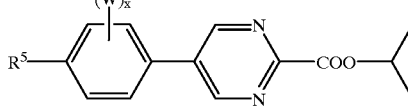
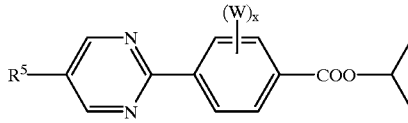
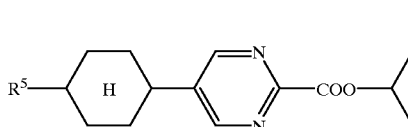
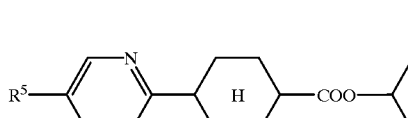

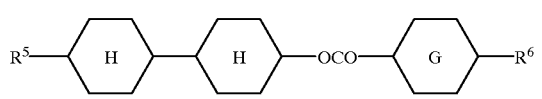
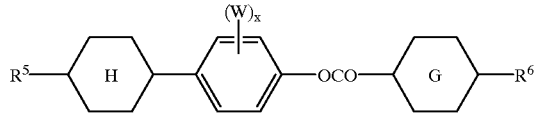
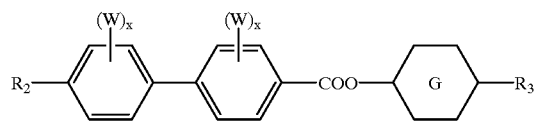
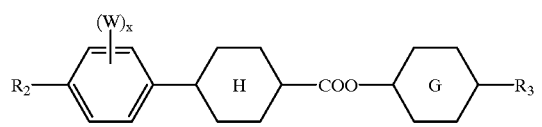
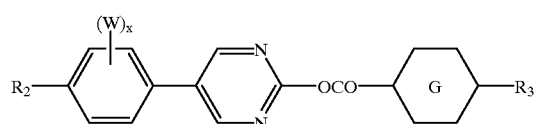
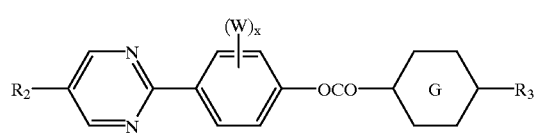
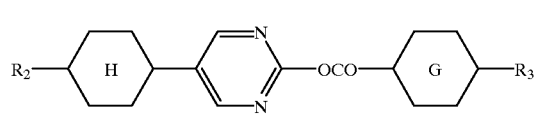
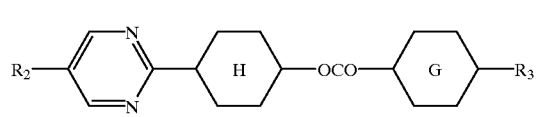
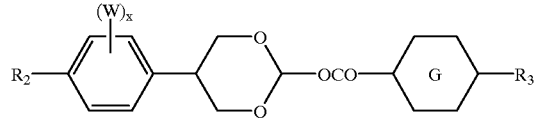
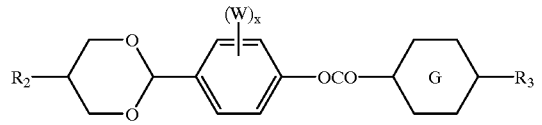
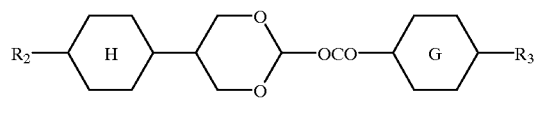
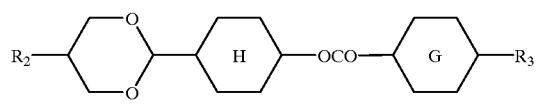
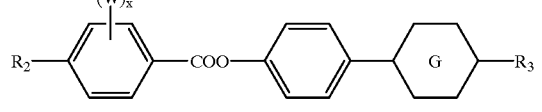
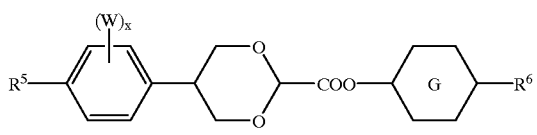
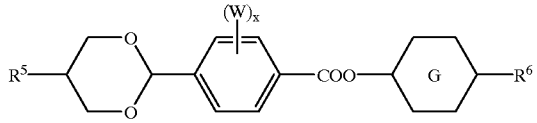
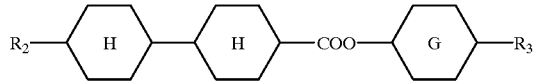
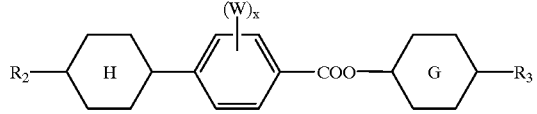
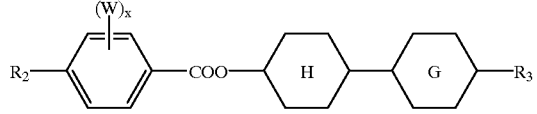
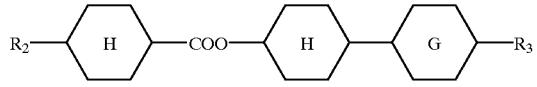
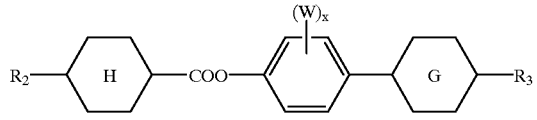
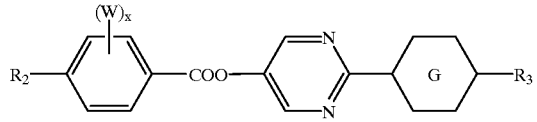
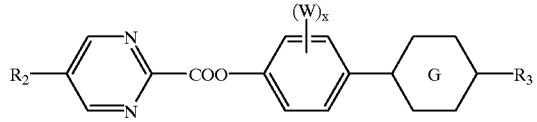
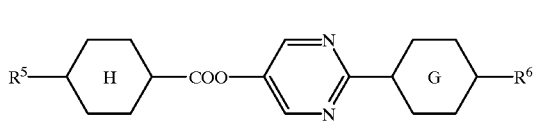
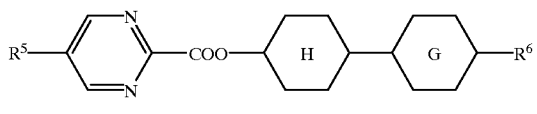
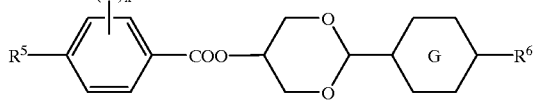
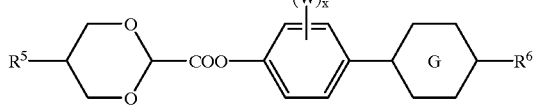

-continued
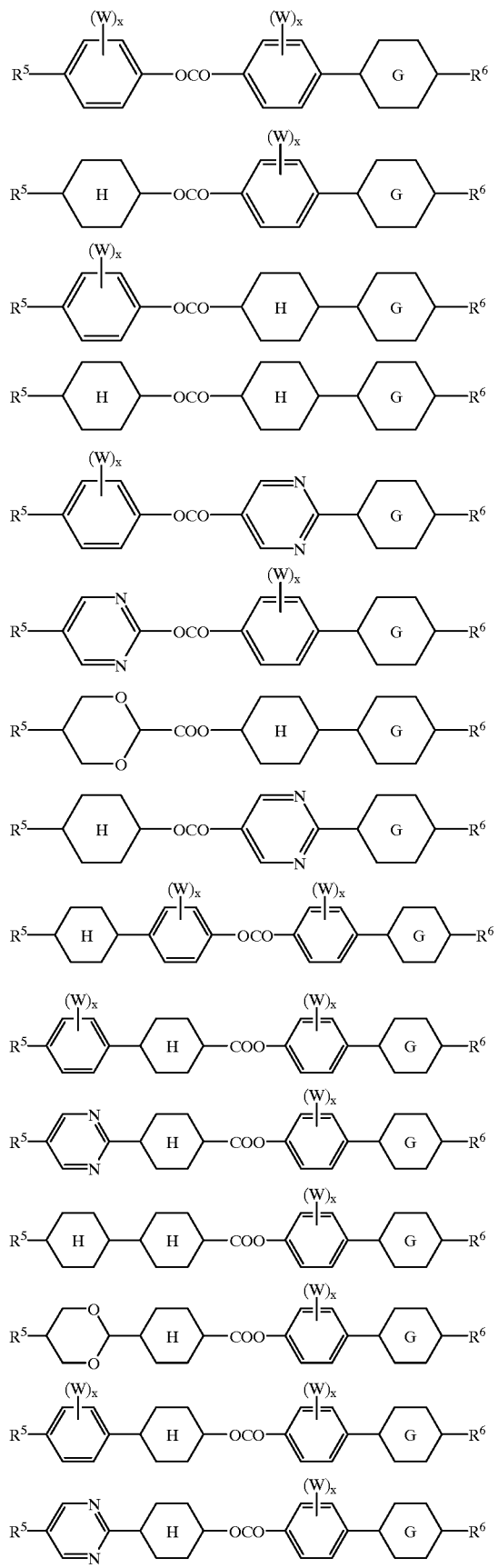
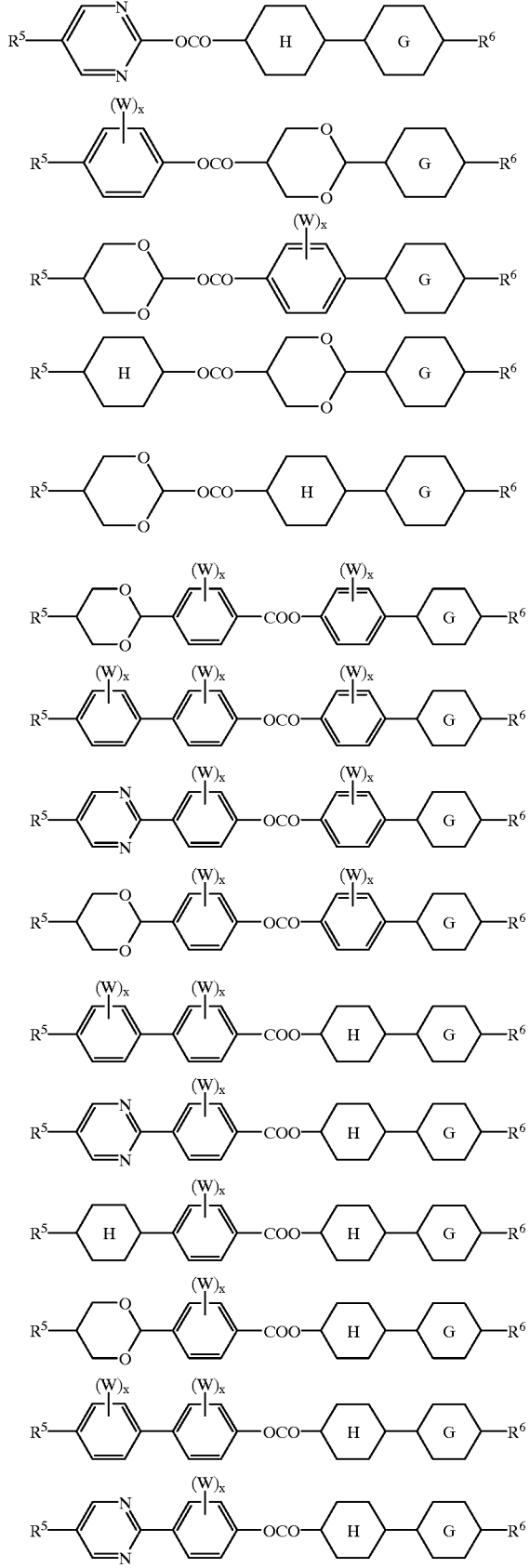

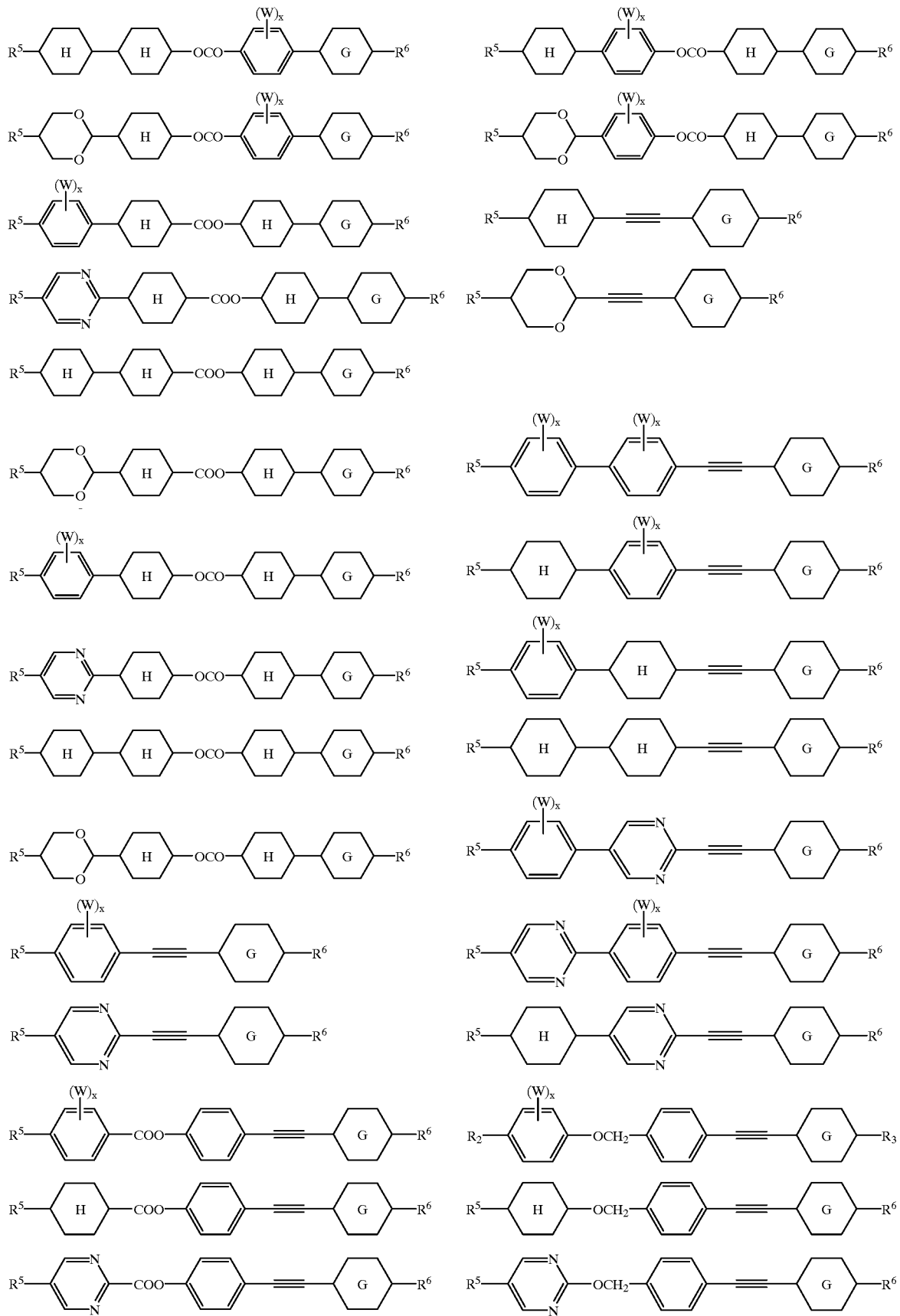

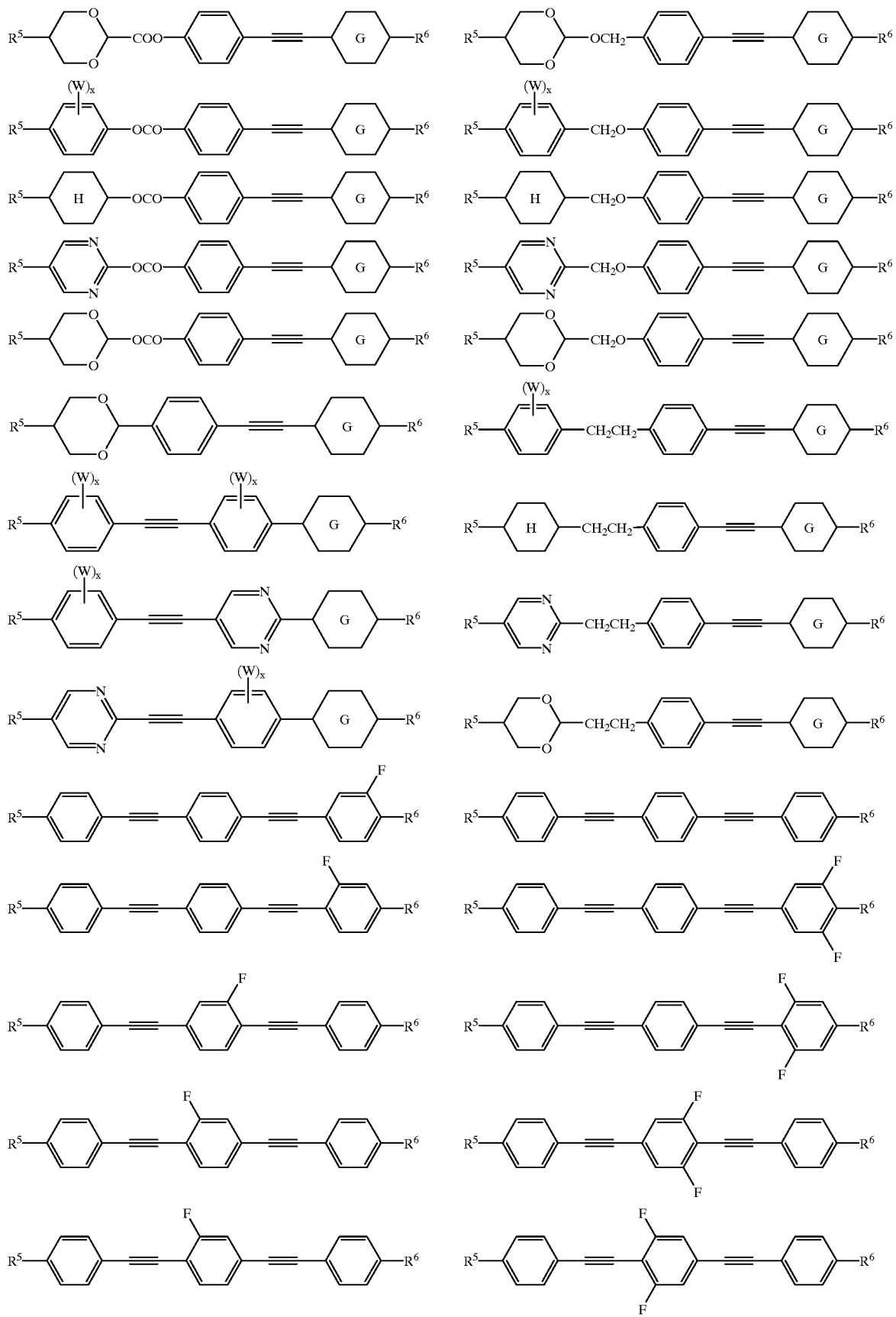
-continued

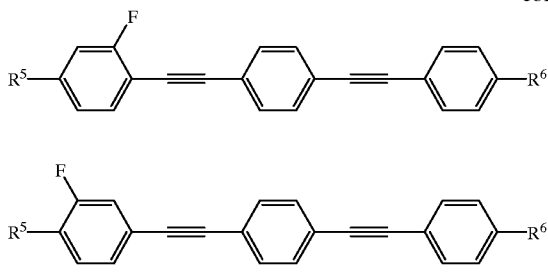
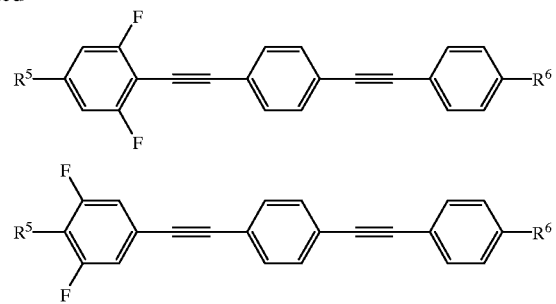

Examples of the compound represented by the formula (3) include preferably compounds in which the ring D in formula (3) is 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, or 6,3-cyclohexenylene, which may be substituted by fluorine.

In the above-mentioned formula (4), $J^1$ shows hydrogen atom, fluorine atom, cyano group or $J^3(O)m^1$. Here, $J^3$ shows alkyl group having 1–12 carbon atoms, alkenyl group having 2–12 carbon atoms, or alkynyl group having 2–12 carbon atoms, which may be substituted by fluorine, and $m^1$ shows 0 or 1.

Concrete examples of the above-mentioned $J^3(O)m^1$ in $J^1$ include: methyl group, ethyl group, propyl group, butyl group, pentyl group, hexyl group, heptyl group, octyl group, nonyl group, decyl group, undecyl group, dodecyl group, ethenyl group, propenyl group, butenyl group, pentenyl group, hexenyl group, heptenyl group, octenyl group, nonenyl group, decenyl group, undecenyl group, dodecenyl group, propynyl group, butynyl group, pentynyl group, hexynyl group, heptynyl group, octynyl group, nonynyl group, decynyl group, dodecynyl group, methoxy group, ethoxy group, propoxy group, butoxy group, pentyloxy group, hexyloxy group, octyloxy group, nonyloxy group, decyloxy group, undecyloxy group, dodecyloxy group, vinyloxy group, propenyloxy group, butenyloxy group, pentenyloxy group, hexenyloxy group, heptenyloxy group, octenyloxy group, nonenyloxy group, decenyloxy group, propionyloxy group, butynyloxy group, pentynyloxy group, hexynyloxy group, heptynyloxy group, octynyloxy group, nonynyloxy group, dodecynyloxy group, trifluoromethyl group, trifluoromethoxy group, difluoromethyl group, trifluoroethyl group, tetrafluoroethyl group, pentafluoroethyl group, etc.

In the above formula (4), $J^2$ is a hydrogen atom, an alkyl group having 1–12 carbon atoms, an alkenyl group having 2–12 carbon atoms, or an alkoxyalkyl group having 2–16 carbon atoms.

Concrete examples of $J^2$ include: hydrogen atom; alkyl groups such as methyl group, ethyl group, propyl group, butyl group, pentyl group, hexyl group, heptyl group, octyl group, nonyl group, decyl group undecyl group, and dodecyl group; alkenyl groups such as ethenyl group, propenyl group, butenyl group, pentenyl group, hexenyl group, heptenyl group, octenyl group, nonenyl group, decenyl group, undecenyl group, and dodecenyl group; alkoxyalkyl groups, such as methoxymethyl group, ethoxymethyl group, propoxymethyl group, butoxymethyl group, pentyloxymethyl group, hexyloxymethyl group, heptyloxymethyl group, octyloxymethyl group, nonyloxymethyl group, decyloxymethyl group, methoxyethyl group, ethoxyethyl group, propoxyethyl group, butoxyethyl group, pentyloxyethyl group, hexyloxyethyl group, heptyloxyethyl group, octyloxyethyl group, nonyloxyethyl group, decyloxyethyl group, methoxypropyl group, ethoxypropyl group, propoxypropyl group, butoxypropyl group, pentyloxypropyl group, hexyloxypropyl group, heptyloxypropyl group, octyloxypropyl group, nonyloxypropyl group, decyloxypropyl group, methoxybutyl group, ethoxybutyl group, propoxybutyl group, butoxybutyl group, pentyloxybutyl group, hexyloxybutyl group, heptyloxybutyl group, octyloxybutyl group, nonyloxybutyl group, decyloxybutyl group, methoxypentyl group, ethoxypentyl group, propoxypentyl group, butoxypentyl group, pentyloxypentyl group, hexyloxypentyl group, heptyloxypentyl group, octyloxypentyl group, etc.

Examples of a compound represented by the formula (4) include: 1-(1,2-difluoro-1-(E)-pentenyl)-4-(2-(4-propylphenyl)ethynyl)benzene, 1-(1,2-difluoro-1-(E)-heptenyl)-4-(2-(4-propylphenyl)ethynyl)benzene, 1-(1,2-difluoro-1-(E)-butenyl)-4-(2-(4-propylphenyl)ethynyl)benzene, 1-(1,2-difluoro-1-(E)-hexenyl)-4-(2-(4-methylphenyl)ethynyl)benzene, 1-(1,2-difluoro-1-(E)-hexenyl)-4-(2-(4-ethylphenyl)ethynyl)benzene, 1-(1,2-difluoro-1-(E)-hexenyl)-4-(2-(4-butylphenyl)ethynyl)benzene, 1-(1,2-difluoro-1-(E)-hexenyl)-4-(2-(4-pentylphenyl)ethynyl)benzene, 1-(1,2-difluoro-1-(E)-hexenyl)-4-(2-(4-hexylphenyl)ethynyl)benzene, 1-(1,2-difluoro-1-(E)-hexenyl)-4-(2-(4 -heptylphenyl)ethynyl)benzene, 1-(1,2-difluoro-1-(E)-hexenyl)-4-(2-(4-methoxyphenyl)ethynyl)benzene, 1-(1,2-difluoro-1-(E)-hexenyl)-4-(2-(4-ethoxyphenyl)ethynyl)benzene, 1-(1,2-difluoro-1-(E)-hexenyl)-3-fluoro-4-(2-(4-pentylphenyl)ethynyl)benzene, 1-(1,2-difluoro-1-(E)-hexenyl)-2-fluoro-4-(2-(4-pentylphenyl)ethynyl)benzene, 1-(1-fluoro-1-(E)-pentenyl)-4-(2-(4-propynylphenyl)ethynyl)benzene, 1-(2-fluoro-1-(E)-pentenyl)-4-(2-(4-propynylphenyl)ethynyl)benzene, 1-(1-fluoro-1-(E)-butenyl)-4-(2-(4-propynylphenyl)ethynyl)benzene, 1-(2-fluoro-1-(E)-hexenyl)-4-(2-(4-methylphenyl)ethynyl)benzene, 1-(1-fluoro-1-(E)-hexenyl)-4-(2-(4-ethylphenyl)ethynyl)benzene, 1-(2-fluoro-1-(E)-hexenyl)-4-(2-(4-butylphenyl)ethynyl)benzene, 1-(1-fluoro-1-(E)-hexenyl)-4-(2-(4-pentylphenyl)ethynyl)benzene, 1-(2-fluoro-1-(E)-hexenyl)-4-(2-(4-hexylphenyl)ethynyl)benzene, 1-(1-fluoro-1-(E)-hexenyl)-4-(2-(4-heptylphenyl)ethynyl)benzene, 1-(2-fluoro-1-(E)-hexenyl)-4-(2-(4-methoxyphenyl)ethynyl)benzene, 1-(1-fluoro-1-(E)-hexenyl)-4-(2-(4-ethoxyphenyl)ethynyl)benzene, 1-(2-fluoro-1-(E)-hexenyl)-3-fluoro-4-(2-(4-pentylphenyl)ethynyl)benzene, 1-(1-fluoro-1-(E)-hexenyl)-2-fluoro-4-(2-(4 -pentylphenyl)ethynyl)benzene, 4-(1,2-difluoro-1-(E)-hexenyl)-1-(2-(4-pentyl cyclohexylphenyl)ethynyl)benzene, 4-(1,2-difluoro-1-(E)-hexenyl)-3-fluoro-1-(2-(4-propyl cyclohexylphenyl)ethynyl)benzene, 4-(1-fluoro-1-(E)-hexenyl)-1-(2-(4-propyl cyclohexylphenyl)ethynyl)benzene, 4-(2-(4-(1,2-difluoro-1-

(E)-pentenyl)phenyl)ethyl)benzonitrile, 4-(2-(4-(1,2-difluoro-1-(E)-heptenyl)phenyl)ethyl)benzonitrile, 4-(2-(4-(1-fluoro-1-(E)-pentenyl)phenyl)ethyl)benzonitrile, 4-(2-(4-(2-fluoro-1-(E)-pentenyl)phenyl)ethyl)benzonitrile, 4-(2-(4-(1,2-difluoro-1-(E)-pentenyl)phenyl)ethyl)-3-fluorobenzonitrile, 4-(2-(4-(1,2-difluoro-1-(E)-hexenyl)phenyl)ethyl)-3-fluorobenzonitrile, 4-(2-(4-(1,2-difluoro-1-(E)-pentenyl)phenyl)ethyl)-3-fluorobenzonitrile, 4-(2-(4-(1-fluoro-1-(E)-pentenyl)phenyl)ethyl)-3-fluorobenzonitrile, 4-(2-(4-(2-fluoro-1-(E)-pentenyl)phenyl)ethyl)-3-fluorobenzonitrile, 1-(1,2-difluoro-1-(E)-heptenyl)-4-(2-(4-trifluoromethoxyphenyl)ethynyl)benzene, 1-(1,2-difluoro-1-(E)-hexenyl)-4-(2-(4-trifluoromethoxyphenyl)ethynyl)benzene, 1-(1,2-difluoro-1-(E)-pentenyl)-4-(2-(4-trifluoromethoxyphenyl)ethynyl)benzene, 1-(1,2-difluoro-1-(E)-heptenyl)-3-fluoro-4-(2-(4-trifluoromethoxyphenyl)ethynyl)benzene, 1-(1,2-difluoro-1-(E)-hexenyl)-3-fluoro-4-(2-(4-trifluoromethoxyphenyl)ethynyl)benzene, 1-(1,2-difluoro-1-(E)-pentenyl)-3-fluoro-4-(2-(4-trifluoromethoxyphenyl)ethynyl)benzene, 1-(1-fluoro-1-(E)-heptenyl)-4-(2-(4-trifluoromethoxyphenyl)ethynyl)benzene, 1-(2-fluoro-1-(E)-hexenyl)-4-(2-(4-trifluoromethoxyphenyl)ethynyl)benzene, 1-(1-fluoro-1-(E)-pentenyl)-4-(2-(4-trifluoromethoxyphenyl)ethynyl)benzene, 1-(1-fluoro-1-(E)-pentenyl)-4-(2-(4-trifluoromethoxyphenyl)ethynyl)benzene, 1-(2-fluoro-1-(E)-heptenyl)-3-fluoro-4-(2-(4-trifluoromethoxyphenyl)ethynyl)benzene, 1-(1-fluoro-1-(E)-hexenyl)-3-fluoro-4-(2-(4-trifluoromethoxyphenyl)ethynyl)benzene and 1-(2-fluoro-1-(E)-pentenyl)-3-fluoro-4-(2-(4-trifluoromethoxyphenyl)ethynyl)benzene. Examples of a compound represented by the formula (5) include: 4-(1,2-difluoro-1-(E)-hexenyl)-1-(4-trans-propylcyclohexyl)benzene, 4-(1-fluoro-1-(E)-hexenyl)-1-(4-trans-propylcyclohexyl)benzene, 4-(1,2-difluoro-1-(E)-pentenyl)-1-(4-trans-propylcyclohexyl)benzene, 4-(1,2-difluoro-1-(E)-hexenyl)-1-(4-(4-trans-propylcyclohexyl)cyclohexyl)benzene, 4-(1,2-difluoro-1-(E)-pentenyl)-1-(4-(4-trans-propylcyclohexyl)cyclohexyl)benzene, 4-(1,2-difluoro-1-(E)-hexenyl)-2-fluoro-1-(4-trans-propylcyclohexyl)cyclohexyl)benzene, 4-(1,2-difluoro-1-(E)-hexenyl)-3-fluoro-1-(4-(4-trans-propylcyclohexyl)cyclohexyl)benzene, 4-(1-fluoro-1-(E)-hexenyl)-1-(4-(4-trans-propylcyclohexyl)cyclohexyl)benzene, 4-(2-fluoro-1-(E)-pentenyl)-1-(4-(4-trans-propylcyclohexyl)cyclohexyl)benzene, 2-fluoro-4-(1-fluoro-1-(E)-hexenyl)-1-(4-(4-trans-propylcyclohexyl)cyclohexyl)benzene, 3-fluoro-4-(2-fluoro-1-(E)-hexenyl)-1-(4-(4-trans-propylcyclohexyl)cyclohexyl)benzene, 4-(1,2-difluoro-1-(E)-hexenyl)-4'-propylbiphenyl, 4-(1,2-difluoro-1-(E)-propenyl)-4'-propylbiphenyl, 4-(1,2-difluoro-1-(E)-heptenyl)-4'-propylbiphenyl, 4-(1,2-difluoro-1-(E)-hexenyl)-4'-methylbiphenyl, 4-(1,2-difluoro-1-(E)-heptenyl)-4'-ethylbiphenyl, 4-(1,2-difluoro-1-(E)-heptenyl)-4'-pentylbiphenyl, 4-(1,2-difluoro-1-(E)-nonenyl)-4'-decylbiphenyl, 4-(1,2-difluoro-1-(E)-nonenyl)-4'-nonylbiphenyl, 4-(1,2-difluoro-1-(E)-hexenyl)-4'-fluorobiphenyl, 4-(1,2-difluoro-1-(E)-hexenyl)-4'-cyanobiphenyl, 4-(1,2-difluoro-1-(E)-hexenyl)-3'-fluoro-4'-cyanobiphenyl, 2-fluoro-4-(1,2-difluoro-1-(E)-hexenyl)-4'-hexenyl)-propylbiphenyl, 2'-fluoro-4-(1,2-difluoro-1-(E)-hexenyl)-4'-propylbiphenyl, 3-fluoro-4-(1,2-difluoro-1-(E)-hexenyl)-4'-propylbiphenyl, 2,3-difluoro-4-(1,2-difluoro-1-(E)-hexenyl)-4'-propylbiphenyl, 2,3-difluoro-4-(1,2-difluoro-1-(E)-nonenyl)-4'-decylbiphenyl, 4-(1-fluoro-1-(E)-hexenyl)-4'-propylbiphenyl, 4-(2-fluoro-1-(E)-propenyl)-4'-propylbiphenyl, 4-(1-fluoro-1-(E)-heptenyl)-4'-propylbiphenyl, 4-(2-fluoro-1-(E)-hexenyl)-4'-methylbiphenyl, 4-(1-fluoro-1-(E)-heptenyl)-4'-ethylbiphenyl, 4-(2-fluoro-1-(E)-heptenyl)-4'-pentylbiphenyl, 4-(1-fluoro-1-(E)-nonenyl)-4'-decylbiphenyl, 4-(2-fluoro-1-(E)-nonenyl)-4'-nonylbiphenyl, 4-(1-fluoro-1-(E)-hexenyl)-4'-fluorobiphenyl, 4-(2-fluoro-1-(E)-hexenyl)-4'-cyano biphenyl, 4-(1-fluoro-1-(E)-hexenyl)-3'-fluoro-4'-cyano biphenyl, 2-fluoro-4-(2-fluoro-1-(E)-hexenyl)-4'-propylbiphenyl, 2'-fluoro-4-(1-fluoro-1-(E)-hexenyl)-4'-propylbiphenyl, 3-fluoro-4-(2-fluoro-1-(E)-hexenyl)-4'-propylbiphenyl, 2,3-difluoro-4-(1-fluoro-1-(E)-hexenyl)-4'-propylbiphenyl, 2,3-difluoro-4-(1-fluoro-1-(E)-nonenyl)-4'-decylbiphenyl, 4-(1,2-difluoro-1-(E)-hexenyl)-4''-propyl-p-terphenyl, 4-(1,2-difluoro-1-(E)-hexenyl)-4''-cyano-p-terphenyl, 4-(1,2-difluoro-1-(E)-hexenyl)-4''-cyano-3''-fluoro-p-terphenyl, 4-(1-fluoro-1-(E)-hexenyl)-4''-propyl-p-terphenyl, 4-(2-fluoro-1-(E)-hexenyl)-4''-cyano-p-terphenyl, 2-(4-(1-(1,2-difluoro-1-(E)-hexenyl))phenyl)-5-propylpyrimidine, 2-(4-(1-(1,2-difluoro-1-(E)-pentenyl))phenyl)-5-propylpyrimidine, 2-(4-(1-(1,2-difluoro-1-(E)-nonenyl))phenyl)-5-decyl pyrimidine, 2-(4-(1-(1,2-difluoro-1-(E)-nonenyl))-2,3-difluorophenyl)-5-decyl pyrimidine, 2-(4-(1-(1,2-difluoro-1-(E)-nonenyl))-3-fluorophenyl)-5-decyl pyrimidine, 2-(4-(1-(1-fluoro-1-(E)-hexenyl))phenyl)-5-propylpyrimidine, 2-(4-(1-(2-fluoro-1-(E)-pentenyl))phenyl)-5-propylpyrimidine, 2-(4-(1-(1-fluoro-1-(E)-nonenyl))phenyl)-5-decyl pyrimidine, 2-(4-(1-(2-fluoro-1-(E)-nonenyl))-2,3-difluorophenyl)-5-decyl pyrimidine, 2-(4-(1-(1-fluoro-1-(E)-nonenyl))-3-fluorophenyl)-5-decyl pyrimidine, 1-(4-methylphenyl-methyl)-4-(1,2-difluoro-1-(E)-pentenyl)benzene, 1-(4-ethylphenyl-methyl)-4-(1,2-difluoro-1-(E)-pentenyl)benzene, 1-(4-propylphenyl-methyl)-4-(1-fluoro-1-(E)pentenyl)benzene, 1-(4-propylphenyl-methyl)-4-(1,2-difluoro-1-(E)-hexenyl)benzene, 1-(4-propylphenyl-methyl)-4-(2-fluoro-1-(E)-heptenyl)benzene, 1-(4-trifluoromethylphenyl-methyl)-4-(1,2-difluoro-1-(E)-pentenyl)benzene, 1-( 3,4,5-trifluorophenyl-methyl)-4-(1-fluoro-1-(E)-pentenyl)benzene, 1-(2-(4-methylphenyl)ethyl)-4-(1,2-difluoro-1-(E)-pentenyl)benzene, 1-(2-(4-ethylphenyl)ethyl)-4-(2-fluoro-1-(E)-pentenyl)benzene, 1-(2-(4-propylphenyl)ethyl)-4-(1,2-difluoro-1-(E)-pentenyl)benzene, 1-(2-(4-butylphenyl)ethyl)-4-(1-fluoro-1-(E)-pentenyl)benzene, 1-(2-(4-pentylphenyl)ethyl)-4-(1,2-difluoro-1-(E)-pentenyl)benzene, 1-(2-(4-hexylphenyl)ethyl)-4-(2-fluoro-1-(E)-pentenyl)benzene, 1-(2-(4-heptylphenyl)ethyl)-4-(1,2-difluoro-1-(E)-pentenyl)benzene, 1-(2-(4-octylphenyl)ethyl)-4-(1-fluoro-1-(E)-pentenyl)benzene, 1-(2-(4-nonylphenyl)ethyl)-4-(1,2-difluoro-1-(E)-pentenyl)benzene, 1-(2-(4-propylphenyl)ethyl)-4-(1-fluoro-1-(E)-butenyl)benzene, 1-(2-(4-decylphenyl)ethyl)-4-(2-fluoro-1-(E)-pentenyl)benzene, 1-(2-(4-propylphenyl)ethyl)-4-(1,2-difluoro-1-(E)-propenyl)benzene, 1-(2-(4-propylphenyl)ethyl)-4-(1,2-difluoro-1-(E)-hexenyl)benzene, 1-(2-(4-propylphenyl)ethyl)-4-(2-fluoro-1-(E)-heptenyl)benzene, 1-(2-(4-propylphenyl)ethyl)-4-(1,2-difluoro-1-(E)-octenyl)benzene, 1-(2-(4-decylphenyl)ethyl)-4-(1-fluoro-1-(E)-nonenyl)benzene, 1-(2-(4-decylphenyl)ethyl)-4-(1,2-difluoro-1-(E)-nonenyl)benzene, 1-(4-propylcyclohexyl)-4-(2-(4-(2-fluoro-1-(E)-propenyl)-phenyl)ethyl)benzene, 1-(4-propylcyclohexyl)-4-(2-(4-(1,2-difluoro-1-(E)-butenyl)-phenyl)ethyl)benzene, 1-(4-propylcyclohexyl)-4-(2-(4-(1-fluoro-1-(E)-pentenyl)-phenyl)ethyl)benzene, 1-(4-propylcyclohexyl)-4-(2-(4-(1,2-difluoro-1-(E)-hexenyl)-phenyl)ethyl)benzene, 1-(4-propylcyclohexyl)-4-(2-(4-(2-fluoro-1-(E)-heptenyl)-phenyl)ethyl)benzene, 1-(4-propylcyclohexyl)-4-(2-(4-(1,2-difluoro-1-(E)-octenyl)- phenyl)ethyl)benzene, 1-(4-propylcyclohexyl)-4-(2-(4-(1-fluoro-1-(E)-nonenyl)-phenyl)ethyl)benzene, 1-(4-butyl cyclohexyl)-4-(2-(4-(1,2-difluoro-1-(E)-pentenyl)-phenyl) ethyl)benzene, 1-(4-pentylcyclohexyl)-4-(2-(4-(2-fluoro-1-(E)-pentenyl)-phenyl)ethyl)benzene, 1-(4-propyl-1-cyclohexenyl)-4-(2-(4-(1,2-difluoro-1-(E)-pentenyl)-phenyl)ethyl)benzene, 1-(4-propyl-1-cyclohexenyl)-4-(2-(4-(1-fluoro-1-(E)-heptenyl)-phenyl)ethyl)benzene, 1-(2-(4-trifluoromethylphenyl)ethyl)-4-(1,2-difluoro-1-(E)-pentenyl)benzene, 1-(2-(4-cyano phenyl)ethyl)-4-(2-fluoro-1-(E)-pentenyl)benzene, 1-(2-(4-fluorophenyl)ethyl)-4-(1,2-difluoro-1-(E)-pentenyl)benzene, 1-(2-(3,4-difluorophenyl)ethyl)-4-(1-fluoro-1-(E)-pentenyl)benzene, 1-(2-(3,4-difluorophenyl)ethyl)-4-(1,2-difluoro-1-(E)-heptenyl)benzene, 1-(2-(3,4,5-trifluorophenyl)ethyl)-4-(2-fluoro-1-(E)-propenyl)benzene, 1-(2-(3,4,5-trifluorophenyl)ethyl)-4-(1,2-difluoro-1-(E)-butenyl)benzene, 1-(2-(3,4,5-trifluorophenyl)ethyl)-4-(1-fluoro-1-(E)-pentenyl)benzene, 1-(2-(3,4,5-trifluorophenyl)ethyl)-4-(1,2-difluoro-1-(E)-hexenyl)benzene, 1-(2-(3,4,5-trifluorophenyl)ethyl)-4-(2-fluoro-1-(E)-heptenyl)benzene, 1-(2-(3,4,5-trifluorophenyl)ethyl-4-(1,2-difluoro-1-(E)-octenyl)benzene, 1-(2-(3,4,5-trifluorophenyl)ethyl)-4-(1-fluoro-1-(E)-nonenyl)benzene, 1-(2-(4-propyl-3,5-difluorophenyl)ethyl)-4-(1,2-difluoro-1-(E)-propenyl)benzene, 1-(2-(4-propyl-3,5-difluorophenyl)ethyl)-4-(2-fluoro-1-(E)-butenyl)benzene, 1-(2-(4-propyl-3,5-difluorophenyl)ethyl)-4-(1,2-difluoro-1-(E)-pentenyl)benzene, 1-(2-(4-propyl-3,5-difluorophenyl)ethyl)-4-(1-fluoro-1-(E)-hexenyl)benzene, 1-(2-(4-propyl-3,5-difluorophenyl)ethyl)-4-(1,2-difluoro-1-(E)-heptenyl)benzene, 1-(2-(4-methyl-3,5-difluorophenyl)ethyl)-4-(2-fluoro-1-(E)-pentenyl)benzene, 1-(2-(4-ethyl-3,5-difluorophenyl)ethyl)-4-(1,2-difluoro-1-(E)-pentenyl)benzene, 1-(2-(4-butyl-3,5-difluorophenyl)ethyl)-4-(1-fluoro-1-(E)-pentenyl)benzene, 1-(2-(4-propyl-3,5-difluorophenyl)ethyl)-4-(1,2-difluoro-1-(E)-pentenyl)benzene, 2-fluoro-1-(2-(4-propylphenyl)ethyl)-4-(2-fluoro-1-(E)-pentenyl)benzene, 2-fluoro-1-(2-(4-propylphenyl)ethyl)-4-(1,2-difluoro-1-(E)-hexenyl)benzene, 2-fluoro-1-(2-(4-propylphenyl)ethyl)-4-(1-fluoro-1-(E)-heptenyl)benzene, 3-fluoro-1-(2-(4-propylphenyl)ethyl)-4-(1,2-difluoro-1-(E)-pentenyl)benzene, 3-fluoro-1-(2-(4-propylphenyl)ethyl)-4-(2-fluoro-1-(E)-hexenyl)benzene, 2-fluoro-1-(2-(3,4,5-trifluorophenyl)ethyl)-4-(1,2-difluoro-1-(E)-pentenyl)benzene, 2,6-difluoro-1-(2-(3,4,5-trifluorophenyl)ethyl)-4-(1-fluoro-1-(E)-pentenyl)benzene, 2-fluoro-1-(2-(3,4-difluorophenyl)ethyl)-4-(1,2-difluoro-1-(E)-pentenyl)benzene, 2,6-difluoro-1-(2-(3,4-difluorophenyl)ethyl)-4-(2-fluoro-1-(E)-pentenyl)benzene, 2,6-difluoro-1-(2-(4-propyl-3,5-difluorophenyl)ethyl)-4-(1,2-difluoro-1-(E)-pentenyl)benzene, 2,6-difluoro-1-(2-(4-trifluoromethyl-3,5-difluorophenyl)ethyl)-4-(1-fluoro-1-(E)-pentenyl)benzene, 2,6-difluoro-1-(2-(4-trifluoromethoxy-3,5-difluorophenyl)ethyl)-4-(1,2-difluoro-1-(E)-pentenyl)benzene, 1-(2-(4-cyano-3-fluorophenyl)ethyl)-4-(2-fluoro-1-(E)-pentenyl)benzene, 1-(2-(4-cyano-3-fluorophenyl)ethyl)-4-(1,2-difluoro-1-(E)-heptenyl)benzene, 1-(2-(4-cyano-3-fluorophenyl)ethyl)-2-fluoro-4-(1-fluoro-1-(E)-pentenyl)benzene, 1-(2-(4-cyano-3-fluorophenyl)ethyl)-2,6-difluoro-4-(1,2-difluoro-1-(E)-pentenyl)benzene, 1-(2-(4-cyano-3,5-difluorophenyl)ethyl)-4-(2-fluoro-1-(E)-pentenyl)benzene, 1-(2-(4-cyano-3,5-difluorophenyl)ethyl)-2-fluoro-4-(1,2-difluoro-1-(E)-pentenyl)benzene, 1-(2-(4-cyano-3,5-difluorophenyl)ethyl)-2,6-difluoro-4-(1-fluoro-1-(E)-pentenyl)benzene, 1-(4,4-difluorocyclohexyl)-4-(2-(4-(1,2-difluoro-1-(E)-pentenyl)phenyl)ethyl]benzene, 1-(4-fluorocyclohexyl-4-(2-(4-(2-fluoro-1-(E)-pentenyl)phenyl)ethylbenzene, 1-(2-(4'-propyl-dicyclohexyl)ethyl)-4-(1,2-difluoro-1-(E)-pentenyl)benzene, 1-(2-(4',4-dipropyl-dicyclohexyl)ethyl)-4-(1-fluoro-1-(E)-pentenyl)benzene, 1-(2-(4'-fluoro-dicyclohexyl)ethyl)-4-(1,2-difluoro-1-(E)-pentenyl)benzene, 1-(2-(4',4-difluoro-dicyclohexyl)ethyl)-4-(2-fluoro-1-(E)-pentenyl)benzene, 1-(3-(4-propylphenyl)propyl-4-(1,2-difluoro-1-(E)-pentenyl)benzene, 1-(3-(3,4-difluorophenyl)propyl)-4-(1-fluoro-1-(E)-pentenyl)benzene, 1-(3-(3,4,5-trifluorophenyl)propyl)-4-(1,2-difluoro-1-(E)-pentenyl)benzene, 1-(4-(4-propylphenyl)butyl)-4-(2-fluoro-1-(E)-pentenyl)benzene, 1-(4-(3,4-difluorophenyl)butyl)-4-(1,2-difluoro-1-(E)-pentenyl)benzene, 1-(4-(3,4,5-trifluorophenyl)butyl)-4-(1-fluoro-1-(E)-pentenyl)benzene, 1-(4-(3,5-difluoro-4-propylphenyl)butyl)-4-(1,2-difluoro-1-(E)-pentenyl)benzene, 4-(4-methylbenzyloxy)-1-(2-fluoro-1-(E)-pentenyl)benzene, 4-(4-ethylbenzyloxy)-1-(1,2-difluoro-1-(E)-pentenyl)benzene, 4-(4-propylbenzyloxy)-1-(1-fluoro-1-(E)-pentenyl)benzene, 4-(4-butylbenzyloxy)-1-(1,2-difluoro-1-(E)-pentenyl)benzene, 4-(4-pentylbenzyloxy)-1-(2-fluoro-1-(E)-pentenyl)benzene, 4-(4-hexylbenzyloxy)-1-(1,2-difluoro-1-(E)-pentenyl)benzene, 4-(4-heptylbenzyloxy)-1-(1-fluoro-1-(E)-pentenyl)benzene, 4-(4-octylbenzyloxy)-1-(1,2-difluoro-1-(E)-pentenyl)benzene, 4-(4-propylbenzyloxy)-1-(2-fluoro-1-(E)-heptenyl)benzene, 4-(4-nonylbenzyloxy)-1-(1,2-difluoro-1-(E)-heptenyl)benzene, 4-(4-hexylbenzyloxy)-1-(1-fluoro-1-(E)-nonenyl)benzene, 4-(4-heptylbenzyloxy)-1-(1,2-difluoro-1-(E)-nonenyl)benzene, 4-(4-octylbenzyloxy)-1-(2-fluoro-1-(E)-nonenyl)benzene, 4-(4-nonylbenzyloxy)-1-(1,2-difluoro-1-(E)-nonenyl)benzene, 4-(4-decylbenzyloxy)-1-(1-fluoro-1-(E)-nonenyl)benzene, 4-(4-undecylbenzyloxy)-1-(1,2-difluoro-1-(E)-nonenyl)benzene, 4-(4-trifluorobenzyloxy)-1-(2-fluoro-1-(E)-pentenyl)benzene, 4-(4-trifluorobenzyloxy)-1-(1,2-difluoro-1-(E)-heptenyl)benzene, 4-(4-cyanobenzyloxy)-1-(1-fluoro-1-(E)-pentenyl)benzene, 1-(4-(E)-pentenylbenzyloxy)-4-methylbenzene, 1-(4-(E)-pentenylbenzyloxy)-4-ethylbenzene, 1-(4-(E)-pentenylbenzyloxy)-4-propylbenzene, 1-(4-(E)-pentenylbenzyloxy)-4-butylbenzene, 1-(4-(E)-pentenylbenzyloxy)-4-pentylbenzene, 1-(4-(E)-hexenylbenzyloxy)-4-propylbenzene, 1-(4-(E)-heptenylbenzyloxy)-4-propylbenzene, 1-(4-(E)-pentenylbenzyloxy)-4-trifluoromethylbenzene, 1-(4-(E)-pentenylbenzyloxy)-3,4,5-trifluorobenzene, 1-(4-(E)-pentenylbenzyloxy)-4-cyanobenzene, 4-(4-methylphenoxy)-1-(1,2-difluoro-1-(E)-pentenyl)benzene, 4-(4-ethylphenoxy)-1-(2-fluoro-1-(E)-pentenyl)benzene, 4-(4-propylphenoxy)-1-(1,2-difluoro-1-(E)-pentenyl)benzene, 4-(4-butylphenoxy)-1-(1-fluoro-1-(E)-pentenyl)benzene, 4-(4-pentylphenoxy)-1-(1,2-difluoro-1-(E)-pentenyl)benzene, 4-(4-hexylphenoxy)-1-(2-fluoro-1-(E)-pentenyl)benzene, 4-(4-propylphenoxy)-1-(1,2-difluoro-1-(E)-propenyl)benzene, 4-(4-propylphenoxy)-1-(1-fluoro-1-(E)-butenyl)benzene, 4-(4-propylphenoxy)-1-(1,2-difluoro-1-(E)-pentenyl)benzene, 4-(4-propylphenoxy)-1-(2-fluoro-1-(E)-hexenyl)benzene, 4-(4-propylphenoxy)-1-(1,2-difluoro-1-(E)-heptenyl)benzene, 4-(4-propylphenoxy)-1-(1-fluoro-1-(E)-octenyl)benzene, 4-(4-trifluoromethylphenoxy)-1-(1,2-difluoro-1-(E)-pentenyl)benzene, (4-(2-fluoro-1-(E)-propenyl))phenyl-(4-propyl)benzoate, (4-(1,2-difluoro-1-(E)-butenyl))phenyl-(4-propyl)benzoate, (4-(1-fluoro-1-(E)-pentenyl))phenyl-(4-propyl)benzoate, (4-(1,2-difluoro-1-(E)-hexenyl))phenyl-(4-propyl)benzoate, (4-(2-fluoro-1-(E)-heptenyl))phenyl-(4-propyl)benzoate, (4-(1,2-difluoro-1-(E)-octenyl))phenyl-(4-propyl)benzoate, (4-(1-fluoro-1-(E)-pentenyl))phenyl-(4- methyl)benzoate, (4-(1,2-difluoro-1-(E)-pentenyl))phenyl-(4-ethyl)benzoate, (4-(2-fluoro-1-(E)-pentenyl))phenyl-(4-propyl)benzoate, (4-(1,2-difluoro-1-(E)-pentenyl))phenyl-(4-butyl)benzoate, (4-(1-fluoro-1-(E)-pentenyl))phenyl-(4-pentyl)benzoate, (4-(1,2-difluoro-1-(E)-propenyl))phenyl-(4-(4-propylcyclohexyl))benzoate, (4-(2-fluoro-1-(E)-butenyl))phenyl-(4-(4-propylcyclohexyl))benzoate, (4-(1,2-difluoro-1-(E)-pentenyl))phenyl-(4-(4-propylcyclohexyl))benzoate, (4-(1-fluoro-1-(E)-hexenyl))phenyl-(4-(4-propylcyclohexyl))benzoate, (4-(1,2-difluoro-1-(E)-heptenyl))phenyl-(4-(4-propylcyclohexyl))benzoate, (4-(2-fluoro-1-(E)-octenyl))phenyl-(4-(4-propylcyclohexyl))benzoate, (4-(1,2-difluoro-1-(E)-heptenyl))phenyl-(4-(4-methylcyclohexyl))benzoate, (4-(1-fluoro-1-(E)-pentenyl))phenyl-(4-(4-ethylcyclohexy))benzoate, (4-(1,2-difluoro-1-(E)-pentenyl))phenyl-(4-(4-butylcyclohexyl))benzoate, (4-(2-fluoro-1-(E)-pentenyl))phenyl-(4-(4-pentylcyclohexyl))benzoate, (4-( 1,2-difluoro-1-(E)-pentenyl))phenyl-(4-(4-propylcyclohexyl))benzoate, (4-(1-fluoro-1-(E)-pentenyl))phenyl-(4-(4-pentylcyclohexyl))benzoate, (4-(1,2-difluoro-1-(E)-propenyl))phenyl-(4-cyano-3-fluoro)benzoate, (4-(2-fluoro-1-(E)-butenyl))phenyl-(4-cyano-3-fluoro)benzoate, (4-(1,2-difluoro-1-(E)-pentenyl))phenyl-(4-cyano-3-fluoro)benzoate, (4-(1-fluoro-1-(E)-hexenyl))phenyl-(4-cyano-3-fluoro)benzoate, (4-(1,2-difluoro-1-(E)-heptenyl))phenyl-(4-cyano-3-fluoro)benzoate, (4-(2-fluoro-1-(E)-octenyl))phenyl-(4-cyano-3-fluoro)benzoate, (4-(1,2-difluoro-1-(E)-propenyl))phenyl-(3,4-difluoro))benzoate, (4-(1-fluoro-1-(E)-pentenyl))phenyl-(3,4-difluoro))benzoate, (4-(1,2-difluoro-1-(E)-heptenyl))phenyl-(3,4-difluoro))benzoate, (4-(2-fluoro-1-(E)-propenyl))phenyl-(3,4,5-trifluoro))benzoate, (4-(1,2-difluoro-1-(E)-pentenyl))phenyl-(3,4,5-trifluoro))benzoate, (4-(1-fluoro-1-(E)-heptenyl))phenyl-(3,4,5-trifluoro))benzoate, 4-methylphenyl-(4-(1,2-difluoro-1-(E)-pentenyl))benzoate, 4-ethylphenyl-(4-(2-fluoro-1-(E)-pentenyl))benzoate, 4-propylphenyl-(4-(1,2-difluoro-1-(E)-pentenyl))benzoate, 4-butylphenyl-(4-(1-fluoro-1-(E)-pentenyl))benzoate, 4-pentylphenyl-(4-(1,2-difluoro-1-(E)-pentenyl))benzoate, 4-hexylphenyl-(4-(2-fluoro-1-(E)-pentenyl))benzoate, 4-heptylphenyl-(4-(1,2-difluoro-1-(E)-pentenyl))benzoate, 4-octylphenyl-(4-(1-fluoro-1-(E)-nonenyl))benzoate, 4-nonylphenyl-(4-(1,2-difluoro-1-(E)-nonenyl))benzoate, 4-decylphenyl-(4-(2-fluoro-1-(E)-nonenyl))benzoate, 4-undecylphenyl-(4-(1,2-difluoro-1-(E)-nonenyl))benzoate, 4-octylphenyl-(4-(1-fluoro-1-(E)-nonenyl))benzoate, 4-nonyloxyphenyl-(4-(1,2-difluoro-1-(E)-nonenyl))benzoate, 4-decyloxyphenyl-(4-(2-fluoro-1-(E)-nonenyl))benzoate, 4-(4-methylcyclohexyl)phenyl-(4-(1,2-difluoro-1-(E)-pentenyl))benzoate, 4-(4-ethylcyclohexyl)phenyl-(4-(1-fluoro-1-(E)-pentenyl))benzoate, 4-(4-propylcyclohexyl)phenyl-(4-(1,2-difluoro-1-(E)-pentenyl))baenzoate, 4-(4-butylcyclohexyl)phenyl-(4-(2-fluoro-1-(E)-pentenyl))benzoate, 4-(4-pentylcyclohexyl)phenyl-(4-(1,2-difluoro-1-(E)-pentenyl))benzoate, 4-(4-hexylcyclohexyl)phenyl-(4-(1-fluoro-1-(E)-pentenyl))benzoate, 4-(4-propylcyclohexyl)phenyl-(4-(1,2-difluoro-1-(E)-propenyl))benzoate, 4-(4-propylcyclohexyl)phenyl-(4-(2-fluoro-1-(E)-butenyl))benzoate, 4-(4-propylcyclohexyl)phenyl-(4-(1,2-difluoro-1-(E)-hexenyl))benzoate, 4-(4-propylcyclohexyl)phenyl-(4-(1-fluoro-1-(E)-heptenyl))benzoate, 4-(4-propylcyclohexyl)phenyl-(4-(1,2-difluoro-1-(E)-octenyl))benzoate, 4-(4-propylcyclohexyl)phenyl-(4-(2-fluoro-1-(E)-pentenyl))benzoate, 4-(4-cyano-3-fluoro)phenyl-( 4-(1,2-difluoro-1-(E)-pentenyl))benzoate, 4-(4-cyano-3-fluoro)phenyl-(4-(1-fluoro-1-(E)-heptenyl))benzoate, 4-(3,4-difluoro)phenyl-(4-(1,2-difluoro-1-(E)-pentenyl))benzoate, 4-(3,4-difluoro)phenyl-(4-(2-fluoro-1-(E)-heptenyl))benzoate, 4-(3,4,5-trifluoro)phenyl-(4-(1,2-difluoro-1-(E)-pentenyl))benzoate, 4-(3,4,5-trifluoro)phenyl-(4-(1-fluoro-1-(E)-heptenyl))benzoate, 1-(4-methylphenyl-methyl)-4-(1-(E)-pentenyl)benzene, 1-(4-ethylphenyl-methyl)-4-(1-(E)-pentenyl)benzene, 1-(4-propylphenyl-methyl)-4-(1-(E)-pentenyl)benzene, 1-(4-propylphenyl-methyl)-4-(1-(E)-hexenyl)benzene, 1-(4-propylphenyl-methyl)-4-(1-(E)-heptenyl)benzene, 1-(4-trifluoromethylphenyl-methyl)-4-(1-(E)-pentenyl)benzene, 1-(3,4,5-trifluorophenylmethyl)-4-(1-(E)-pentenyl)benzene, 1-(2-(4-methylphenyl)ethyl)-4-(1-(E)-pentenyl)benzene, 1-(2-(4-ethylphenyl)ethyl)-4-(1-(E)-pentenyl)benzene, 1-(2-(4-propylphenyl)ethyl)-4-(1-(E)-pentenyl)benzene, 1-(2-(4-butylphenyl)ethyl)-4-(1-(E)-pentenyl)benzene, 1-(2-(4-pentylphenyl)ethyl)-4-(1-(E)-pentenyl)benzene, 1-(2-(4-hexylphenyl)ethyl)-4-(1-(E)-pentenyl)benzene, 1-(2-(4-heptylphenyl)ethyl)-4-(1-(E)-pentenyl)benzene, 1-(2-(4-octylphenyl)ethyl)-4-(1-(E)-pentenyl)benzene, 1-(2-(4-nonylphenyl)ethyl)-4-(1-(E)-pentenyl)benzene, 1-(2-(4-decylphenyl)ethyl)-4-(1-(E)-pentenyl)benzene, 1-(2-(4-propylphenyl)ethyl)-4-(1-(E)-propenyl)benzene, 1-(2-(4-propylphenyl)ethyl)-4(1-(E)-butenyl)benzene, 1-(2-(4-propylphenyl)ethyl)-4-(1-(E)-hexenyl)benzene, 1-(2-(4-propylphenyl)ethyl)-4-(1-(E)-heptenyl)benzene, 1-(2-(4-propylphenyl)ethyl)-4-(1-(E)-octenyl)benzene, 1-(2-(4-decylphenyl)ethyl)-4-(1-(E)-nonenyl)benzene, 1-(2-(4-decyloxyphenyl)ethyl)-4-(1-(E)-nonenyl)benzene, 1-(4-propylcyclohexyl)-4-(2-(4-(1-(E)-propenyl)-phenyl)ethyl)benzene, 1-(4-propylcyclohexyl)-4-(2-(4-(1-(E)-butenyl)-phenyl)ethyl)benzene, 1-(4-propylcyclcohexyl)-4-(2-(4-(1-(E)-pentenyl)-phenyl)ethyl)benzene, 1-(4-propylcyclohexyl)-4-(2-(4-(1-(E)-hexenyl)-phenyl)ethyl)benzene, 1-(4-propylcyclohexyl)-4-(2-(4-(1-(E)-heptenyl)-phenyl)ethyl)benzene, 1-(4-propylcyclohexyl)-4-(2-(4-(1-(E)-octenyl)-phenyl)ethyl)benzene, 1-(4-propylcyclohexyl)-4-(2-(4-(1-(E)-nonenyl)-phenyl)ethyl)benzene, 1-(4-butylcyclohexyl-4-(2-(4-(1-(E)-pentenyl)-phenyl)ethyl)benzene, 1-(4-pentylcyclohexyl)-4-(2-(4-(1-(E)-pentenyl)-phenyl)ethyl)benzene, 1-(4-propyl-1-cyclohexenyl)-4-(2-(4-(1-(E)-pentenyl)-phenyl)ethyl)benzene, 1-(4-propyl-1-cyclohexenyl)-4-(2-(4-(1-(E)-heptenyl)-phenyl)ethyl)benzene, 1-(2-(4-trifluoromethylphenyl)ethyl)-4-(1-(E)-pentenyl)benzene, 1-(2-(4-cyanophenyl)ethyl)-4-(1-(E)-pentenyl)benzene 1-(2-(4-fluorophenyl)ethyl)-4-(1-E)-pentenyl)benzene, 1-(2-(3,4-difluorophenyl)ethyl)-4-(1-(E)-pentenyl)benzene, 1-(2-(3,4-difluorophenyl)ethyl)-4-(1-(E)-heptenyl)benzene, 1-(2-(3,4,5-trifluorophenyl)ethyl)-4-(1-(E)-propenyl)benzene, 1-(2-(3,4,5,-trifluorophenyl)ethyl)-4-(1-(E)-butenyl)benzene, 1-(2-(3,4,5-trifluorophenyl)ethyl)-4-(1-(E)-pentenyl)benzene, 1-(2-(3,4,5-trifluorophenyl)ethyl)-4-(1-(E)-hexenyl)benzene, 1-(2-(3,4,5-trifluorophenyl)ethyl)-4-(1-(E)-heptenyl)benzene, 1-(2-(3,4,5-trifluorophenyl)ethyl)-4-(1-(E)-octenyl)benzene, 1-(2-(3,4,5-trifluorophenyl)ethyl)-4-(1-(E)-nonenyl)benzene, 1-(2-(4-propyl-3,5-difluorophenyl)ethyl)-4-(1-(E)-propenyl)benzene, 1-(2-(4-propyl-3,5-difluorophenyl)ethyl)-4-(1-(E)-butenyl)benzene, 1-(2-(4-propyl-3,5-difluorophenyl)ethyl)-4-(1-(E)-pentenyl)benzene, 1-(2-(4-propyl-3,5-difluorophenyl)ethyl)-4-(1-(E)-hexenyl)benzene, 1-(2-(4-propyl-3,5-difluorophenyl)ethyl)-4-(1-(E)-heptenyl)benzene, 1-(2-(4-methyl-3,5-difluorophenyl)ethyl)-4-(1-(E)-pentenyl)benzene, 1-(2-(4-ethyl-3,5-difluorophenyl)ethyl)-4-(1-(E)-pentenyl)benzene, 1-(2-(4-butyl-3,5-difluorophenyl)ethyl)-4-(1-(E)-pentenyl)benzene, 1-(2-(4-pentyl-3,5-difluorophenyl)ethyl)- 4-(1-(E)-pentenyl)benzene, 2-fluoro-1-(2-(4-propylphenyl)ethyl)-4-(1-(E)-pentenyl)benzene, 2-fluoro-1-(2-(4-propylphenyl)

ethyl)-4-(1-(E)-hexenyl)benzene, 2-fluoro-1-(2-(4-propylphenyl)ethyl)-4-(1-(E)-heptenyl)benzene, 3-fluoro-1-(2-(4-propylphenyl)ethyl)-4-(1-(E)-pentenyl)benzene, 3-fluoro-1-(2-(4-propylphenyl)ethyl)-4-(1-(E)-hexenyl) benzene, 2-fluoro-1-(2-(3,4,5-trifluorophenyl)ethyl)-4-(1-(E)-pentenyl)benzene, 2,6-difluoro-1-(2-(3,4,5-trifluorophenyl)ethyl)-4-(1-(E)-pentenyl)benzene, 2-fluoro-1-(2-(3,4-difluorophenyl)ethyl)-4-(1-(E)-pentenyl)benzene, 2,6-difluoro-1-(2-(3,4-difluorophenyl)ethyl)-4-(1-(E)-pentenyl)benzene, 2,6-difluoro-1-(2-(4-propyl-3,5-difluorophenyl)ethyl)-4-(1-(E)-pentenyl)benzene, 2,6-difluoro-1-(2-(4-trifluoromethyl-3,5-difluorophenyl)ethyl)-4-(1-(E)-pentenyl)benzene, 2,6-difluoro-1-(2-(4-trifluoromethoxy-3,5-difluorophenyl)ethyl)-4-(1-(E)-pentenyl)benzene, 1-(2-(4-cyano-3-fluorophenyl)ethyl)-4-(1-(E)-pentenyl)benzene, 1-(2-(4-cyano-3-fluorophenyl)ethyl)-4-(1-(E)-heptenyl)benzene, 1-(2-(4-cyano-3-fluorophenyl)ethyl)-2-fluoro-4-(1-(E)-pentenyl)benzene, 1-(2-(4-cyano-3-fluorophenyl)ethyl)-2,6-difluoro-4-(1-(E)-pentenyl)benzene, 1-(2-(4-cyano-3,5-difluorophenyl)ethyl)-4-(1-(E)-pentenyl)benzene, 1-(2-(4-cyano-3,5-(difluorophenyl)ethyl)-2-fluoro-4-(1-(E)-pentenyl)benzene, 1-(2-(4-cyano-3,5-difluorophenyl)ethyl)-2,6-difluoro-4-(1-(E)-pentenyl)benzene, 1-(4,4-difluorocyclohexyl)-4-(2-(4-(1-(E)-pentenyl)phenyl)ethyl)-benzene, 1-(4-fluorocyclohexyl-4-(2-(4-(1-(E)-pentenyl)phenyl)ethyl) benzene, 1-(2-(4'-propyl-dicyclohexyl)ethyl-4-(1-(E)-pentenyl)-benzene, 1-(2-(4',4'-dipropyl-dicyclohexyl)ethyl)-4-(1-(E)-pentenyl)-benzene, 1-(2-(4'-fluoro-dicyclohexyl)ethyl)-4-(1-(E)-pentenyl)-benzene, 1-(2-(4', 4'-fluoro-dicyclohexyl)ethyl)-4-(1-(E)-pentenyl)benzene, 1-(3-(4-propylphenyl)propyl)-4-(1-(E)-pentenyl)benzene, 1-(3-(3,4-difluorophenyl)propyl)-4-(1-(E)-pentenyl)benzene, 1-(3-(3,4,5-trifluorophenyl)propyl)-4-(1-(E)-pentenyl)benzene, 1-(4-(4-propylphenyl)butyl)-4-(1-(E)-pentenyl)benzene, 1-4-(3,4-difluorophenyl)butyl)-4-(1-(E)-pentenyl)benzene, 1-(4-(3,4,5-trifluorophenyl)butyl)-4-(1-(E)-pentenyl) benzene, 1-(4-(3,5-difluoro-4-propylphenyl)butyl)-4-(1-(E)-pentenyl)benzene, 4-(4-methylbenzyloxy)-1-(1-(E)-pentenyl)benzene, 4-(4-ethylbenzyloxy)-1-(1-(E)-pentenyl) benzene, 4-(4-propylbenzyloxy)-1-(1-(E)-pentenyl) benzene, 4-(4-butylbenzyloxy)-1-(1-(E)-pentenyl)benzene, 4-(4-pentylbenzyloxy)- 1-(1-(E)-pentenyl)benzene, 4-(4-hexylbenzyloxy)-1-(1-(E)-pentenyl)benzene, 4-(4-heptylbenzyloxy)-1-(1-(E)-pentenyl)benzene, 4-(4-octylbenzyloxy)-1-(1-(E)-pentenyl)benzene, 4-(4-propylbenzyloxy)-1-(1-(E)-heptenyl)benzene, 4-(4-nonylbenzyloxy)-1-(1-(E)-heptenyl)benzene, 4-(4-hexylbenzyloxy)-1-(1-(E)-nonenyl)benzene, 4-(4-heptylbenzyloxy)-1-(1-(E)-nonenyl)benzene, 4-(4-octylbenzyloxy)-1-(1-(E)-nonenyl)benzene, 4-(4-nonylbenzyloxy)-1-(1-(E)-nonenyl)benzene, 4-(4-decylbenzyloxy)-1-(1-(E)-nonenyl)benzene, 4-(4-undecylbenzyloxy)-1-(1-(E)-nonenyl)benzene, 4-(4-trifluoromethylbenzyloxy)-1-(1-(E)-pentenyl)benzene, 4-(4-trifluoromethylbenzyloxy)-1-(1-(E)-heptenyl)benzene, 4-(4-cyano benzyloxy)-1-(1-(E)-pentenyl)benzene, 1-(4-(E)-pentenylbenzyloxy)-4-methylbenzene, 1-(4-(E)-pentenylbenzyloxy)-4-ethylbenzene, 1-(4-(E)-pentenylbenzyloxy)-4-propylbenzene, 1-(4-(E)-pentenylbenzyloxy)-4-butylbenzene, 1-(4-(E)-pentenylbenzyloxy)-4-pentylbenzene, 1-(4-(E)-pentenylbenzyloxy)-4-propylbenzene, 1-(4-(E)-hexenylbenzyloxy)-4-propylbenzene, 1-(4-(E)-heptenylbenzyloxy)-4-propylbenzene, 1-(4-(E)-pentenylbenzyloxy)-4-trifluoromethylbenzene, 1-(4-(E)-pentenylbenzyloxy)-3,4,5-trifluorobenzene, 1-(4-(E)-pentenylbenzyloxy)- 4-cyano benzene, 4-(4-methylphenoxy)-1-(1-(E)-pentenyl)benzene, 4-4-ethylphenoxy)-1-(1-(E)-pentenyl)benzene, 4-(4-propylphenoxy)-1-(1-(E)-pentenyl)benzene, 4-(4-butylphenoxy)-1-(1-(E)-pentenyl)benzene, 4-(4-pentylphenoxy)-1-(1-(E)-pentenyl)benzene, 4-(4-hexylphenoxy)-1-(1-(E)-pentenyl)benzene, 4-(4-propylphenoxy)-1-(1-(E)-propenyl)benzene, 4-(4-propylphenoxy)-1-(1-(E)-butenyl)benzene, 4-(4-propylphenoxy)-1-(1-(E)-pentenyl)benzene, 4-(4-propylphenoxy)-1-(1-(E)-hexenyl)benzene, 4-(4-propylphenoxy)-1-(1-(E)-heptenyl)benzene, 4-(4-propylphenoxy)-1-(1-(E)-octenyl)benzene, 4-(4-trifluoromethylphenoxy)-1-(1-(E)-pentenyl)benzene, (4-(1-(E)-propenyl)phenyl)-(4-propyl)benzoate, (4-(1-(E)-butenyl)phenyl)-(4-propyl)benzoate, (4-(1-(E)-pentenyl)phenyl)-(4-propyl)benzoate, (4-(1-(E)-hexenyl)phenyl)-(4-propyl)benzoate, (4-(1-(E)-heptenyl)phenyl)-(4-propyl)benzoate, (4-(1-(E)-octenyl)phenyl)-(4-propyl)benzoate, (4-(1-(E)-pentenyl)phenyl)-(4-methyl)benzoate, (4-(1-(E)-pentenyl)phenyl)-(4-ethyl)benzoate, (4-(1)-(E)-pentenyl)phenyl)-(4-propyl)benzoate, (4-(1-(E)-pentenyl)phenyl)-(4-butyl)benzoate, (4-(1-(E)-pentenyl)phenyl)-(4-pentyl)benzoate, (4-(1-(E)-propenyl)phenyl)-( 4-(4-propylcyclohexyl))benzoate, (4-(1-(E)-butenyl)phenyl)-(4-(4-propylcyclohexyl))benzoate, (4-(1-(E)-pentenyl)phenyl)-(4-(4-propylcyclohexyl))benzoate, (4-(1-(E)-hexenyl)phenyl)-(4-(4-propylcyclohexyl))benzoate, (4-(1-(E)-heptenyl)phenyl)-(4-(4-propylcyclohexyl))benzoate, (4-(1-(E)-octenyl)phenyl)-(4-(4-propylcyclohexyl))benzoate, (4-(1-(E)-pentenyl)phenyl)-(4-(4-methylcyclohexyl))benzoate, (4-(1-(E)-pentenyl)phenyl)-(4-(4-ethylcyclohexyl))benzoate, (4-(1-(E)-pentenyl)phenyl)-(4-(4-butylcyclohexyl))benzoate, (4-(1-(E)-pentenyl)phenyl)-(4-(4-pentylcyclohexyl))benzoate, (4-(1-(E)-pentenyl)phenyl)-(4-(4-propylcyclohexenyl))benzoate, (4-(1-(E)-pentenyl)phenyl)-(4-(4-pentylcyclohexenyl))benzoate, (4-(1-(E)-propenyl)phenyl)-(4-cyano-3-fluoro)benzoate, (4-(1-(E)-butenyl)phenyl)-(4-cyano-3-fluoro)benzoate, (4-(1-(E)-pentenyl)phenyl)-(4-cyano-3-fluoro)benzoate, (4-(1-(E)-hexenyl)phenyl)-(4-cyano-3-fluoro)benzoate, (4-(1-(E)-heptenyl)phenyl)-(4-cyano-3-fluoro)benzoate, (4-(1-(E)-octenyl)phenyl)-(4-cyano-3-fluoro)benzoate, (4-(1-(E)-propenyl)phenyl)-(3,4-difluoro)benzoate, (4-(1-(E)-pentenyl)phenyl)-(3,4-difluoro)benzoate, (4-(1-(E)-heptenyl)phenyl)-(3,4-difluoro)benzoate, (4-(1-(E)-propenyl)phenyl)-(3,4,5-trifluoro)benzoate, (4-(1-(E)-pentenyl)phenyl)-(3,4,5-trifluoro)benzoate, (4-(1-(E)-heptenyl)phenyl)-(3,4,5-trifluoro)benzoate, 4-methylphenyl-(4-(1-(E)-pentenyl))benzoate, 4-ethylphenyl-(4-(1-(E)-pentenyl))benzoate, 4-propylphenyl-(4-(1-(E)-pentenyl))benzoate, 4-butylphenyl-(4-(1-(E)-pentenyl))benzoate, 4-pentylphenyl-(4-(1-(E)-pentenyl))benzoate, 4-hexylphenyl-(4-(1-(E)-pentenyl))benzoate, 4-heptylphenyl-(4-(1-(E)-pentenyl))benzoate, 4-octylphenyl-(4-(1-(E)-nonenyl))benzoate, 4-nonylphenyl-(4-(1-(E)-nonenyl))benzoate, 4-decylphenyl-(4-(1-(E)-nonenyl))benzoate, 4-undecylphenyl-(4-(1-(E)-nonenyl)) benzoate, 4-octyloxyphenyl-(4-(1-(E)-nonenyl))benzoate, 4-nonyloxyphenyl-(4-(1-(E)-nonenyl))benzoate, 4-decyloxyphenyl-(4-(1-(E)-nonenyl))benzoate, 4-(4-methylcyclohexyl)phenyl-(4-(1-(E)-pentenyl))benzoate, 4-(4-ethylcyclohexyl)phenyl-(4-(1-(E)-pentenyl))benzoate, 4-(4-propylcyclohexyl)phenyl-(4-(1-(E)-pentenyl)) benzoate, 4-(4-butylcyclohexyl)phenyl-(4-(1-(E)-pentenyl)) benzoate, 4-(4-pentylcyclohexyl)phenyl-(4-(1-(E)- pentenyl))benzoate, 4-(4-hexylcyclohexyl)phenyl-(4-(1-(E)-pentenyl))benzoate, 4-(4-propylcyclohexyl )phenyl-(4-(1-(E)-propenyl))benzoate, 4-(4-propyl cyclohexyl)phenyl-(4-(1-(E)-butenyl))benzoate, 4-(4-propylcyclohexyl)phenyl-(4-(1-(E)-hexynyl))benzoate, 4-(4-propylcyclohexyl) phenyl-(4-(1-(E)-heptenyl))benzoate, 4-(4-propylcyclohexyl)phenyl-(4-(1-(E)-octenyl))benzoate, 4-(4-propylcyclohexenyl)phenyl-(4-(1-(E)-pentenyl))benzoate, 4-(4-cyano-3-fluoro)phenyl-(4-(1-(E)-pentenyl))benzoate, 4-(4-cyano-3-fluoro)phenyl-(4-(1-(E)-heptenyl))benzoate, 4-(3,4-difluoro)phenyl-(4-(1-(E)-pentenyl))benzoate, 4-(3, 4-difluoro)phenyl-(4-(1-(E)-heptenyl))benzoate, 4-(3,4,5-trifluoro)phenyl-(4-(1-(E)-pentenyl))benzoate, 4-(3,4,5-trifluoro)phenyl-(4-(1-(E)-heptenyl))benzoate, etc.

Compounds represented by the general formula (4) can be prepared according to a method described in JP-A-7-330636, JP-A-8-99917, etc.

In the liquid crystal composition of the present invention, as to the component ratio, it is preferable that the compound represented by formula (2) is 5–50 mole %, the compound represented by formula (3) is 0–95 mole %, and the compound represented by formula (4) is 0–95 mole %, based on the total amount of each component as 100 mole %. However, when both of the compounds represented by the formula (3) and (4) are not 0 mole %, it is preferable that the compound represented by the formula (3) is 10 mole % or more, and the compound represented by the formula (4) is 5 mole % or more.

The liquid crystal composition of the present invention can further contain the compounds represented by the above-mentioned formula (5) and/or compound represented by the formula (6), in addition to the phenylacetylene compound represented by the above-mentioned formula (2), the compound represented by the formula (3) and/or the compound represented by the formula (4).

In the formula (5), $J^4$ represents hydrogen atom, fluorine atom, cyano group, alkyl groups having 1–12 carbon atoms, alkenyl group having 2–12 carbon atoms, alkoxy group having 1–12 carbon atoms, alkenyloxy group having 2–12 carbon atoms, alkynyloxy group having 3–12 carbon atoms, or alkoxyalkyl group having 2–12 carbon atoms, which may be substituted by fluorine.

Concrete examples of $J^4$ include: alkyl groups, such as methyl group, ethyl group, propyl group, butyl group, pentyl group, hexyl group, heptyl group, octyl group, nonyl group, decyl group, undecyl group, and dodecyl group, or fluorinated alkyl groups thereof;

alkenyl groups, such as ethenyl group, propenyl group, butenyl group, pentenyl group, hexenyl group, heptenyl group, octenyl group, nonenyl group, decenyl group, undecenyl group, and dodecenyl group, or fluorinated alkenyl groups thereof; alkynyl groups, such as propynyl group, butynyl group, pentynyl group, hexynyl group, heptynyl group, octynyl group, nonynyl group, decynyl group, and dodecynyl group, or fluorinated alkynyl groups thereof;

alkoxy groups, such as methoxy group, ethoxy group, propoxy group, butoxy group, pentyloxy group, hexyloxy group, octyloxy group, nonyloxy group, decyloxy group, undecyloxy group, and dodecyloxy group, or fluorinated alkoxy groups thereof;

alkenyloxy groups, such as vinyloxy group, propenyloxy group, butenyloxy group, pentenyloxy group, hexenyloxy group, heptenyloxy group, octenyloxy group, nonenyloxy group, and decenyloxy group, or fluorinated alkenyloxy groups thereof;

alkynyloxy groups, such as propionyloxy group, butynyloxy group, pentynyloxy group, hexynyloxy group, heptynyloxy group, octynyloxy group, nonynyloxy group, decynyloxy group, and dodecynyloxy group, or fluorinated alkynyloxy groups thereof;

hydrogen atom; fluorine atom; trifluoromethyl group; trifluoromethoxy group; cyano group, etc.

In the formula (5), $J^5$ represents hydrogen atom, fluorine atom, cyano group, or $J^6$—(O)$m^2$. Here, $m^2$ is 0 or 1 and $J^6$ represents alkyl group having 1–12 carbon atoms, alkenyl group having 2–16 carbon atoms, or alkynyl group having 3–16 carbon atoms, which may be substituted by fluorine.

Examples of the above-mentioned $J^6$—(O)$m^2$ include:

alkyl groups, such as methyl group, ethyl group, propyl group, butyl group, pentyl group, hexyl group, heptyl group, octyl group, nonyl group, decyl group, undecyl group, and dodecyl group, or fluorinated alkyl groups thereof;

alkenyl groups, such as ethenyl group, propenyl group, butenyl group, pentenyl group, hexenyl group, heptenyl group, octenyl group, nonenyl group, decenyl group, undecenyl group, and dodecenyl group, or fluorinated alkenyl groups thereof;

alkoxyalkyl groups, such as methoxymethyl group, ethoxymethyl group, propoxymethyl group, pentyloxymethyl group, hexyloxymethyl group, heptyloxymethyl group, octyloxymethyl group, nonyloxymethyl group, decyloxymethyl group, methoxyethyl group, ethoxyethyl group, propoxyethyl group, butoxyethyl group, pentyloxyethyl group, hexyloxyethyl group, heptyloxyethyl group, octyloxyethyl group, nonyloxyethyl group, decyloxyethyl group, methoxypropyl group, ethoxypropyl group, propoxypropyl group, butoxypropyl group, pentyloxypropyl group, hexyloxypropyl group, heptyloxypropyl group, octyloxypropyl group, nonyloxypropyl group, decyloxypropyl group, methoxybutyl group, ethoxybutyl group, propoxybutyl group, butoxybutyl group, pentyloxybutyl group, hexyloxybutyl group, heptyloxybutyl group, octyloxybutyl group, nonyloxybutyl group, decyloxybutyl group, methoxypentyl butoxypentyl group, pentyloxypentyl group, hexyloxypentyl group, heptyloxypentyl group, octyloxypentyl group, nonyloxypentyl group, and decyloxypentyl group, or fluorinated alkoxyalkyl groups thereof, etc.

In the formula (5), concrete examples of the aromatic ring containing the ring structure of $X^9$, $X^{10}$, $X^{11}$, and $X^{12}$ include: 1,4-phenylene, 1,4-(2-fluoro)phenylene, 1,4-(3-fluoro)phenylene, 1,4-(2,5-difluoro)phenylene, 1,4-(3,6-difluoro)phenylene, 1,4-(2,6-difluoro)phenylene, 1,4-(3,5-difluoro)phenylene, 2,5-pyrimidinediyl, 5,2-pyrimidinediyl, 2,5-pyridinediyl, 5,2-pyridinediyl, etc.

In the formula (5), $E^1$ and $E^2$ represent each independently,

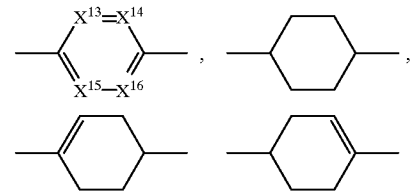

Here, $X^{13}$–$X^{16}$ represent CH or CF each independently. $W^1$ represents —$C_2H_4$—, —$CH_2O$—, or —$OCH_2$—. $f^1$ and $f^2$ represent 0 or 1 each independently, but they are not 1 at the same time.

Moreover, when $f^1$ is 1, at least either of $E^1$ or $E^2$ is

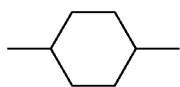

$G^5$–$G^8$ represent hydrogen atom or fluorine atom each independently.

As the compound represented by the formula (5), a compound represented by the following formula can be raised as an representative example.

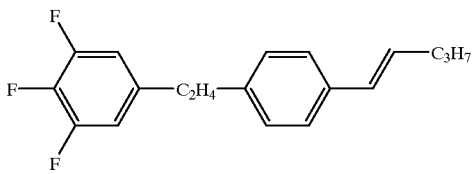

The compound represented by the formula (5) can be parpared by the method described in JP-A-9-235553, for example.

Concrete examples of the compound represented by the formula (6) include: 1-(4-fluorocyclohexyl)-4-propenylbenzene, 1-(1-trans-butenyl)-4-(4-fluorocyclohexyl)benzene, 1-(1-trans-pentenyl)-4-(4-fluorocyclohexyl)benzene, 1-(1-trans-hexenyl)-4-(4-fluorocyclohexyl)benzene, 1-(1-trans-heptenyl)-4-(4-fluorocyclohexyl)benzene, 1-(1-trans-octenyl)-4-(4-fluorocyclohexyl)benzene, 1-(1-trans-nonenyl)-4-(4-fluorocyclohexyl)benzene, 1-(1-trans-decenyl-4-(4-fluorocyclohexyl)benzene, 1-(1-trans-undecenyl)-4-(4-fluorocyclohexyl)benzene, 1-(1-trans-dodecenyl)- 4-(4-fluorocyclohexyl)benzene, 1-(4,4-difluorocyclohexyl)-4-propenyl-benzene, 1-(1-trans-butenyl)-4-(4,4-difluorocyclohexyl)benzene, 1-(1-trans-pentenyl)-4-(4,4-difluorocyclohexyl)benzene, 1-(1-trans-hexenyl)-4-(4,4-difluorocyclohexyl)benzene, 1-(1-trans-heptenyl)-4-(4,4-difluorocyclohexyl)benzene, 1-(1-trans-octenyl)-4-(4,4-difluorocyclohexyl)benzene, 1-(1-trans-nonenyl)-4-(4,4-difluorocyclohexyl)benzene, 1-(1-trans-decenyl)-4-(4,4-difluorocyclohexyl)benzene, 1-(1-trans-undecenyl)-4-(4,4-difluorocyclohexyl)benzene, 1-(1-trans-dodecenyl)-4-(4,4-difluorocyclohexyl)benzene, 4'-(4-fluorocyclohexyl)-4-propenyl-biphenyl, 4-(1-trans-butenyl)-4'-(4-fluorocyclohexyl)biphenyl, 4-(1-trans-pentenyl)-4'-(4-fluorocyclohexyl)biphenyl, 4-(1-trans-hexenyl)-4'-(4-fluorocyclohexyl)biphenyl, 4-(1-trans-heptenyl)-4'-(4-fluorocyclohexyl)biphenyl, 4-(1-trans-octenyl)-4'-(4-fluorocyclohexyl)biphenyl, 4-(1-trans-nonenyl)-4'-(4-fluorocyclohexyl)biphenyl, 4-(1-trans-decenyl)-4'-(4-fluorocyclohexyl)biphenyl, 4-(1-trans-undecenyl)-4'-(4-fluorocyclohexyl)biphenyl, 4-(1-trans-dodecenyl)-4'-(4-fluorocyclohexyl)biphenyl, 4'-(4,4-difluorocyclohexyl)-4-propenyl-biphenyl, 4-(1-trans-butenyl)-4'-(4,4-difluorocyclohexyl)biphenyl, 4-(1-trans-pentenyl)-4'-(4,4-difluorocyclohexyl)biphenyl, 4-(1-trans-hexenyl)-4'-(4,4-difluorocyclohexyl)biphenyl, 4-(1-trans-heptenyl)-4'-(4,4-difluorocyclohexyl)biphenyl, 4-(1-trans-octenyl)-4'-(4,4-difluorocyclohexyl)biphenyl, 4-(1-trans-nonenyl)-4'-(4,4-difluorocyclohexyl)biphenyl, 4-(1-trans-decenyl)-4'-(4,4-difluorocyclohexyl)biphenyl, 4-(1-trans-undecenyl)-4'-(4,4-difluorocyclohexyl)biphenyl, 4-(1-trans-dodecenyl)-4'-(4,4-difluorocyclohexyl)biphenyl, 4-propenyl-4'-(4-fluorocyclohexyl)-2,3-difluorobiphenyl, 4-(1-trans-butenyl)-4'-(4-fluorocyclohexyl)-2,3-difluorobiphenyl, 4-(1-trans-pentenyl)-41-(4-fluorocyclohexyl)-2,3-difluorobiphenyl, 4-(1-trans-hexenyl)-4'-(4-fluorocyclohexyl)-2,3-difluorobiphenyl, 4-(1-trans-heptenyl)-4'-(4-fluorocyclohexyl)-2,3-difluorobiphenyl, 4-(1-trans-octenyl)-4'-(4-fluorocyclohexyl)-2,3-difluorobiphenyl, 4-(1-trans-nonenyl)-4'-(4-fluorocyclohexyl)-2,3-difluorobiphenyl, 4-(1-trans-decenyl)-4'-(4-fluorocyclohexyl)-2,3-difluorobiphenyl, 4-(1-trans-undecenyl)-4'-(4-fluorocyclohexyl)-2,3-difluorobiphenyl, 4-(1-trans-dodecenyl)-4'-(4-fluorocyclohexyl)-2,3-difluorobiphenyl, 4-propenyl-4'-(4,4-difluorocyclohexyl)-2,3-difluorobiphenyl, 4-(1-trans-butenyl)-4'-(4,4-difluorocyclohexyl)-2,3-difluorobiphenyl, 4-(1-trans-pentenyl)-4'-(4,4-difluorocyclohexyl)-2,3-difluorobiphenyl, 4-(1-trans-hexenyl)-4'-(4,4-difluorocyclohexyl)- 2,3-difluorobiphenyl, 4-(1-trans-heptenyl)-4'-(4,4-difluorocyclohexyl)-2,3-difluorobiphenyl, 4-(1-trans-octenyl)-4'-(4,4-difluorocyclohexyl)-2,3-difluorobiphenyl, 4-(1-trans-nonenyl)-4'-(4,4-difluorocyclohexyl)-2,3-difluorobiphenyl, 4-(1-trans-decenyl)-4'-(4,4-difluorocyclohexyl)-2,3-difluorobiphenyl, 4-(1-trans-undecenyl)-41-(4,4-difluorocyclohexyl)-2,3-difluorobiphenyl, 4-(1-trans-dodecenyl)-4'-(4,4-difluorocyclohexyl)-2,3-difluorobiphenyl, etc.

Furthermore, as a compound represented by formula (6), there can be raised a compound in which: "2,3-difluoro" is replaced by "2-fluoro"; "2,3-difluoro" is replaced by "3-fluoro"; "propenyl" is replaced by "propynyl"; 1-trans-butenyl is replaced by "1-butynyl"; "1-trans-pentenyl" is replaced by "1-pentynyl"; "1-trans-hexenyl" is replaced by "1-hexynyl"; "1-trans-heptenyl" is replaced by "1-heptynyl"; "1-trans-octenyl" is replaced by "1-octynyl"; "1-trans-nonenyl" is replaced by "1-nonylyl".

There can be also raised a compound in which: "1-trans-decenyl" replaced by "1-decynyl"; "1-trans-undecenyl" is replaced by "1-undecynyl"; "1-trans-dodecenyl" is replaced by "1-dodecynyl".

Furthermore, examples of a compound represented by the formula (6) include: 1-(4-fluorocyclohexyl) propylbenzene, 1-butyl-4-(4-fluorocyclohexyl)benzene, 1-pentyl-4-(4-fluorocyclohexyl)benzene, 1-hexyl-4-(4-fluorocyclohexyl) benzene, 1-heptyl-4-(4-fluorocyclohexyl)benzene, 1-octyl-4-(4-fluorocyclohexyl)benzene, 1-nonyl-4-(4-fluorocyclohexyl)benzene, 1-decyl-4-(4-fluorocyclohexyl) benzene, 1-undecyl-4-(4-fluorocyclohexyl)benzene, 1-dodecyl-4-(4-fluorocyclohexyl)benzene, 4'-(4-fluorocyclohexyl)-4-propyl biphenyl, 4-butyl-4'-(4-fluorocyclohexyl)biphenyl, 4-pentyl-4'-(4-fluorocyclohexyl)biphenyl, 4-hexyl-4'-(4-fluorocyclohexyl) biphenyl, 4-heptyl-4'-(4-fluorocyclohexyl)biphenyl, 4-octyl-4'(4-fluorocyclohexyl)biphenyl, 4-nonyl-4'-(4-fluorocyclohexyl)biphenyl, 4-decyl-4'-(4-fluorocyclohexyl) biphenyl, 4-undecyl-4'-(4-fluorocyclohexyl)biphenyl, 4-dodecyl-4'-(4-fluorocyclohexyl)biphenyl, 4-propyl-4'-(4-fluorocyclohexyl)-2,3-difluorobiphenyl, 4-butyl-4'-(4-fluorocyclohexyl)-2,3-difluorobiphenyl, 4-pentyl-4'-(4-fluorocyclohexyl)-2,3-difluorobiphenyl, 4-hexyl-4'-(4-fluorocyclohexyl)-2,3-difluorobiphenyl, 4-heptyl-4'-(4-fluorocyclohexyl)-2,3-difluorobiphenyl, 4-octyl-4'-(4-fluorocyclohexyl)- 2,3-difluorobiphenyl, 4-nonyl-4'-(4-fluorocyclohexyl)-2,3-difluorobiphenyl, 4-decyl-4'-(4-fluorocyclohexyl)-2,3-difluorobiphenyl, 4-undecyl-4'-(4-fluorocyclohexyl)-2,3-difluorobiphenyl, 4-dodecyl-4'-(4-fluorocyclohexyl)-2,3-difluorobiphenyl, etc.

There can be also raised the compounds whose "2 and 3-difluoro" is replaced by "2-fluoro", and "2 and 3-difluoro" is replaced by "3-fluoro".

Compounds represented by the formula (6) can be prepared by the method described in JP-A-10-72583, for example.

In the liquid crystal composition of the present invention comprising the compound represented by the above formula (2), the compound represented by the above formula (3) and/or the above formula (4), the mole percentages are 5 to 50 mole % for the compound represented by the formula (2), 0 to 95 mole % the compounds represented by the formula (3) and (4) with the total mole percentage being 100%, provided that in the case where any of the compounds represented by the formulas (3) and (4) are not 0 mole %, they are 10 mole % or more for the compound represented by the formula (3), and 5 mole % or more for the compound represented by the formula (4). In the liquid crystal composition of the present invention comprising the compound represented by the above formula (2), the compound represented by the above formula (3) and/or the above formula (4), and the compound represented by the above formula (5) and/or the above formula (6), the mole percentages are 5 to 50 mole % for the compound represented by the above formula (2), 5 to 94 mole % the compounds represented by the above formula (3) and(4), and 1 to 25 mole % for the compounds represented by the above formula (5) and formula (6), with the total mole percentage being 100%, provided that neither of the compounds represented by the formula (5) or (6) is more than 25 mole %.

The liquid crystal composition of the present invention can further contain one kind of, or a plurality of chiral compounds as a twisting agent. The chiral compounds are not especially limited, however, preferable examples thereof include the following compounds (wherein * in the illustration denotes an asymmetric carbon).

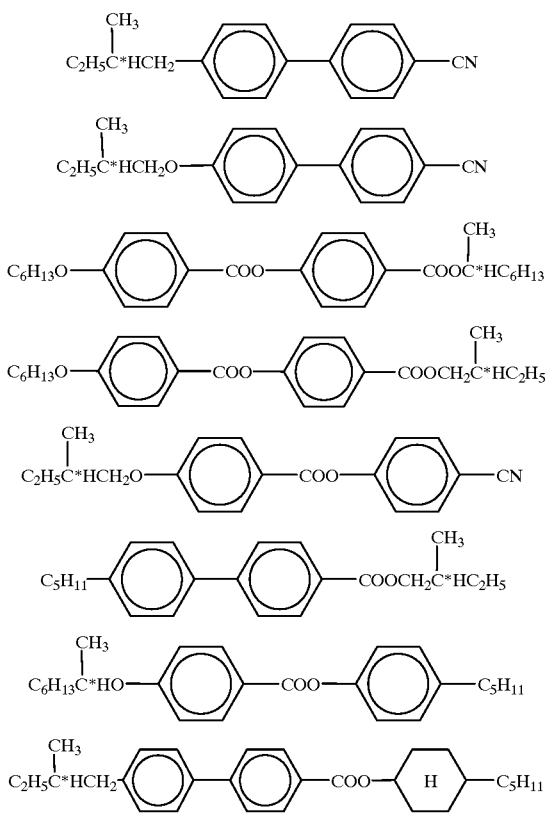

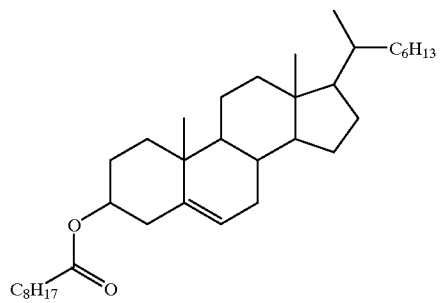

In the liquid crystal composition of the present invention, the mixing ratio of the chiral compound can be appropriately selected in mixing composition, and has no specific restriction.

The liquid crystal display element of the present invention has no specific restriction as long as it is an element including the above liquid crystal composition interposed between a pair of electrode substrates. Examples thereof include the ones having the same configurations as those of known liquid crystal display elements. The kind and form of an electrode also have no specific restriction, and known electrodes and the like can be used. Also, the manufacturing of the liquid crystal display element of the present invention can be carried out similarly in accordance with the manufacturing of conventional liquid crystal display elements. Also, other elements can appropriately be added thereto.

PREFERRED EMBODIMENTS OF THE INVENTION

Below, the present invention will now be described in more detail by way of examples, which should not be construed as to limit the scope of the present invention. The physical properties of liquid crystal compositions in illustrations were measured in accordance with the methods shown below.

(a) The anisotropy of refractive index ($\Delta n$) was measured by means of an Abbe refractometer. The measuring wavelength and the measuring temperature at this step were set to be 589 nm and 20° C., respectively.

(b) The upper limit temperature (TNI) and lower limit temperature (m.p.) of the N (nematic) phase of a liquid crystal composition were measured by means of a polarization microscope.

(c) The viscosity was measured by means of an automatic falling ball viscometer (manufactured by Anton PARR Co., AMV-200). The measurement was carried out at a measuring temperature of 20° C.

EXAMPLE 1

In a flask equipped with a stirrer and a thermometer, were charged, under an atmosphere of nitrogen, 3.46 g of the following compound (M-1), 0.17 g of dichlorobis(triphenylphosphine)palladium, 0.07 g of copper(I) iodide, 0.17 g of triphenylphosphine, 14.6 g of toluene, and 14.6 g of triethylamine. Thereafter, a solution obtained by dissolving 3.03 g of the following compound (M-2) in 5 ml of toluene was added dropwise thereto, followed by stirring at 50 to 55° C. for 3 hours. Then, the resultant mixture was filtrated and washed with toluene. The filtrate was then concentrated, after which the resultant solid was separated by silica gel chromatography to obtain 3.24 g of the desired compound. The obtained compound was measured by 1H-NMR spectrum, and found to be the compound (1-1) represented by the following structural formula.

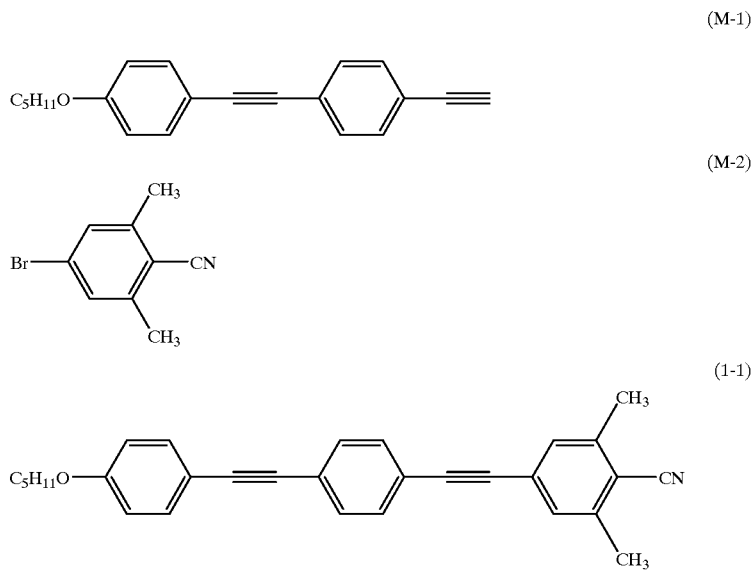

The compound (1-1) showed the following 1H-NMR spectral data.

1H-NMR: δ 0.94 (3H, t), 1.42 (4H, m), 1.80 (2H, m), 2.53 (6H, s), 3.97 (2H, t), 6.85–6.90 (2H, m), 7.27 (2H, d), 7.43–7.58 (6H, m).

The above-described compound (1-1) was evaluated for its phase sequence by polarization microscope observation. As a result, it exhibited a crystal phase at a temperature of less than 149° C., a nematic phase at a temperature in the range of 149 to 160° C., and an isotropic phase at a temperature exceeding 160° C. This indicates that the compound is a liquid crystal compound.

Also, the compound (1-1) was added in an amount of 10% by weight to a nematic composition MJ931381 (manufactured by Merck Japan Co.) to determine the anisotropy of refractive index Δn, from which the Δn extrapolated based on the concentration ratio was determined, and found to be 0.470, i.e., an extremely large value. It is noted that the measurement of Δn was carried out by means of an Abbe refractometer, at a measuring temperature of 20° C. and a measuring wavelength of 589 nm.

EXAMPLE 2

In a flask equipped with a stirrer and a thermometer, were charged, under an atmosphere of nitrogen, 14.72 g of the following material (S-1), 0.29 g of 4-pyrrolidinopyridine, 29.4 g of pyridine, and 73.6 g of toluene. The resulting mixture was cooled to 0° C., after which a solution obtained by dissolving 21.16 g of trifluoromethanesulfonic acid anhydride in 42.3 g of toluene was added dropwise thereto, which was allowed to react. After the completion of the reaction, the resultant reactant was extracted with toluene, which was then washed with water twice. The solvent was removed, and the residue was separated and purified by silica gel chromatography (eluate; hexane/ethyl acetate=20/1), resulting in 18.8 g of the intermediate (M-3) represented by the following formula.

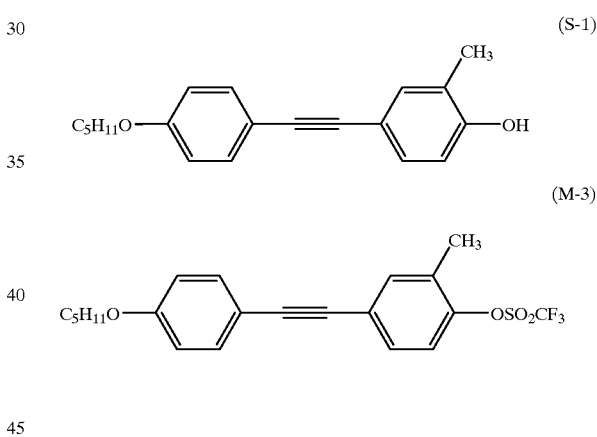

In a flask which had been replaced by nitrogen, were charged 10.1 g of DMF, 10.12 g of triethylamine, 4.26 g of the intermediate (M-1), and 0.17 g of triphenylphosphine palladium dichloride. Subsequently, at 62 °C., a solution obtained by dissolving 4.74 g of the following material (S-2) in 13.6 g of DMF was added dropwise thereto, which was allowed to react with stirring for 16 hours. After the completion of the reaction, the reaction mixture was cooled to room temperature. Then, toluene and water were added thereto to extract the reactant, which was then washed with water 3 times. The solvent was removed, and the residue was separated and purified by silica gel chromatography (eluate; hexane/ethyl acetate=20/1). Further, repulping was carried out in the order of methanol and isopropyl alcohol, followed by recrystallization with hexane. This resulted in 2 g of the compound (1-2) represented by the following formula.

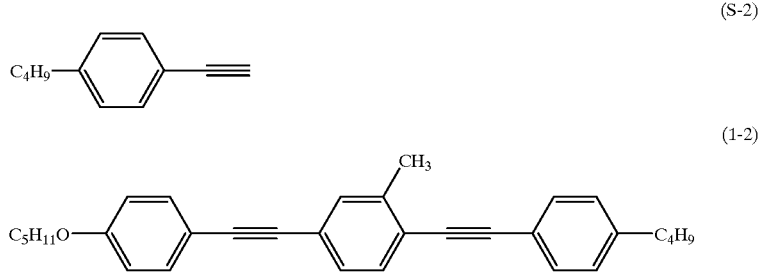

(S-2)

(1-2)

The compound (1-2) showed the following 1H-NMR spectral data.

1H-NMR: δ 0.93 (3H, t), 1.29–1.43 (6H, m), 1.47–1.66 (2H, m), 1.79 (2H, m), 2.49 (3H, s), 2.62(2H, t), 3.96 (2H, t), 6.86 (2H, d), 7.16 (2H, d), 7.25–7.46 (7H, m).

It is noted that the materials (S-1) and (S-2) can be synthesized through the following route.

Also, the Δn of the compound (1-2) measured in accordance with the method described in example 1 was found to be 0.43, i.e., an extremely large value.

EXAMPLE 3

In a flask equipped with a stirrer and a thermometer, were charged, under an atmosphere of nitrogen, 23.49 g of DMF,

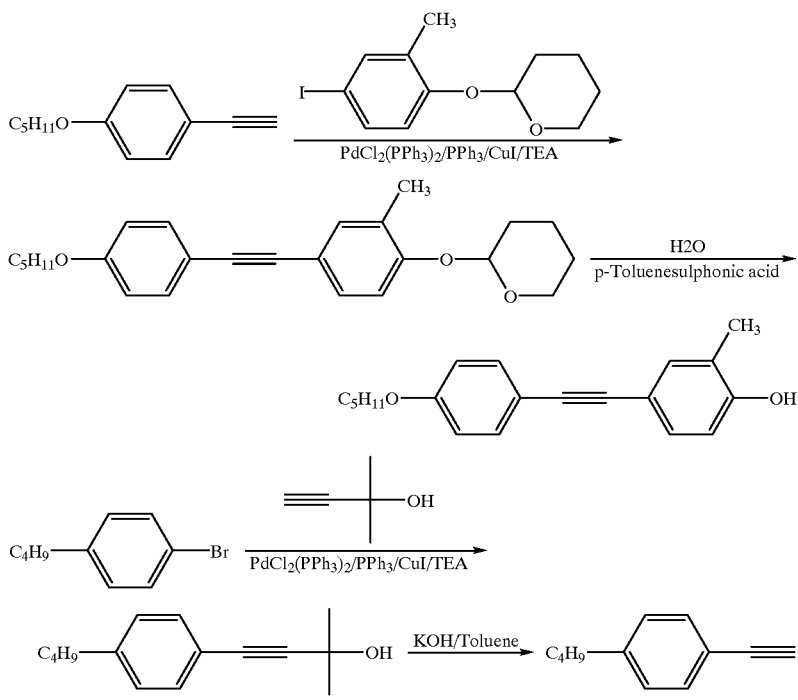

The intermediate compound (M-3) showed the following 1H-NMR spectral data.

1H-NMR: δ 0.94 (3H, t), 1.42 (4H, m), 1.79 (2H, m), 2.37 (3H, s), 3.96(2H, t), 6.85–6.88 (2H, m), 7.18–7.25 (1H, m), 7.36–7.58 (4H, m).

The compound (1-2) was evaluated for its phase sequence by polarization microscope observation. As a result, it exhibited a crystal phase at a temperature of less than 83° C., a nematic phase at a temperature in the range of 83 to 201 °C., and an isotropic phase at a temperature exceeding 201° C. This indicates that the compound is a liquid crystal compound.

13.9 g of triethylamine, 5.86 g of the intermediate (M-1) prepared in example 2, and 0.23 g of triphenylphosphine palladium dichloride. Subsequently, at 60° C., a solution obtained by dissolving 4.96 g of the following material (S-3) in 14.8 g of DMF was added dropwise thereto, which was allowed to react with stirring for 16 hours. After the completion of the reaction, the reaction mixture was cooled to room temperature. Then, toluene and water were added thereto to extract the reactant, which was then washed with water 3 times. The solvent was removed, and the residue was separated and purified by silica gel chromatography (eluate; hexane). Further, repulping was carried out by methanol to obtain 3.42 g of the compound (1-3) represented by the following formula.

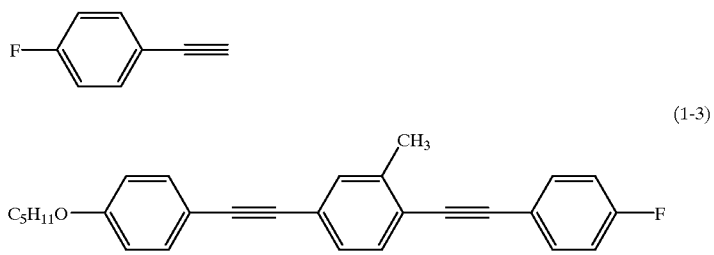

(S-3)

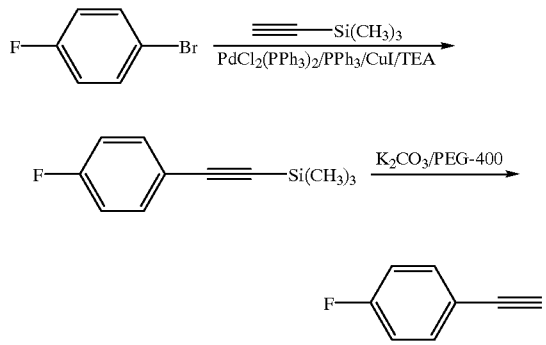

(1-3)

The compound (1-3) showed the following 1H-NMR spectral data.

1H-NMR: δ 93 (3H, t), 1.41 (4H, m), 1.79 t2H, m), 2.49 (3H, s), 3.96 (2H, t), 6.86 (2H, d), 7.05 (2H, d), 7.25–7.53 (7H, m).

It is noted that the material (S-3) can be synthesized through the following route.

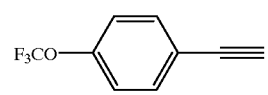

The compound (1-3) was evaluated for its phase sequence by polarization microscope observation. As a result, it exhibited a crystal phase at a temperature of less than 70° C., a smectic phase at a temperature in the range between 70° C., inclusive, and 101° C., exclusive, a nematic phase at a temperature in the range of 101 to 205° C., and an isotropic phase at a temperature exceeding 205 °C. This indicates that the compound is a liquid crystal compound.

Also, the Δn of the compound (1-3) measured in accordance with the method described in example 1 was found to be 0.44, i.e., an extremely large value.

EXAMPLE 4

In a flask equipped with a stirrer and a thermometer, were charged, under an atmosphere of nitrogen, 20.5 g of DMF, 10.1 g of triethylamine, 5.12 g of the intermediate (M-1) prepared in example 2, and 0.40 g of triphenylphosphine palladium dichloride. Subsequently, at 80° C., a solution obtained by dissolving 3.72 g of the following material (S-4) in 7.5 g of DMF was added dropwise thereto, which was allowed to react with stirring for 9 hours. After the completion of the reaction, the reaction mixture was cooled to room temperature. Then, ethyl acetate and water were added thereto to extract the reactant, which was then washed with water 3 times. The solvent was removed, and the residue was separated and purified by silica gel chromatography (eluate; hexane). Further, repulping was carried out by methanol, followed by recrystallization with hexane, to obtain 3.85 g of the compound (1-4) represented by the following formula.

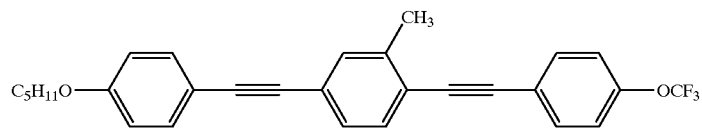

(S-4)

(1-4)

The compound (1-4) showed the following 1H-NMR spectral data.

1H-NMR: δ 0.94 (3H, t), 1.42 (4H, m), 1.80 (2H, m), 2.49 (3H, s), 3.96 (2H, t), 6.87 (2H,d), 7.19–7.57 (9H, m).

It is noted that the material (S-4) can be synthesized through the following route.

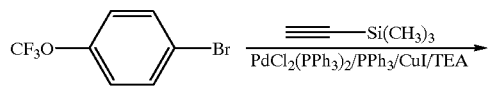

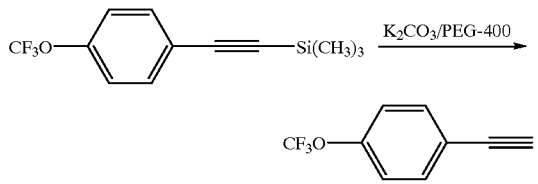

The compound (1-4) was evaluated for its phase sequence by polarization microscope observation. As a result, it exhibited a crystal phase at a temperature of less than 98° C., a smectic phase at a temperature in the range between 98° C., inclusive, and 168° C., exclusive, a nematic phase at a temperature in the range of 168 to 206° C., and an isotropic phase at a temperature exceeding 206° C. This indicates that the compound is a liquid crystal compound.

Also, the Δn of the compound (1-3) measured in accordance with the method described in example 1 was found to be 0.38, i.e., an extremely large value.

EXAMPLE 5

In a flask equipped with a stirrer and a thermometer, were charged, under an atmosphere of nitrogen, 15.2 g of ethyl acetate, 15.2 g of triethylamine, 7.68 g of the intermediate (M-1) prepared in example 2, and 0.31 g of triphenylphosphine palladium dichloride. Subsequently, at 68° C., a solution obtained by dissolving 2.12 g of the following material (R-5) in 16 g of ethyl acetate was added dropwise thereto, which was allowed to react with stirring for 7 hours. Then, 21.2 g of DMF, 0.4 g of triphenylphosphine palladium dichloride, and 3.18 g of the following material (S-5) were added thereto, which was further allowed to react for 10 hours. After the completion of the reaction, the reaction mixture was cooled to room temperature. Then, ethyl acetate and water were added thereto to extract the reactant, which was then washed with water twice. The solvent was removed, and the residue was separated and purified by silica gel chromatography (eluate; hexane/ethyl acetate=10/1). Further, repulping was carried out by hexane, followed by separation and purification by silica gel chromatography (eluate; hexane/ethyl acetate=20/1), again. Thereafter, repulping was carried out by methanol to obtain 1.73 g of the compound (1-5) represented by the following formula.

The compound (1-5) showed the following 1H-NMR spectral data.

1H-NMR: δ 0.94 (3H, t), 1.42 (4H, m), 1.80 (2H, m), 2.49 (3H, s), 2.55 (3H, s), 3.97 (2H, t), 6.87 (2H,d), 7.25–7.59 (8H, m).

It is noted that the material (S-5) can be synthesized through the following route.

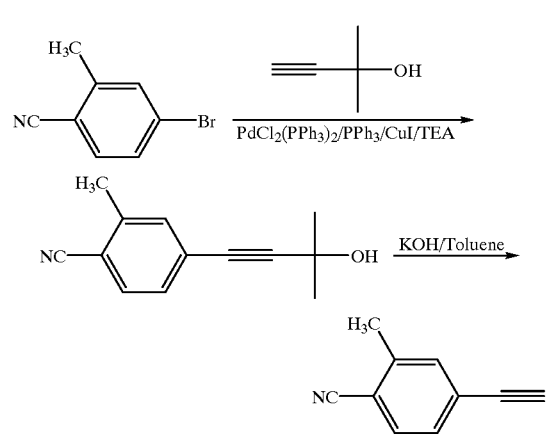

The compound (1-5) was evaluated for its phase sequence by polarization microscope observation. As a result, it exhibited a crystal phase 1 at a temperature of less than 63° C., a crystal phase 2 at a temperature in the range between 63° C., inclusive, and 106° C., exclusive, a nematic phase at a temperature in the range of 106 to 191° C., and an isotropic phase at a temperature exceeding 191° C. This indicates that the compound is a liquid crystal compound.

Also, the Δn of the compound (1-5) measured in accordance with the method described in example 1 was found to be 0.49, i.e., an extremely large value.

EXAMPLE 6

The compound (1-1) produced in example 1 was added in an amount of 5% by weight to the composition A described in Table 1, which was then increased in temperature to a liquid phase, followed by mixing to prepare a composition 1.

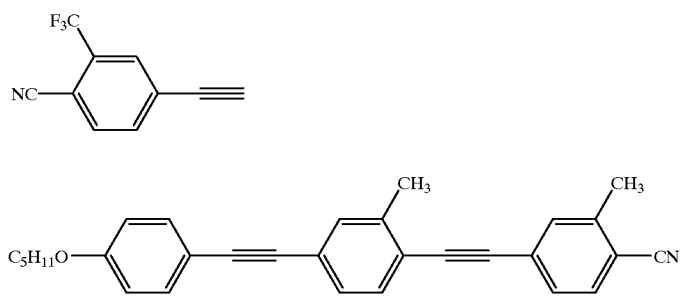

TABLE 1

| | wt % |
|---|---|
| $C_3H_7$—⬡—⬢—CN | 24 |
| $C_5H_{11}$—⬡—⬢—CN | 36 |
| $C_7H_{15}$—⬡—⬢—CN | 25 |
| $C_5H_{11}$—⬡—⬢—⬢—CN | 15 |

The compositions 1 and A were measured for their respective anisotropies of refractive index ($\Delta n$) in the same manner as in example 1. As a result, the $\Delta n$ of the composition A was found to be 0.133, while the $\Delta n$ of the composition 1 in which the compound (1-1) had been added was found to be 0.154. Thus, the $\Delta n$ of the composition 1 in which the compound of the present invention had been added is larger than that of the composition A. This reveals that the compound of the present invention improves the anisotropy of refractive index.

COMPARATIVE EXAMPLE 1

The following compound (R-1) was added in an amount of 5% by weight to the composition A described in the above Table 1, which was then increased in temperature to a liquid phase, followed by mixing. Thereafter, on cooling the mixture to room temperature, crystallization occured, resulting in a phase separation. This reveals that the compound of the present invention is more excellent in compatibility than the compound (R-1).

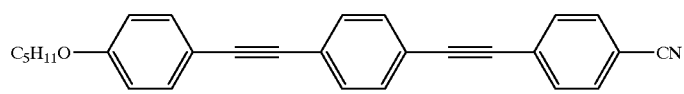

(R1-1)

EXAMPLE 7

The compound (1-1) described in example 1 was added in an amount of 10.0% by weight to the composition B described in Table 2 to prepare a liquid crystal composition 2.

TABLE 2

| | | wt % |
|---|---|---|
| (2-1) | $C_3H_7$—⬡—CO—O—⬢—$OC_2H_5$ | 23.8 |
| (2-2) | $C_4H_9$—⬡—CO—O—⬢—$OC_2H_5$ | 28.6 |
| (2-3) | $C_5H_{11}$—⬡—CO—O—⬢—$OCH_3$ | 28.6 |
| (2-4) | $C_5H_{11}$—⬡—CO—O—⬢—$OC_2H_5$ | 19.1 |

TABLE 3

|  | wt % |
|---|---|
| $C_5H_{11}$—⟨benzene⟩—≡—⟨benzene⟩—≡—⟨benzene with CH$_3$, CN, CH$_3$⟩ | 10.0 |
| Composition B | 90.0 |

Subsequently, the compositions B and 2 were measured for their respective Δn and response parameters ($\eta/\Delta n^2$). The results are shown in Table 4. It is known that the $\eta/\Delta n^2$ is proportional to the response time, and it is a parameter representing the responsibility of a liquid crystal material. The smaller the $\eta/\Delta n^2$ is, the higher speed the liquid crystal material achieves [described in "A Next-Generation Liquid Crystal Display Technology", written by Tatsuo Uchida, edited by Kogyo Chosakai Publishing Co., Ltd., p. 136 (1994)]. The Δn of the composition 2 was found to be 0.125, which indicates that the Δn thereof increased than that of the composition B. Also, the response parameter was found to be reduced, which indicates that the mixing of the compound (1-1) improves the responsibility.

TABLE 4

|  | Δn | Response parameter (mPa · s) |
|---|---|---|
| Composition 2 | 0.125 | 1906 |
| Composition A | 0.088 | 2506 |

EXAMPLE 8

Into the composition B used in example 7, was mixed the compound (1-2) described in example 2 in the ratios described in Table 5 to prepare a liquid crystal composition 3. The Δn and response parameters of the compositions 3 and B are shown in Table 6. Table 6 reveals that the composition 3 of the present invention has the larger Δn and the smaller response parameter as compared with the composition B, and it is excellent as a liquid crystal composition.

TABLE 5

|  | wt % |
|---|---|
| $C_5H_{11}O$—⟨benzene⟩—≡—⟨benzene with CH$_3$⟩—≡—⟨benzene⟩—$C_4H_9$ | 10.2 |
| Composition B | 89.8 |

TABLE 4

|  | Δn | Response parameter (mPa · s) |
|---|---|---|
| Composition 3 | 0.127 | 1501 |
| Composition B | 0.088 | 2506 |

EXAMPLE 9

The compounds (3-1), (3-2), (3-3), and (3-4) corresponding to the formula (3) and the compound (2-5) corresponding to the formula (2) were mixed in the ratios described in Table 7, resulting in a composition C.

TABLE 7

| | | wt % |
|---|---|---|
| (3-1) | C₃H₇—⟨benzene⟩—C≡C—⟨benzene-F⟩—CH=CH—C₃H₇ | 41.1 |
| (3-2) | NC—⟨benzene⟩—C≡C—⟨benzene⟩—CH=CH—C₃H₇ | 7.3 |
| (3-3) | NC—⟨benzene-F⟩—C≡C—⟨benzene⟩—CH=CH—C₃H₇ | 12.1 |
| (3-4) | C₃H₇—⟨cyclohexane⟩—⟨benzene⟩—C≡C—⟨benzene-F⟩—CH=CH—C₃H₇ | 28.2 |
| (2-5) | NC—⟨benzene⟩—⟨cyclohexane⟩—C₃H₇ | 11.3 |

Into the composition C, was mixed the compound (1-1) corresponding to the formula (1) in the ratio shown in Table 8, resulting in a liquid crystal composition 4. Then, the results of the measurement of each Δn of the liquid crystal composition 4 and the composition C are shown in Table 9.

Table 9 reveals that the liquid crystal composition 4 of the present invention has the larger Δn, and is more excellent as compared with the composition C. It was also found that the liquid crystal composition 4 had a nematic phase temperature range of −20 to 133° C., which covered an extremely wide range in either of the low- and high-temperature regions, thus being excellent.

TABLE 8

| | wt % |
|---|---|
| C₅H₁₁O—⟨benzene⟩—C≡C—⟨benzene⟩—C≡C—⟨benzene(CH₃)₂⟩—CN | 1.1 |
| Composition C | 98.9 |

TABLE 9

| | Δn |
|---|---|
| Composition 4 | 0.35 |
| Composition C | 0.34 |

EXAMPLE 10

The compound (1-2) corresponding to the formula (1) was mixed into the composition B prepared in example 9 in the ratios shown in Table 10, resulting in a liquid crystal composition 5. Then, the measurement of each Δn of the liquid crystal composition 5 and the composition C was carried out. The results are shown in Table 11.

Table 11 reveals that the liquid crystal composition 5 of the present invention has the larger Δn, and is more excellent as compared with the composition C. It was also found that the liquid crystal composition 5 had a lower limit temperature and an upper limit temperature of its nematic phase of −50° C. or less and 139° C., respectively, which covered an extremely wide range in either of the low- and high-temperature regions, thus being excellent.

TABLE 10

|  | wt % |
|---|---|
| 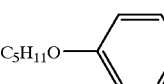 CH₃<br>C₅H₁₁O—〈 〉—≡—〈 〉—≡—〈 〉—C₄H₉ | 10.1 |
| Composition C | 89.9 |

TABLE 11

|  | Δn |
|---|---|
| Composition 5 | 0.35 |
| Composition C | 0.34 |

EXAMPLE 11

The compound (1-3) corresponding to the formula (1) was mixed into the composition C prepared in example 9 in the ratios shown in Table 12, resulting in a liquid crystal composition 6. Then, the measurement of each Δn of the liquid crystal composition 6 and the composition C was carried out. The results are shown in Table 13.

Table 13 reveals that the liquid crystal composition 6 of the present invention has the larger Δn, and is more excellent as compared with the composition C. It was also found that the liquid crystal composition 6 had a lower limit temperature and an upper limit temperature of its nematic phase of −50° C. or less and 138° C., respectively, which covered an extremely wide range in either of the low- and high-temperature regions, thus being excellent.

TABLE 12

|  | wt % |
|---|---|
| 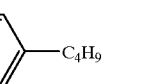 CH₃<br>C₅H₁₁O—〈 〉—≡—〈 〉—≡—〈 〉—OCF₃ | 10.8 |
| Composition C | 89.2 |

TABLE 13

|  | Δn |
|---|---|
| Composition 6 | 0.35 |
| Composition C | 0.34 |

EXAMPLE 12

The compound (1-4) corresponding to the formula (1) was mixed into the composition C prepared in example 9 in the ratio shown in Table 14, resulting in a liquid crystal composition 7. Then, the measurement of each Δn of the liquid crystal composition 7 and the composition C were carried out. The results are shown in Table 15.

Table 15 reveals that the liquid crystal composition 7 of the present invention has the larger Δn, and is more excellent as compared with the composition B.

TABLE 14

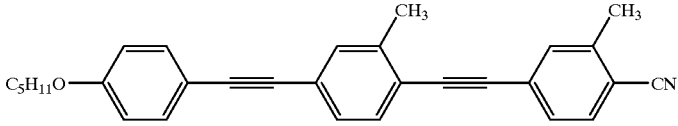

| | wt % |
|---|---|
| (structure above) | 10.2 |
| Composition C | 89.8 |

TABLE 15

| | Δn |
|---|---|
| Composition 7 | 0.36 |
| Composition C | 0.34 |

EXAMPLE 13

The compound (1-5) corresponding to the formula (1) was mixed into the composition C prepared in example 9 in the ratios shown in Table 16, resulting in a liquid crystal composition 8. Then, the measurement of each Δn of the liquid crystal composition 8 and the composition C was carried out. The results are shown in Table 17.

Table 17 reveals that the liquid crystal composition 8 of the present invention has the larger Δn, and is more excellent as compared with the composition C. It was also found that the liquid crystal composition 8 had a lower limit temperature and an upper limit temperature of its nematic phase of −50° C. or less and 138° C., respectively, which covered an extremely wide range in either of the low- and high-temperature regions, thus being excellent.

TABLE 16

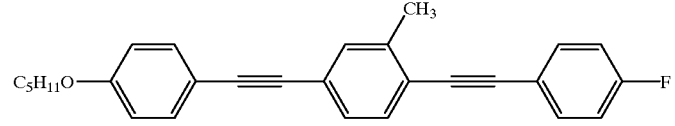

| | wt % |
|---|---|
| (structure above) | 10.2 |
| Composition C | 89.8 |

TABLE 17

| | Δn |
|---|---|
| Composition 8 | 0.36 |
| Composition C | 0.34 |

EXAMPLE 14

The compound (4-1) corresponding to the formula (4) was mixed into the composition B prepared in example 7 in the ratios shown in Table 18, resulting in a composition D.

TABLE 18

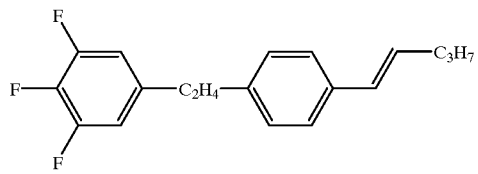

| | wt % |
|---|---|
| Composition B | 85.2 |
| (structure above) | 14.8 |

Then, into the composition D, was mixed the compound (1-1) corresponding to the formula (1) in the ratio shown in Table 19, resulting in a liquid crystal composition 9. Subsequently, the measurement of each Δn of the liquid crystal composition 9 and the composition D was carried out. The results are shown in Table 20.

Table 20 reveals that the liquid crystal composition 9 of the present invention has the larger Δn, and is more excellent as compared with the composition D.

TABLE 19

| | wt % |
|---|---|
| [Structure: $C_5H_{11}O$—phenyl—C≡C—(phenyl with $CH_3$)—C≡C—phenyl—$C_4H_9$] | 12.1 |
| Composition D | 87.9 |

TABLE 20

| | Δn |
|---|---|
| Composition 9 | 0.32 |
| Composition D | 0.30 |

EXAMPLE 15

The compound (2-6) corresponding to the formula (2) was mixed into the composition B prepared in example 7 in the ratios shown in Table 21, resulting in a composition E.

TABLE 21

| | wt % |
|---|---|
| Composition B | 90.1 |
| [Structure: $C_5H_{11}O$—phenyl—C≡C—phenyl—C≡C—(trifluorophenyl with three F)] | 9.9 |

Then, into the composition E, was mixed the compound (1-2) corresponding to the formula (1) in the ratio shown in Table 22, resulting in a liquid crystal composition 10. Subsequently, the measurement of each Δn of the liquid crystal composition 10 and the composition E was carried out at 30° C. The results are shown in Table 23.

Table 23 reveals that the liquid crystal composition 10 of the present invention has the larger Δn, and is more excellent as compared with the composition E.

TABLE 22

| | wt % |
|---|---|
| [Structure: $C_5H_{11}O$—phenyl—C≡C—phenyl—C≡C—phenyl—$C_4H_9$] | 11.4 |
| Composition E | 88.6 |

TABLE 23

| | Δn |
|---|---|
| Composition 10 | 0.16 |
| Composition E | 0.12 |

The phenylacetylene compound having an alkyl group in its skeleton, and the liquid crystal composition using the compound of the present invention each have large anisotropies of refractive index, are stable, tend to be mixed into other liquid crystals, and are especially useful as a material for constituting a liquid crystal element represented by, for example, a STN (supertwisted nematic) liquid crystal element and a PDLC (polymer dispersed liquid crystal) type liquid crystal element. Further, the liquid crystal composition of the present invention includes the compound represented by the formula (2), and the compound represented by the formula (3) and/or the formula (4). Consequently, it has a large anisotropy of refractive index and is stable, and hence it is useful especially as a material for constituting a liquid crystal element represented by a STN (supertwisted nematic) liquid crystal element or a PDLC (polymer dispersed liquid crystal) type liquid crystal element.

What is claimed is:

1. A phenylacetylene compound represented by the following general formula (1),

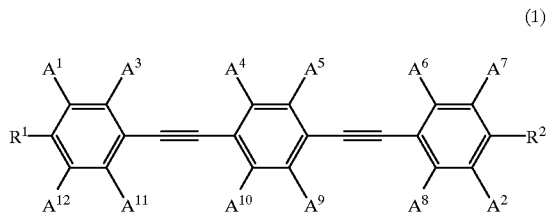
(1)

wherein $A^1$ to $A^{12}$ each independently represent a hydrogen atom, a fluorine atom, or an alkyl group having 1 to 10 carbon atoms, and at least one is an alkyl group (provided that, in $A^1$ to $A^{12}$, the cases are excluded where both of $A^1$ and $A^2$ are methyl groups at the same time, while the others are hydrogen atoms, and where both of $A^7$ and $A^{12}$ are methyl groups at the same time, while the others are hydrogen atoms); $R^1$ and $R^2$ each independently represent a fluorine atom, a cyano group, a 4-$R^3$-(cycloalkyl) group, a 4-$R^3$-(cycloalkenyl) group, or a $R^4$—(O)$_q$ group (where $R^3$ represents a hydrogen atom, a linear or branched alkyl group having 1 to 12 carbon atoms which may be substituted by fluorine, a linear or branched alkenyl group having 2 to 12 carbon atoms which may be substituted by a fluorine atom, or a linear or branched alkynyl group having 2 to 12 carbon atoms which may be substituted by a fluorine atom, and $R^4$ represents a linear or branched alkyl group having 1 to 12 carbon atoms which may be substituted by a fluorine atom, a linear or branched alkenyl group having 2 to 12 carbon atoms which may be substituted by a fluorine atom, or a linear or branched alkynyl group having 2 to 12 carbon atoms which may be substituted by a fluorine atom; and q represents 0 or 1):, provided that the compound is not

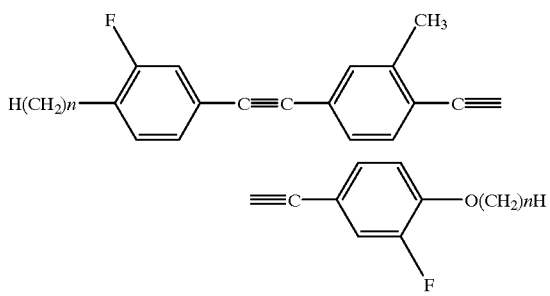

wherein n is 1 to 12.

2. The phenyl acetylene compound according to claim 1, wherein in the general formula (1), at least one group selected from the group comprising $A^4$, $A^5$, $A^9$ and $A^{10}$ is an alkyl group.

3. A compound represented by the general formula (IM-1),

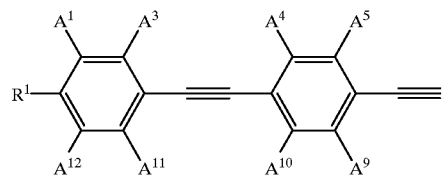
(IM-1)

wherein $A^1$, $A^3$, $A^4$, $A^5$, $A^9$, $A^{10}$, $A^{11}$, and $A^{12}$ each independently represent a hydrogen atom, a fluorine atom, or an alkyl group having 1 to 10 carbon atoms, and at least one is an alkyl group; $R^1$ represents a fluorine atom, a cyano group, a 4-$R^3$-(cycloalkyl) group, a 4-$R^3$-(cycloalkenyl) group, or a $R^4$—(O)$_q$ group (where $R^3$ represents a hydrogen atom, a linear or branched alkyl group having 1 to 12 carbon atoms which may be substituted by fluorine, a linear or branched alkenyl group having 2 to 12 carbon atoms which may be substituted by fluorine, or a linear or branched alkynyl group having a 2 to 12 carbon atoms which may be substituted by a fluorine atom, and $R^4$ represents a linear or branched alkyl group having 1 to 12 carbon atoms which may be substituted by a fluorine atom, or a linear or branched alkynyl group having 2 to 12 carbon atoms which may be substituted by a fluorine atom; and q represents 0 or 1; provided that at least one of $A^1$, $A^3$, $A^4$, $A^5$, $A^9$, $A^{10}$, $A^{11}$, and $A^{12}$ is an alkyl group.

4. A process for producing the phenyl acetylene compound shown by the following general formula (1);

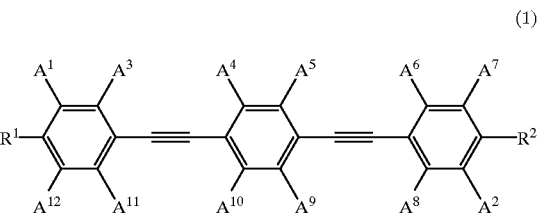
(1)

wherein $A^1$ to $A^{12}$ each independently represent a hydrogen atom, a fluorine atom, or an alkyl group having 1 to 10 carbon atoms, and at least one is an alkyl group (provided that, in $A^1$ to $A^{12}$, the cases are excluded where both of $A^1$ and $A^2$ are methyl groups at the same time, while the others are hydrogen atoms, and where both of $A^7$ and $A^{12}$ are methyl groups at the same time, while the others are hydrogen atoms); $R^1$ and $R^2$ each independently represent a fluorine atom, a cyano group, a 4-$R^3$-(cycloalkyl) group, a 4-$R^3$-(cycloalkenyl) group, or a $R^4$—(O)$_q$ group (where $R^3$ represents a hydrogen atom, a linear or branched alkyl group having 1 to 12 carbon atoms which may be substituted by fluorine, or a linear or branched alkynyl group having 2 to 12 carbon atoms which may be substituted by a fluorine atom, and $R^4$ represents a linear or branched alkyl group having 1 to 12 carbon atoms which may be substituted by a fluorine atom, a linear or branched alkyl group having 1 to 12 carbon atoms which may be substituted by a fluorine atom, or a linear or branched alkynyl group having 2 to 12 carbon atoms which may be substituted by a fluorine atom; and q represents 0 or 1, wherein derivatives represented by the general formula (IM-1),

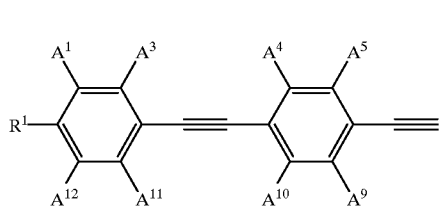

(IM-1)

wherein $A^1, A^3, A^4, A^5, A^9, A^{10}, A^{11}, A^{12}$ and $R^1$ represent the same meaning as defined in the general formula (1) provided that at least one of $A^1, A^3, A^4, A^5, A^9, A^{10}, A^{11}$, or $A^{12}$ is an alkyl group and the general formula (IM-2) are reacted in the presence of a palladium catalyst and a basic substance, with or without further addition of copper iodide,

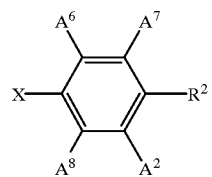

(IM-2)

in the formula, X represents I, Br or $OSO_2CF_3$, and $R^2, A^2, A^6, A^7$, and $A^8$ represent the same meaning as defined in the general formula (1).

5. A compound represented by the general formula (IM-3),

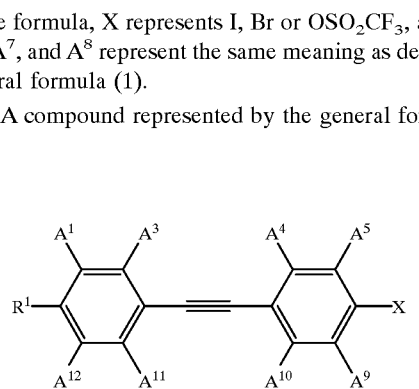

(IM-3)

in the formula, X represents I, Br or $OSO_2CF_3$; and $A^1, A^3, A^4, A^5, A^9, A^{10}, A^{11}$, and $A^{12}$ each independently represent a hydrogen atom, a fluorine atom, or an alkyl group having 1 to 10 carbon atoms, and at least one is an alkyl group; and $R^1$ represents a fluorine atom, a cyano group, a 4-$R^3$-(cycloalkyl) group, a 4-$R^3$-(cycloalkenyl) group, or a $R^4$—$(O)_q$ group (where $R^3$ represents a hydrogen atom, a linear or branched alkyl group having 1 to 12 carbon atoms which may be substituted by fluorine, a linear or branched alkenyl group having 2 to 12 carbon atoms which may be substituted by fluorine, or a linear or branched alkynyl group having a 2 to 12 carbon atoms which may be substituted by a fluorine atom, and $R^4$ represents a linear or branched alkyl group having 1 to 12 carbon atoms which may be substituted by a fluorine atom, a linear or branched alkenyl group having 2 to 12 carbon atoms which may be substituted by a fluorine atom or a linear or branched alkynyl group having 2 to 12 carbon atoms which may be substituted by a fluorine atom; and q represents 0 or 1; provided that at least one of them is an alkyl group, and that the compound is not:

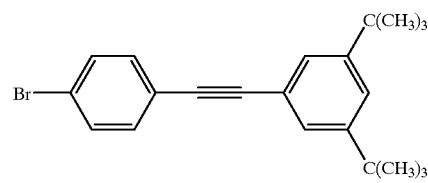

6. A process for producing the phenyl acetylene compound shown by the following general formula (1);

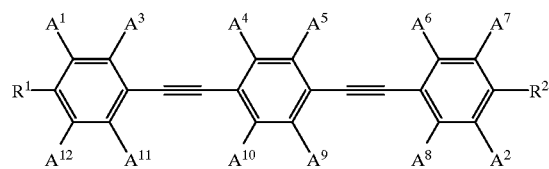

(1)

wherein $A^1$ to $A^{12}$ each independently represent a hydrogen atom, a fluorine atom, or an alkyl group having 1 to 10 carbon atoms, and at least one is an alkyl group (provided that, in $A^1$ to $A^{12}$, the cases are excluded where both of $A^1$ and $A^2$ are methyl groups at the same time, while the others are hydrogen atoms, and where both of $A^7$ and $A^{12}$ are methyl groups at the same time, while the others are hydrogen atoms); $R^1$ and $R^2$ each independently represent a fluorine atom, a cyano group, a 4-$R^3$-(cycloalkyl) group, a 4-$R^3$-(cycloalkenyl) group, or a $R^4$—$(O)_q$ group (where $R^3$ represents a hydrogen atom, a linear or branched alkyl group having 1 to 12 carbon atoms which may be substituted by fluorine, a linear or branched alkenyl group having 2 to 12 carbon atoms which may be substituted by fluorine, or a linear or branched alkynyl group having 2 to 12 carbon atoms which may be substituted by a fluorine atom, and $R^4$ represents a linear or branched alkyl group having 1 to 12 carbon atoms which may be substituted by a fluorine atom, a linear or branched alkenyl group having 2 to 12 carbon atoms which may be substituted by a fluorine atom, or a linear or branched alkynyl group having 2 to 12 carbon atoms which may be substituted by a fluorine atom, and q represents 0 or 1, wherein a compound represented by the general formula (IM-3),

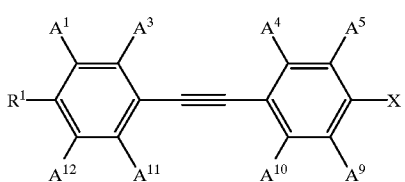

(IM-3)

in the formula, X represents I, Br or $OSO_2CF_3$; and $A^1, A^3, A^4, A^5, A^9, A^{10}, A^{11}, A^{12}$ and $R^1$ represent the same meaning as defined in the general formula (1), provided that at least one of them is an alkyl group;

and ethynylbenzene derivative represented by the general formula (IM-4) are reacted in the presence of a palladium catalyst and a basic substance, with or without further addition of copper iodide (IM-4)

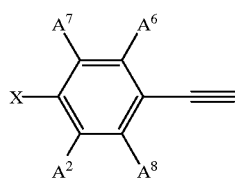

in the formula, $A^2$, $A^6$, $A^7$ and $A^8$ represent the same meaning as defined in the general formula (1).

7. A liquid crystal composition comprising at least one phenylacetylene compound represented by the following formula (2)

(2)

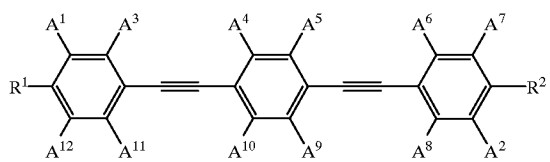

wherein $A^1$ to $A^{12}$ each independently represent a hydrogen atom, a fluorine atom, or an alkyl group having 1 to 10 carbon atoms, and at least one is an alkyl group; $R^1$ and $R^2$ each independently represent a fluorine atom, a cyano group, a 4-$R^3$-(cycloalkyl) group, a 4-$R^3$-(cycloalkenyl) group, or a $R^4$—(O)$_q$ group (where $R^3$ represents a hydrogen atom, a linear or branched alkyl group having 1 to 12 carbon atoms which may be substituted by fluorine, a linear or branched alkenyl group having 2 to 12 carbon atoms which may be substituted by a fluorine atom or a linear or branched alkynyl group having 2 to 12 carbon atoms which may be substituted by a fluorine atom, and $R^4$ represents a linear or branched alkyl group having 1 to 12 carbon atoms which may be substituted by a fluorine atom, a linear or branched alkyl group having 1 to 12 carbon atoms which may be substituted by a fluorine atom, a linear or branched alkenyl group having 2 to 12 carbon atoms which may be substituted by a fluorine atom, or a linear or branched alkynyl group having 2 to 12 carbon atoms which may be substituted by a fluorine atom; and q represents 0 or 1); provided that the compound is not

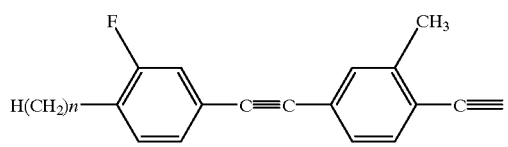

-continued

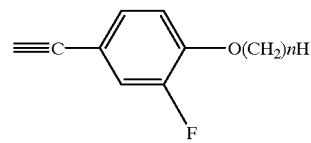

wherein n is 1 to 12.

8. A liquid crystal element, wherein the liquid crystal composition of claim 7, is interposed between a pair of electrode substrates.

9. A liquid crystal composition, comprising at least one phenylacetylene compound represented by the following formula (2);

(2)

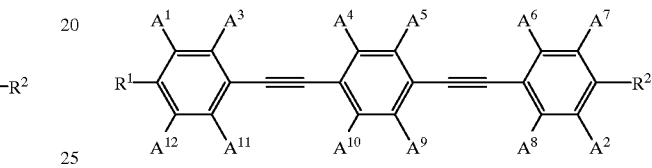

wherein $A^1$ to $A^{12}$ each independently represent a hydrogen atom, a fluorine atom, or an alkyl group having 1 to 10 carbon atoms, and at least one is an alkyl group; $R^1$ and $R^2$ each independently represent a fluorine atom, a cyano group, a 4-$R^3$-(cycloalkyl) group, a 4-$R^3$-(cycloalkenyl) group, or a $R^4$—(O)$_q$ group (where $R^3$ represents a hydrogen atom, a linear or branched alkyl group having 1 to 12 carbon atoms which may be substituted by fluorine, a linear or branched alkenyl group having 2 to 12 carbon atoms which may be substituted by a fluorine atom or a linear or branched alkynyl group having 2 to 12 carbon atoms which may be substituted by a fluorine atom, and $R^4$ represents a linear or branched alkyl group having 1 to 12 carbon atoms which may be substituted by a fluorine atom, a linear or branched alkenyl group having 2 to 12 carbon atoms which may be substituted by a fluorine atom, or a linear or branched alkynyl group having 2 to 12 carbon atoms which may be substituted by a fluorine atom; and q represents 0 to 1) and at least one compound represented by the following formula (3), and/or a compound represented by the following formula (4), (3)

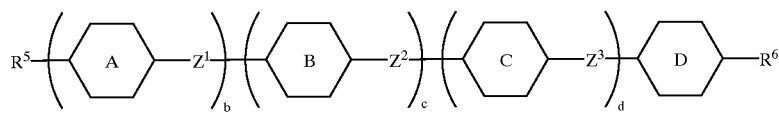

in the formula (3), rings A, B, C, and D each independently represent 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, 6,3-cyclohexenylene, 2,5-pyrimedinediyl, 5,2-pyrimedinediyl, 2,5-pyridinediyl, 5,2-pyridinediyl, 2,5-dioxanediyl or 5,2-dioxanediyl (provided that each hydrogen atom on the rings A, B, C, and D may be substituted by a fluorine atom); $R^5$ to $R^6$ represent a hydrogen atom, a fluorine atom, a fluoromethyl group, a difluoromethyl group, a trifluoromethyl group, a fluoromethoxy group, a difluoromethoxy group, a trifluoromethoxy group, a cyano group, a linear or branched alkyl group having 1 to 12 carbon atoms, a linear or branched alkenyl group having 2 to 12 carbon atoms, a linear or branched alkoxy group having 1 to 12 carbon atoms, a linear or branched alkenyloxy group having 2 to 12 carbon atoms, a linear or branched alkynyloxy group having 3 to 12 carbon atoms, a linear or branched alkoxyalkyl group having 2 to 16 carbon atoms, or a linear or branched alkoxyalkenyl group having 3 to 16 carbon atoms, and methylene groups or alkyl, alkenyl, or alkynyl group thereof may be replaced with oxygen, sulfur or silicon atom; $Z^1$, $Z^2$ and $Z^3$ each independently represent —COO—, —OCO—, —OCH$_2$—, —CH$_2$O—, an alkylene group having 1 to 5 carbon atoms, an alkenylene group having 2 to 5 carbon atoms, an alkynylene group having 2 to 5 carbon atoms, or a single bond; b, c and d each independently represent 0 or 1, and satisfy b+c+d≧1; in the bond of $R^5$ with ring A, ring B or ring C, each ring does not bond directly to an alkenyl group, and in the bond of $R^6$ with the ring D, the ring does not bond directly to an alkenyl group; and (4)

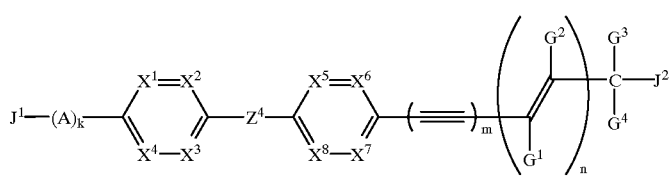

in the formula (4), $J^1$ represents a hydrogen atom, and fluorine atom, a cyano group, or a $J^3(O)m^1$ (where $J^3$ represents an alkyl group having 1 to 12 carbon atoms, an alkenyl group having 2 to 12 carbon atoms, or an alkynyl group having 2 to 12 carbon atoms, which may be substituted by fluorine, and $m^1$ represents 0 or 1) $J^2$ represents a hydrogen atom or an alkyl group having 1 to 12 carbon atoms, an alkenyl group having 2 to 12 carbon atoms, or an alkoxyalkyl group having 2 to 16 carbon atoms; A represents

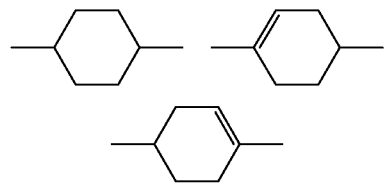

k, m, and n represent 0 or 1, but m≠n, $X^1$ to $X^8$ each independently represent CH or CF; $G^1$ to $G^4$ each independently represent a hydrogen atom or a fluorine atoms; and $Z^4$ represents —C≡C— or —C≡C—C≡C— (provided that when n=0, $Z^4$ is —C≡C—).

10. The liquid crystal composition according to claim 7 or 9, further comprising at least one compound represented by the following formula (5) and/or a compound represented by the following formula (6), (5)

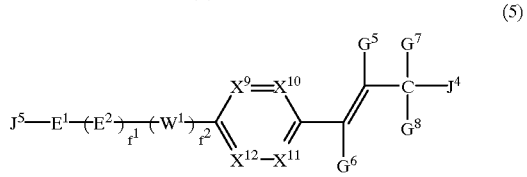

in the formula (5), $X^9$ to $X^{12}$ each independently represent CH or CF; $J^4$ represents a hydrogen atom, a fluorine atom, a cyano group, an alkyl group having 1 to 12 carbon atoms, an alkenyl group having 2 to 12 carbon atoms, an alkoxy group having 1 to 12 carbon atoms, an alkenyloxy group having 2 to 12 carbon atoms, or an alkynyloxy group having 3 to 12 carbon atoms, or an alkoxyalkyl group having 2 to 12 carbon atoms, which may be substituted by fluorine; $J^5$ represents a hydrogen atom, a fluorine atom, a cyano group, or a $J^6$—(O)$m^2$ (where $m^2$ is 0 or 1, and $J^6$ represents an alkyl group having 1 to 12 carbon atoms, an alkenyl group having 2 to 16 carbon atoms, and an alkynyl group having 3 to 16 carbon atoms, which may be substituted by fluorine); $E^1$ and $E^2$ each independently represents

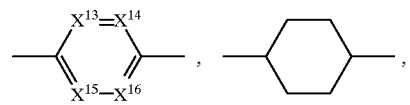

-continued

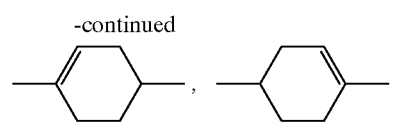

where $X^{13}$ to $X^{16}$ each independently represent CH or CF; $W^1$ represents —C$_2$H$_4$—, —CH$_2$O— or —OCH$_2$—; $f^1$ and $f^2$ each independently represent 0 or 1, but $f^1$ and $f^2$ are not 1 at the same time; and when $f^1$ is 1, at least one of $E^1$ or $E^2$ is

and $G^5$ to $G^8$ each independently represent a hydrogen atom or a fluorine atom, and (6)

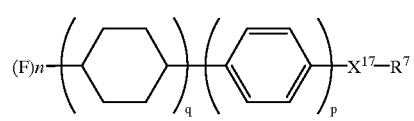

in the formula (6), $R^7$ represents an alkyl group having 1 to 10 carbon atoms, and a hydrogen atom on the benzene ring in the formula (5) may be substituted by a fluorine atom; n, p, and q each independently represent 1 or 2; and $X^{17}$ represents trans- —CH=CH— or an ethynyl group (privided that when n is 1, $X^{17}$ may be —CH$_2$—CH$_2$—).

11. The liquid crystal composition according to claim 9, wherein the compound represented by the above formula (3) is at least one of the compounds represented by the following formulae (7) to (11),

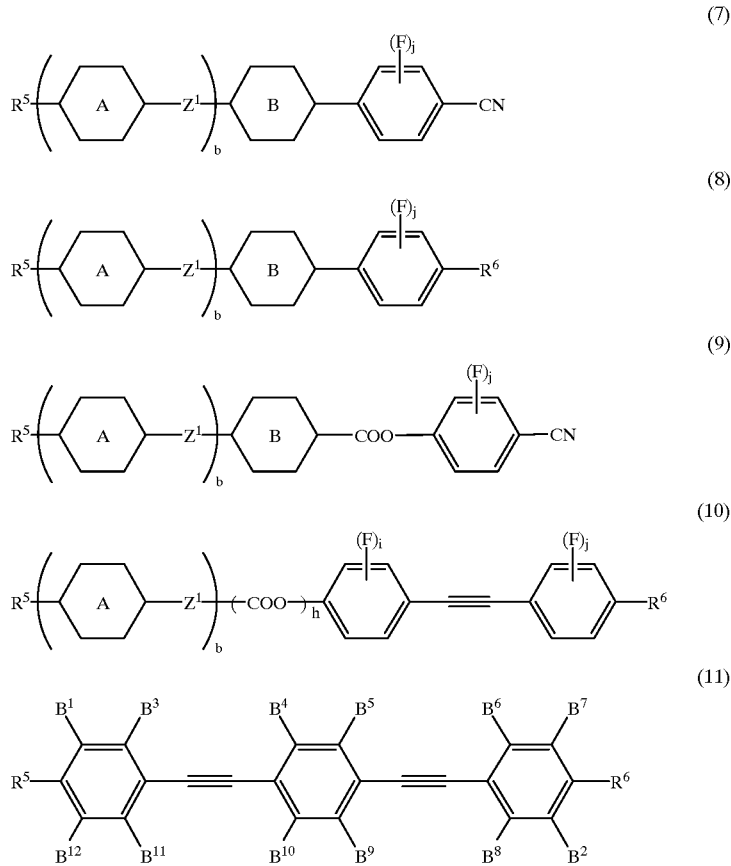

in the formulae (7) to (11), $R^5$, $R^6$, ring A, ring B, $Z^1$ and b are the same as defined in the formula (2), respectively; j is 0, 1 or 2; h is 0 or 1, and i is 0, 1 or 2; in the formula (10), $B^1$ to $B^{12}$ represent each independently a hydrogen atom, a fluorine atom a chlorine atom.

12. The liquid crystal composition according to claim 9, wherein mole percentages of the compound represented by the formula (2), the compound represented by the formula (3) and the compound represented by the formula (4) are 5 to 50 mole %, 0 to 95 mole % and 0 to 95 mole %, respectively, with the total mole percentage being 100%, provided that in the case where any of the compounds represented by the formulae (3) and (4) are not 0 mole %, they are 10 mole % or more for the compound represented by the formula (3), and 5 mole % or more for the compound represented by the formula (4).

13. A liquid crystal composition according to claim 10, wherein mole percentage of the compound represented by the formula (2), the sum of the compounds represented by the formula (3) and (4), and the sum of the compounds represented by the formula (5) and (6) are 5 to 50 mole %, 5 to 94 mole %, and 1 to 50 mole %, respectively, with the total mole percentage being 100%, provided that neither of the compounds represented by the formula (5) or (6) is more than 25 mole %.

14. A liquid crystal element which comprises the liquid crystal composition of claim 9 interposed between a pair of electrode substrates.

* * * * *

UNITED STATES PATENT AND TRADEMARK OFFICE
CERTIFICATE OF CORRECTION

PATENT NO.    : 6,149,837
DATED         : November 21, 2000
INVENTOR(S)   : Chizu Sekine et al.

It is certified that error appears in the above-identified patent and that said Letters Patent is hereby corrected as shown below:

Title page,
Item [73], Assignees: "please change the second assignee from "Agency of Industrial Science and Technology" to -- Japan as represented by Secretary of Agency of Industrial Science and Technology --.

Column 96,
Line 26, afte "atom," please insert the following: -- a linear or branched alkenyl group having 2 to 12 carbon atoms which may be substituted by a flourine atom --.
Line 58, after "fluorine," please insert the following: -- a linear or branched alkenyl group having 2 to 12 carbon atoms which may be substituted by a fluorine atom --.
Line 60, change "alkyl" to -- alkenyl --.
Line 61, change "1" to -- 2 --.

Column 99,
Lines 39-41, please delete the following: "a linear or branched alkyl group having 1 to 12 carbon atoms which may be substituted by a fluorine atom,"

Column 100, claim 9,
Lines 59-60, please change "2,5-pyrimedinediyl, 5,2-pyrimedinediyl," to -- 2,5-pyrimidinediyl, 5,2-pyrimidinediyl, --.

Column 103, claim 11,
Line 41, please insert -- or -- before "a".

Signed and Sealed this

Twelfth Day of February, 2002

Attest:

*Attesting Officer*

JAMES E. ROGAN
*Director of the United States Patent and Trademark Office*